US006479259B1

(12) United States Patent
Herman et al.

(10) Patent No.: US 6,479,259 B1
(45) Date of Patent: Nov. 12, 2002

(54) HUMAN PERIPHERAL NERVE, TETRODOTOXIN-RESISTANT SODIUM CHANNEL α-SUBUNIT POLYPEPTIDE

(75) Inventors: Ronald Herman, Sunnyvale, CA (US); Stephen Gregory Delgado, San Francisco, CA (US); Linda Marie Fish, La Honda, CA (US); Lakshmi Sangameswaran, San Jose, CA (US); Douglas Kenneth Rabert, Mountain View, CA (US)

(73) Assignee: Syntex (U.S.A.) LLC, Palo Alto, CA (US)

( * ) Notice: Subject to any disclaimer, the term of this patent is extended or adjusted under 35 U.S.C. 154(b) by 0 days.

(21) Appl. No.: 09/527,013

(22) Filed: Mar. 16, 2000

Related U.S. Application Data

(60) Division of application No. 08/843,417, filed on Apr. 15, 1997, now Pat. No. 6,184,349, which is a continuation-in-part of application No. 08/511,828, filed on Oct. 11, 1995, now abandoned.

(51) Int. Cl.[7] ........................ C12N 15/12; C12N 15/63; C12N 5/10

(52) U.S. Cl. .................. 435/69.1; 435/320.1; 435/325; 536/23.5

(58) Field of Search ......................... 536/23.5; 435/325, 435/320.1, 69.1

(56) References Cited

U.S. PATENT DOCUMENTS 5,132,296 A 7/1992 Cherksey
5,380,836 A 1/1995 Rogart

FOREIGN PATENT DOCUMENTS

| | | |
|---|---|---|
| WO | WO 96/14077 | 5/1796 |
| WO | WO 97/01577 | 1/1997 |
| WO | WO 99/27097 | 6/1999 |

OTHER PUBLICATIONS

Catterall, W. A. (1993) "Strucure and Function of Voltage–gated Ion Channels," *TINS* 16:500–506.

Numa, S., et al. (1986) "Molecular Structure of Sodium Channles," *Ann. New York Acad. Sci.* 479:338–354.

Rogart, R.B., et al. (1989) "Molecular Cloning of A Putative Tetrodotoxin–resistant Rat Heart Na+ Channel Isoform," *Proc. Natl. Acad. Sci.* 86:8170–8174.

Satin, J., et al. (1992) "A Mutant TTX–resistant Cardiac Sodium Channel with TTX–sensitive Properties," *Science*256:1202–1205.

Moss, B.L., et al. (1993) "Nerve Growth Factor Treatment of PC12 Cells Induces the Expression of a Novel Sodium Channel Gene, Peripheral Nerve Type 1 (PN1)," *Abstracts, Soc. Neurosci* 23rd Annual Meeting, Washington, D.C., Abstract No. 121.7.

D'Arcangelo, G., et al. (1993) "Neuronal Growth Factor Regualtion of Two Different Sodium Channel Types through Distinct Signal Transduction Pathways," *J. Cell Biol.* 122:915–921.

Roy, M.L., et al. (1992) "Differential Properties of Tetrodotoxin–sensitive and Tetrodotoxin resistant Sodium Channels in Rat Dorsal Root Ganglion Neurons," *J. Neurosci.* 12:2104–2111.

Beckh, S. (1990) "Differential Expression of Sodium Channel mRNAs in Rat Peripheral Nervous System and Innervated Tissues," *Fed. Euro. Biochem. Soc.* 262:317–322.

Noda, M., et al. (1986) "Existence of Distinct sodium Channel Messenger RNA in Rat Brain," *Nature*, 320:188–192.

Noda, M. et al. (1989) "A Single Point Mutation Confers Tetrodotoxin and Saxitosin Insensitivity on the Sodium Channel II," *Fed. Euro. Biochem Soc.* 259:213–216.

Rabert, D.K., et al. "A Tetrodotoxin–resistant Voltage–gated Sodium Channel from Human Dorsal Root Ganglia, hPN3/SCN10A," *Pain* 78:107–114.

Sangameswaran, L., "Structure and Function of a Novel Voltage–gated, Tetrodotoxin–resistant Sodium Channel Specific to Sensory Neurons," *J. Biol. Chem.* 271:5953–5956.

*Primary Examiner*—Michael Pak
(74) *Attorney, Agent, or Firm*—Sheela Mohan-Peterson; Rohan Peries

(57) ABSTRACT

The present invention relates to a voltage-gated sodium channel present in peripheral nerve tissue that is tetrodotoxin-resistant. One aspect of the present invention is purified and isolated DNA encoding this sodium channel. Another aspect of the present invention is the recombinant protein expressed by this DNA, expression vectors comprising the DNA sequence, and host cells transformed with these expression vectors. Another aspect of this invention is the use of this voltage-gated, tetrodotoxin-resistant sodium channel as a therapeutic target for compounds to treat disorders of the peripheral nervous system.

7 Claims, 57 Drawing Sheets

```
CTTCCCCAAG AAGAATGAGA AGATGGAGCT CCCCTTTGCG TCCGTGGGAA CTACCAATTT 60
CAGACGGTTC ACTCCAGAGT CACTGGCAGA GATCGAGAAG CAGATTGCTG CTCACCGCGC 120
AGCCAAGAAG GCCAGAACCA AGCACAGAGG ACAGGAGGAC AAGGGCGAGA AGCCCAGGCC 180
TCAGCTGGAC TTGAAAGCCT GTAACCAGCT GCCCAAGTTC TATGGTGAGC TCCCAGCAGA 240
ACTGGTCGGG GAGCCCCTGG AGGACCTAGA CCCTTTCTAC AGCACACACC GGACATTCAT 300
GGTGTTGAAT AAAAGCAGGA CCATTTCCAG ATTCAGTGCC ACTTGGGCCC TGTGGCTCTT 360
CAGTCCCTTC AACCTGATCA GAAGAACAGC CATCAAAGTG TCTGTCCATT CCTGGTTCTC 420
CATATTCATC ACCATCACTA TTTTGGTCAA CTGCGTGTGC ATGACCCGAA CTGATCTTCC 480
AGAGAAAGTC GAGTACGTCT TCACTGTCAT TTACACCTTC GAGGCTCTGA TTAAGATACT 540
GGCAAGAGGG TTTTGTCTAA ATGAGTTCAC TTATCTTCGA GATCCGTGGA ACTGGCTGGA 600
CTTCAGTGTC ATTACCTTGG CGTATGTGGG TGCAGCGATA GACCTCCGAG GAATCTCAGG 660
CCTGCGGACA TTCCGAGTTC TCAGAGCCCT GAAAACTGTT TCTGTGATCC CAGGACTGAA 720
```

FIG. 1A

```
GGTCATCGTG GGAGCCCTGA TCCACTCAGT GAGGAAGCTG GCCGACGTGA CTATCCTCAC 780
AGTCTTCTGC CTGAGCGTCT TCGCCTTGGT GGGCCTGCAG CTCTTTAAGG GGAACCTTAA 840
GAACAAATGC ATCAGGAACG GAACAGATCC CCACAAGGCT GACAACCTCT CATCTGAAAT 900
GGCAGAATAC ATCTTCATCA AGCCTGGTAC TACGGATCCC TTACTGTGCG GCAATGGGTC 960
TGATGCTGGT CACTGCCCTG GAGGCTATGT CTGCCTGAAA ACTCCTGACA ACCCGGATTT 1020
TAACTACACC AGCTTTGATT CCTTTGCGTG GGCATTCCTC TCACTGTTCC GCCTCATGAC 1080
GCAGGACTCC TGGGAGCGCC TGTACCAGCA GACACTCCGG GCTTCTGGGA AAATGTACAT 1140
GGTCTTTTTC GTGCTGGTTA TTTTCCTTGG ATCGTTCTAC CTGGTCAATT TGATCTTGGC 1200
CGTGGTCACC ATGGCGTATG AAGAGCAGAG CCAGGCAACA ATTGCAGAAA TCGAAGCCAA 1260
GGAAAAAAAG TTCCAGGAAG CCCTTGAGGT GCTGCAGAAG GAACAGGAGG TGCTGGCAGC 1320
CCTGGGGATT GACACGACCT CGCTCCAGTC CCACAGTGGA TCACCCTTAG CCTCCAAAAA 1380
CGCCAATGAG AGAAGACCCA GGGTGAAATC AAGGGTGTCA GAGGGCTCCA CGGATGACAA 1440
CAGGTCACCC CAATCTGACC CTTACAACCA GCGCAGGATG TCTTTCCTAG GCCTGTCTTC 1500
```

FIG. 1B

```
AGGAAGACGC AGGGCTAGCC ACGGCAGTGT GTTCCACTTC CGAGCGCCCA GCCAAGACAT 1560
CTCATTTCCT GACGGGATCA CGGATGATGG GGTCTTTCAC GGAGACCAGG AAAGCCGTCG 1620
AGGTTCCATA TTGCTGGGCA GGGGTGCTGG GCAGACAGGT CCACTCCCCA GGAGCCCACT 1680
GCCTCAGTCC CCCAACCCTG GCCGTAGACA TGGAGAAGAG GGACAGCTCG GAGTGCCCAC 1740
TGGTGAGCTT ACCGCTGGAG CGCCTGAAGG CCCGGCACTC GACACTACAG GGCAGAAGAG 1800
CTTCCTGTCT GCGGGCTACT TGAACGAACC TTTCCGAGCA CAGAGGGCCA TGAGCGTTGT 1860
CAGTATCATG ACTTCTGTCA TTGAGGAGCT TGAAGAGTCT AAGCTGAAGT GCCCACCCTG 1920
CTTGATCAGC TTCGCTCAGA AGTATCTGAT CTGGGAGTGC TGCCCCAAGT GGAGGAAGTT 1980
CAAGATGGCG CTGTTCGAGC TGGTGACTGA CCCCTTCGCA GAGCTTACCA TCACCCTCTG 2040
CATCGTGGTG AACACCGTCT TCATGGCCAT GGAGCACTAC CCCATGACCG ATGCCTTCGA 2100
TGCCATGCTT CAAGCCGGCA ACATTGTCTT CACCGTGTTT TTCACAATGG AGATGGCCTT 2160
CAAGATCATT GCCTTCGACC CCTACTATTA CTTCCAGAAG AAGTGGAATA TCTTCGACTG 2220
TGTCATCGTC ACCGTGAGCC TTCTGGAGCT GAGCGCATCC AAGAAGGGCA GCCTGTCTGT 2280
```

FIG. 1C

```
GCTCCGTACC TTCCGCTTGC TGCGGGTCTT CAAGCTGGCC AAGTCCTGGC CCACCCTGAA 2340
CACCCTCATC AAGATCATCG GGAACTCCGT GGGGGCCCTG GGCAACCTGA CCTTTATCCT 2400
GGCCATCATC GTCTTCATCT TCGCCCTGGT CGGAAAGCAG CTTCTCTCAG AGGACTACGG 2460
GTGCCGCAAG GACGGCGTCT CCGTGTGGAA CGGCGAGAAG CTCCGCTGGC ACATGTGTGA 2520
CTTCTTCCAT TCCTTCCTGG TCGTCTTCCG AATCCTCTGC GGGGAGTGGA TCGAGAACAT 2580
GTGGGTCTGC ATGGAGGTCA GCCAGAAATC CATCTGCCTC ATCCTCTTCT TGACTGTGAT 2640
GGTGCTGGGC AACCTAGTGG TGCTCAACCT TTTCATCGCT TTACTGCTGA ACTCCTTCAG 2700
CGCGGACAAC CTCACGGCTC CAGAGGATGA CGGGGAGGTG AACAACTTGC AGTTAGCACT 2760
GGCCAGGATC CAGGTACTTG GCCATCGGGC CAGCAGGGCC ATCGCCAGTT ACATCAGCAG 2820
CCACTGCCGA TTCCGCTGGC CCAAGGTGGA GACCCAGCTG GGCATGAAGC CCCCACTCAC 2880
CAGCTCAGAG GCCAAGAACC ACATTGCCAC TGATGCTGTC AGTGCTGCAG TGGGGAACCT 2940
GACAAAGCCA GCTCTCAGTA GCCCCAAGGA GAACCACGGG GACTTCATCA CTGATCCCAA 3000
CGTGTGGGTC TCTGTGCCCA TTGCTGAGGG GGAATCTGAC CTCGACGAGC TCGAGGAAGA 3060
```

FIG. 1D

```
TATGGAGCAG GCTTCGCAGA GCTCCTGGCA GGAAGAGGAC CCCAAGGGAC AGCAGGAGCA 3120
GTTGCCACAA GTCCAAAAGT GTGAAAACCA CCAGGCAGCC AGAAGCCCAG CCTCCATGAT 3180
GTCCTCTGAG GACCTGGCTC CATACCTGGG TGAGAGCTGG AAGAGGAAGG ATAGCCCTCA 3240
GGTCCCTGCC GAGGGAGTGG ATGACACGAG CTCCTCTGAG GGCAGCACGG TGGACTGCCC 3300
GGACCCAGAG GAAATCCTGA GGAAGATCCC CGAGCTGGCA GATGACCTGG ACGAGCCCGA 3360
TGACTGTTTC ACAGAAGGCT GCACTCGCCG CTGTCCCTGC TGCAACGTGA ATACTAGCAA 3420
GTCTCCTTGG GCCACAGGCT GGCAGGTGCG CAAGACCTGC TACCGCATCG TGGAGCACAG 3480
CTGGTTTGAG AGTTTCATCA TCTTCATGAT CCTGCTCAGC AGTGGAGCGC TGGCCTTTGA 3540
GGATAACTAC CTGGAAGAGA AACCCCGAGT GAAGTCCGTG CTGGAGTACA CTGACCGAGT 3600
GTTCACCTTC ATCTTCGTCT TTGAGATGCT GCTCAAGTGG GTAGCCTATG GCTTCAAAAA 3660
GTATTTCACC AATGCCTGGT GCTGGCTGGA CTTCCTCATT GTGAACATCT CCCTGACAAG 3720
CCTCATAGCG AAGATCCTTG AGTATTCCGA CGTGGCGTCC ATCAAAGCCC TTCGGACTCT 3780
CCGTGCCCTC CGACCGCTGC GGGCTCTGTC TCGATTCGAA GGCATGAGGG TAGTGGTGGA 3840
```

FIG. 1E

```
TGCCCTCGTG GGCGCCATCC CCTCCATCAT GAACGTCCTC CTCGTCTGCC TCATCTTCTG 3900
GCTCATCTTC AGCATCATGG GCGTGAACCT CTTCGCCGGG AAATTTTCGA AGTGCGTCGA 3960
CACCAGAAAT AACCCATTTT CCAACGTGAA TTCGACGATG GTGAATAACA AGTCCGAGTG 4020
TCACAATCAA AACAGCACCG GCCACTTCTT CTGGGTCAAC GTCAAAGTCA ACTTCGACAA 4080
CGTCGCTATG GGCTACCTCG CACTTCTTCA GGTGGCAACC TTCAAAGGCT GGATGGACAT 4140
AATGTATGCA GCTGTTGATT CCGGAGAGAT CAACAGTCAG CCTAACTGGG AGAACAACTT 4200
GTACATGTAC CTGTACTTCG TCGTTTTCAT CATTTTCGGT GGCTTCTTCA CGCTGAATCT 4260
CTTTGTTGGG GTCATAATCG ACAACTTCAA CCAACAGAAA AAAAAGCTAG GAGGCCAGGA 4320
CATCTTCATG ACAGAAGAGC AGAAGAAGTA CTACAATGCC ATGAAGAAGC TGGGCTCCAA 4380
GAAACCCCAG AAGCCCATCC CACGGCCCCT GAATAAGTAC CAAGGCTTCG TGTTTGACAT 4440
CGTGACCAGG CAAGCCTTTG ACATCATCAT CATGGTTCTC ATCTGCCTCA ACATGATCAC 4500
CATGATGGTG GAGACCGACG AGCAGGGCGA GGAGAAGACG AAGGTTCTGG GCAGAATCAA 4560
CCAGTTCTTT GTGGCCGTCT TCACGGGCGA GTGTGTGATG AAGATGTTCG CCCTGCGACA 4620
```

FIG. 1F

GTACTACTTC ACCAACGGCT GGAACGTGTT CGACTTCATA GTGGTGATCC TGTCCATTGG 4680
GAGTCTGCTG TTTTCTGCAA TCCTTAAGTC ACTGGAAAAC TACTTCTCCC CGACGCTCTT 4740
CCGGGTCATC CGTCTGGCCA GGATCGGCCG CATCCTCAGG CTGATCCGAG CAGCCAAGGG 4800
GATTCGCACG CTGCTCTTCG CCCTCATGAT GTCCCTGCCC GCCCTCTTCA ACATCGGCCT 4860
CCTCCTCTTC CTCGTCATGT TCATCTACTC CATCTTCGGC ATGGCCAGCT TCGCTAACGT 4920
CGTGGACGAG GCCGGCATCG ACGACATGTT CAACTTCAAG ACCTTTGGCA ACAGCATGCT 4980
GTGCCTGTTC CAGATCACCA CCTCGGCCGG CTGGGACGGC CTCCTCAGCC CCATCCTCAA 5040
CACGGGGCCT CCCTACTGCG ACCCCAACCT GCCCAACAGC AACGGTTCCC GGGGGAACTG 5100
CGGGAGCCCG GCGGTGGGCA TCATCTTCTT CACCACCTAC ATCATCATCT CCTTCCTCAT 5160
CGTGGTCAAC ATGTACATCG CAGTGATTCT GGAGAACTTC AACGTGGCCA CCGAGGAGAG 5220
CACGGAGCCC CTGAGCGAGG ACGACTTCGA CATGTTCTAT GAGACCTGGG AGAAGTTCGA 5280
CCCGGAGGCC ACCCAGTTCA TTGCCTTTTC TGCCCTCTCA GACTTCGCGG ACACGCTCTC 5340
CGGCCCTCTT AGAATCCCCA AACCCAACCA GAATATATTA ATCCAGATGG ACCTGCCGTT 5400

FIG. 1G

```
GGTCCCCGGG GATAAGATCC ACTGTCTGGA CATCCTTTTT GCCTTCACAA AGAACGTCTT 5460
GGGAGAATCC GGGGAGTTGG ACTCCCTGAA GACCAATATG GAAGAGAAGT TTATGGCGAC 5520
CAATCTCTCC AAAGCATCCT ATGAACCAAT AGCCACCACC CTCCGGTGGA AGCAGGAAGA 5580
CCTCTCAGCC ACAGTCATTC AAAAGGCCTA CCGGAGCTAC ATGCTGCACC GCTCCTTGAC 5640
ACTCTCCAAC ACCCTGCATG TGCCCAGGGC TGAGGAGGAT GGCGTGTCAC TTCCCGGGGA 5700
AGGCTACGTT ACATTCATGG CAAACAGTGG ACTCCCGGAC AAATCAGAAA CTGCCTCTGC 5760
TACGTCTTTC CCGCCATCCT ATGACAGTGT CACCAGGGGC CTGAGTGACC GGGCCAACAT 5820
TAACCCATCT AGCTCAATGC AAAATGAAGA TGAGGTCGCT GCTAAGGAAG GAAACAGCCC 5880
TGGACCTCAG TGAAGGCACT CAGGCATGCA CAGGGCAGGT TCCAATGTCT TTCTCTGCTG 5940
TGCTAACTCC TTCCCTCTGG AGGTGGCACC AACCTCCAGC CTCCACCAAT GCATGTCACT 6000
GGTCATGGTG TCAGAACTGA ATGGGGACAT CCTTGAGAAA GCCCCCACCC CAATAGGAAT 6060
CAAAAGCCAA GGATACTCCT CCATTCTGAC GTCCCTTCCG AGTTCCCAGA AGATGTCATT 6120
GCTCCCTTCT GTTTGTGACC AGAGACGTGA TTCACCAACT TCTCGGAGCC AGAGACACAT 6180
```

FIG. 1H

```
ACCAAAGACT TTTCTGCTGG TGTCGGGCAG TCTTAGAGAA GTCACGTAGG GGTTGGCACT 6240

GAGAATTAGG GTTTGCATGC CTGCATGCTC ACAGCTGCCG GACAATACCT GTGAGTCGGC 6300

CATTAAAATT AATATTTTTA AAGTTAAAAA AAAAAAAAAA AAAA                  6344
```

FIG. 1I

```
Met Glu Leu Pro Phe Ala Ser Val Gly Thr Thr Asn Phe Arg Arg Phe
  1               5                  10                  15

Thr Pro Glu Ser Leu Ala Glu Ile Glu Lys Gln Ile Ala Ala His Arg
            20                  25                  30

Ala Ala Lys Lys Ala Arg Thr Lys His Arg Gly Gln Glu Asp Lys Gly
        35                  40                  45

Glu Lys Pro Arg Pro Gln Leu Asp Leu Lys Ala Cys Asn Gln Leu Pro
    50                  55                  60

Lys Phe Tyr Gly Glu Leu Pro Ala Glu Leu Val Gly Glu Pro Leu Glu
 65                  70                  75                  80

Asp Leu Asp Pro Phe Tyr Ser Thr His Arg Thr Phe Met Val Leu Asn
                 85                  90                  95
```

FIG. 2A

```
Lys Ser Arg Thr Ile Ser Arg Phe Ser Ala Thr Trp Ala Leu Trp Leu
            100                 105                 110

Phe Ser Pro Phe Asn Leu Ile Arg Arg Thr Ala Ile Lys Val Ser Val
        115                 120                 125
                                                     |----------

His Ser Trp Phe Ser Ile Phe Ile Thr Ile Thr Ile Leu Val Asn Cys
    130                 135                 140
----------------------IS1---------------------------------------

Val Cys Met Thr Arg Thr Asp Leu Pro Glu Lys Val Glu Tyr Val Phe
145                 150                 155                 160
------------------|                     |----------------------

Thr Val Ile Tyr Thr Phe Glu Ala Leu Ile Lys Ile Leu Ala Arg Gly
                165                 170                 175
------IS2-----------------------------------------------|
```

FIG. 2B

```
Phe Cys Leu Asn Glu Phe Thr Tyr Leu Arg Asp Pro Trp Asn Trp Leu
            180                 185                 190
                                                |--------------

Asp Phe Ser Val Ile Thr Leu Ala Tyr Val Gly Ala Ala Ile Asp Leu
        195                 200                 205
-----------IS3-------------------------------------------|

Arg Gly Ile Ser Gly Leu Arg Thr Phe Arg Val Leu Arg Ala Leu Lys
    210                 215                 220
                |----------------------------IS4---------------

Thr Val Ser Val Ile Pro Gly Leu Lys Val Ile Val Gly Ala Leu Ile
225                 230                 235                 240
-------------------------------|

His Ser Val Arg Lys Leu Ala Asp Val Thr Ile Leu Thr Val Phe Cys
                245                 250                 255
                                 |------------------------------
```

FIG. 2C

```
Leu Ser Val Phe Ala Leu Val Gly Leu Gln Leu Phe Lys Gly Asn Leu
            260                 265                 270
-----------------IS5--------------------------------------------|

Lys Asn Lys Cys Ile Arg Asn Gly Thr Asp Pro His Lys Ala Asp Asn
        275                 280                 285
                         •                                   •

Leu Ser Ser Glu Met Ala Glu Tyr Ile Phe Ile Lys Pro Gly Thr Thr
    290                 295                 300

Asp Pro Leu Leu Cys Gly Asn Gly Ser Asp Ala Gly His Cys Pro Gly
305                 310                 315                 320
                         •

Gly Tyr Val Cys Leu Lys Thr Pro Asp Asn Pro Asp Phe Asn Tyr Thr
                325                 330                 335
                                                     •
```

FIG. 2D

```
Ser Phe Asp Ser Phe Ala Trp Ala Phe Leu Ser Leu Phe Arg Leu Met
            340                 345                 350

Thr Gln Asp Ser Trp Glu Arg Leu Tyr Gln Gln Thr Leu Arg Ala Ser
        355                 360                 365
                ♦

Gly Lys Met Tyr Met Val Phe Phe Val Leu Val Ile Phe Leu Gly Ser
    370                 375                 380
                |------------------------------IS6-------------

Phe Tyr Leu Val Asn Leu Ile Leu Ala Val Val Thr Met Ala Tyr Glu
385                 390                 395                 400
------------------------------------------------------|

Glu Gln Ser Gln Ala Thr Ile Ala Glu Ile Glu Ala Lys Glu Lys Lys
                405                 410                 415
```

FIG. 2E

```
Phe Gln Glu Ala Leu Glu Val Leu Gln Lys Glu Gln Glu Val Leu Ala
            420                 425                 430

Ala Leu Gly Ile Asp Thr Thr Ser Leu Gln Ser His Ser Gly Ser Pro
        435                 440                 445

Leu Ala Ser Lys Asn Ala Asn Glu Arg Arg Pro Arg Val Lys Ser Arg
    450                 455                 460

Val Ser Glu Gly Ser Thr Asp Asp Asn Arg Ser Pro Gln Ser Asp Pro
465                 470                 475                 480

Tyr Asn Gln Arg Arg Met Ser Phe Leu Gly Leu Ser Ser Gly Arg Arg
                485                 490                 495
```

FIG. 2F

```
Arg Ala Ser His Gly Ser Val Phe His Phe Arg Ala Pro Ser Gln Asp
            500                 505                 510
        o

Ile Ser Phe Pro Asp Gly Ile Thr Asp Asp Gly Val Phe His Gly Asp
        515                 520                 525

Gln Glu Ser Arg Arg Gly Ser Ile Leu Leu Gly Arg Gly Ala Gly Gln
    530                 535                 540
                        o

Thr Gly Pro Leu Pro Arg Ser Pro Leu Pro Gln Ser Pro Asn Pro Gly
545                 550                 555                 560

Arg Arg His Gly Glu Glu Gly Gln Leu Gly Val Pro Thr Gly Glu Leu
                565                 570                 575
```

FIG. 2G

```
Thr Ala Gly Ala Pro Glu Gly Pro Ala Leu Asp Thr Thr Gly Gln Lys
            580                 585                 590
                             ↑

Ser Phe Leu Ser Ala Gly Tyr Leu Asn Glu Pro Phe Arg Ala Gln Arg
        595                 600                 605

Ala Met Ser Val Val Ser Ile Met Thr Ser Val Ile Glu Glu Leu Glu
    610                 615                 620

Glu Ser Lys Leu Lys Cys Pro Pro Cys Leu Ile Ser Phe Ala Gln Lys
625                 630                 635                 640

Tyr Leu Ile Trp Glu Cys Cys Pro Lys Trp Arg Lys Phe Lys Met Ala
                645                 650                 655
```

FIG. 2H

```
Leu Phe Glu Leu Val Thr Asp Pro Phe Ala Glu Leu Thr Ile Thr Leu
            660                 665                 670
        |-------------------------------------------------------

Cys Ile Val Val Asn Thr Val Phe Met Ala Met Glu His Tyr Pro Met
        675                 680                 685
-------IIS1-------------------------------|

Thr Asp Ala Phe Asp Ala Met Leu Gln Ala Gly Asn Ile Val Phe Thr
    690                 695                 700
                        |---------------------------------------

Val Phe Phe Thr Met Glu Met Ala Phe Lys Ile Ile Ala Phe Asp Pro
705                 710                 715                 720
----------IIS2--------------------------------------|

Tyr Tyr Tyr Phe Gln Lys Lys Trp Asn Ile Phe Asp Cys Val Ile Val
                725                 730                 735
                        |--------------------------IIS3--------
```

FIG. 2I

```
Thr Val Ser Leu Leu Glu Leu Ser Ala Ser Lys Lys Gly Ser Leu Ser
            740                 745                 750
--------------------------------------|               o

Val Leu Arg Thr Phe Arg Leu Leu Arg Val Phe Lys Leu Ala Lys Ser
        755                 760                 765
|------------------------------IIS4----------------------------

Trp Pro Thr Leu Asn Thr Leu Ile Lys Ile Ile Gly Asn Ser Val Gly
    770                 775                 780
--------------|

Ala Leu Gly Asn Leu Thr Phe Ile Leu Ala Ile Ile Val Phe Ile Phe
785                 790                 795                 800
             •     |----------------------IIS5--------------------

Ala Leu Val Gly Lys Gln Leu Leu Ser Glu Asp Tyr Gly Cys Arg Lys
                805                 810                 815
-----------------------------------|
```

FIG. 2J

```
Asp Gly Val Ser Val Trp Asn Gly Glu Lys Leu Arg Trp His Met Cys
            820                 825                 830

Asp Phe Phe His Ser Phe Leu Val Val Phe Arg Ile Leu Cys Gly Glu
        835                 840                 845

Trp Ile Glu Asn Met Trp Val Cys Met Glu Val Ser Gln Lys Ser Ile
    850                 855                 860
                                                            |--

Cys Leu Ile Leu Phe Leu Thr Val Met Val Leu Gly Asn Leu Val Val
865                 870                 875                 880
-------------------------IIS6-----------------------------------

Leu Asn Leu Phe Ile Ala Leu Leu Leu Asn Ser Phe Ser Ala Asp Asn
                885                 890                 895
-----------------------------------|
```

FIG. 2K

```
Leu Thr Ala Pro Glu Asp Asp Gly Glu Val Asn Asn Leu Gln Leu Ala
            900                 905                 910

Leu Ala Arg Ile Gln Val Leu Gly His Arg Ala Ser Arg Ala Ile Ala
        915                 920                 925

Ser Tyr Ile Ser Ser His Cys Arg Phe Arg Trp Pro Lys Val Glu Thr
    930                 935                 940

Gln Leu Gly Met Lys Pro Pro Leu Thr Ser Ser Glu Ala Lys Asn His
945                 950                 955                 960

Ile Ala Thr Asp Ala Val Ser Ala Ala Val Gly Asn Leu Thr Lys Pro
                965                 970                 975
```

FIG. 2L

```
Ala Leu Ser Ser Pro Lys Glu Asn His Gly Asp Phe Ile Thr Asp Pro
            980                 985                 990

Asn Val Trp Val Ser Val Pro Ile Ala Glu Gly Glu Ser Asp Leu Asp
        995                 1000                1005

Glu Leu Glu Glu Asp Met Glu Gln Ala Ser Gln Ser Ser Trp Gln Glu
    1010                1015                1020

Glu Asp Pro Lys Gly Gln Gln Glu Gln Leu Pro Gln Val Gln Lys Cys
1025                1030                1035                1040

Glu Asn His Gln Ala Ala Arg Ser Pro Ala Ser Met Met Ser Ser Glu
                1045                1050                1055

Asp Leu Ala Pro Tyr Leu Gly Glu Ser Trp Lys Arg Lys Asp Ser Pro
            1060                1065                1070
                                                            o
```

FIG. 2M

```
Gln Val Pro Ala Glu Gly Val Asp Asp Thr Ser Ser Ser Glu Gly Ser
        1075                1080                1085

Thr Val Asp Cys Pro Asp Pro Glu Glu Ile Leu Arg Lys Ile Pro Glu
    1090                1095                1100

Leu Ala Asp Asp Leu Asp Glu Pro Asp Asp Cys Phe Thr Glu Gly Cys
1105                1110                1115                1120

Thr Arg Arg Cys Pro Cys Cys Asn Val Asn Thr Ser Lys Ser Pro Trp
                1125                1130                1135
                                     •

Ala Thr Gly Trp Gln Val Arg Lys Thr Cys Tyr Arg Ile Val Glu His
            1140                1145                1150
                                               |--------------
```

FIG. 2N

```
Ser Trp Phe Glu Ser Phe Ile Ile Phe Met Ile Leu Leu Ser Ser Gly
        1155                1160                1165
------------IIIS1-------------------------------------------------

Ala Leu Ala Phe Glu Asp Asn Tyr Leu Glu Glu Lys Pro Arg Val Lys
    1170                1175                1180
--------------|

Ser Val Leu Glu Tyr Thr Asp Arg Val Phe Thr Phe Ile Phe Val Phe
1185                1190                1195                1200
    |------------------------------------IIIS2-----------------

Glu Met Leu Leu Lys Trp Val Ala Tyr Gly Phe Lys Lys Tyr Phe Thr
                1205                1210                1215
-------------------------------------------|

Asn Ala Trp Cys Trp Leu Asp Phe Leu Ile Val Asn Ile Ser Leu Thr
            1220                1225                1230
    |------------------------------IIIS3-----•-----------------
```

FIG. 2O

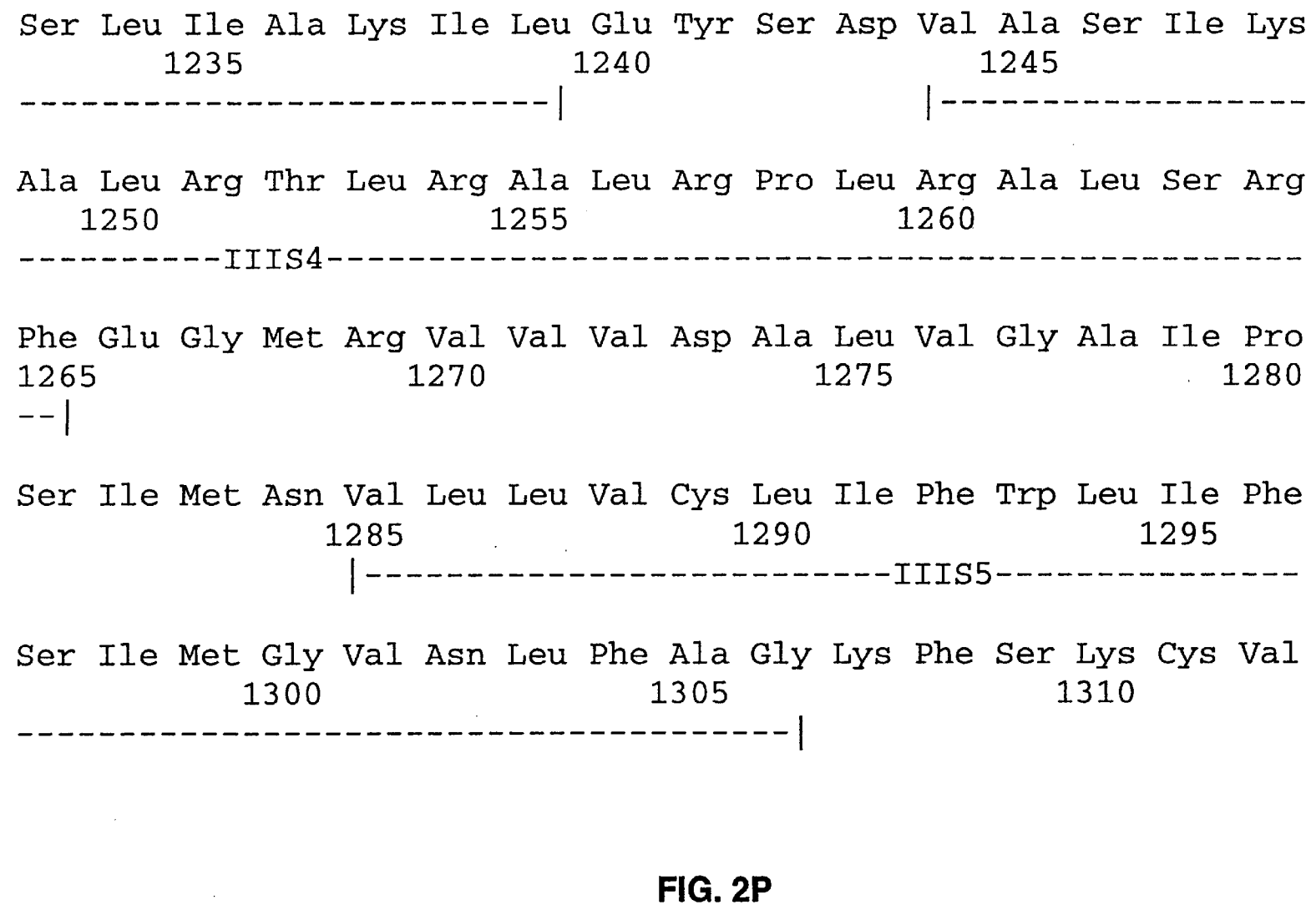

```
Ser Leu Ile Ala Lys Ile Leu Glu Tyr Ser Asp Val Ala Ser Ile Lys
        1235                1240                1245
--------------------------|                 |------------------

Ala Leu Arg Thr Leu Arg Ala Leu Arg Pro Leu Arg Ala Leu Ser Arg
    1250                1255                1260
----------IIIS4-------------------------------------------------

Phe Glu Gly Met Arg Val Val Val Asp Ala Leu Val Gly Ala Ile Pro
1265                1270                1275                1280
--|

Ser Ile Met Asn Val Leu Leu Val Cys Leu Ile Phe Trp Leu Ile Phe
                1285                1290                1295
                |--------------------------IIIS5---------------

Ser Ile Met Gly Val Asn Leu Phe Ala Gly Lys Phe Ser Lys Cys Val
            1300                1305                1310
---------------------------------------|
```

FIG. 2P

```
Asp Thr Arg Asn Asn Pro Phe Ser Asn Val Asn Ser Thr Met Val Asn
        1315                1320                1325

Asn Lys Ser Glu Cys His Asn Gln Asn Ser Thr Gly His Phe Phe Trp
    1330                1335                1340

Val Asn Val Lys Val Asn Phe Asp Asn Val Ala Met Gly Tyr Leu Ala
1345                1350                1355                1360

Leu Leu Gln Val Ala Thr Phe Lys Gly Trp Met Asp Ile Met Tyr Ala
                1365                1370                1375

Ala Val Asp Ser Gly Glu Ile Asn Ser Gln Pro Asn Trp Glu Asn Asn
            1380                1385                1390
```

FIG. 2Q

```
Leu Tyr Met Tyr Leu Tyr Phe Val Val Phe Ile Ile Phe Gly Gly Phe
        1395                1400                1405
|-----------------------------------IIIS6----------------------

Phe Thr Leu Asn Leu Phe Val Gly Val Ile Ile Asp Asn Phe Asn Gln
    1410                1415                1420
-------------------------------------------|

Gln Lys Lys Lys Leu Gly Gly Gln Asp Ile Phe Met Thr Glu Glu Gln
1425                1430                1435                1440

Lys Lys Tyr Tyr Asn Ala Met Lys Lys Leu Gly Ser Lys Lys Pro Gln
                1445                1450                1455

Lys Pro Ile Pro Arg Pro Leu Asn Lys Tyr Gln Gly Phe Val Phe Asp
            1460                1465                1470
```

FIG. 2R

```
Ile Val Thr Arg Gln Ala Phe Asp Ile Ile Ile Met Val Leu Ile Cys
        1475                1480                1485
|------------------------------------IVS1--------------------

Leu Asn Met Ile Thr Met Met Val Glu Thr Asp Glu Gln Gly Glu Glu
    1490                1495                1500
--------------------------|

Lys Thr Lys Val Leu Gly Arg Ile Asn Gln Phe Phe Val Ala Val Phe
1505                1510                1515                1520
            |-------------------------IVS2--------------------

Thr Gly Glu Cys Val Met Lys Met Phe Ala Leu Arg Gln Tyr Tyr Phe
                1525                1530                1535
------------------------------------------|

Thr Asn Gly Trp Asn Val Phe Asp Phe Ile Val Val Ile Leu Ser Ile
            1540                1545                1550
    |------------------------------------------------IVS3--------
```

FIG. 2S

```
Gly Ser Leu Leu Phe Ser Ala Ile Leu Lys Ser Leu Glu Asn Tyr Phe
        1555                1560                1565
-----------------------------------|

Ser Pro Thr Leu Phe Arg Val Ile Arg Leu Ala Arg Ile Gly Arg Ile
    1570                1575                1580
                    |-------------------------------------IVS4------

Leu Arg Leu Ile Arg Ala Ala Lys Gly Ile Arg Thr Leu Leu Phe Ala
1585                1590                1595                1600
-------------------------------------------|

Leu Met Met Ser Leu Pro Ala Leu Phe Asn Ile Gly Leu Leu Leu Phe
                1605                1610                1615
                                         |----------------------

Leu Val Met Phe Ile Tyr Ser Ile Phe Gly Met Ala Ser Phe Ala Asn
            1620                1625                1630
---------------------------------IVS5---------------------------
```

FIG. 2T

```
Val Val Asp Glu Ala Gly Ile Asp Asp Met Phe Asn Phe Lys Thr Phe
         1635                1640                1645
--|

Gly Asn Ser Met Leu Cys Leu Phe Gln Ile Thr Thr Ser Ala Gly Trp
    1650                1655                1660

Asp Gly Leu Leu Ser Pro Ile Leu Asn Thr Gly Pro Pro Tyr Cys Asp
1665                1670                1675                1680

Pro Asn Leu Pro Asn Ser Asn Gly Ser Arg Gly Asn Cys Gly Ser Pro
                1685                1690                1695

Ala Val Gly Ile Ile Phe Phe Thr Thr Tyr Ile Ile Ile Ser Phe Leu
            1700                1705                1710
          |----------------------------------IVS6----------------
```

FIG. 2U

```
Ile Val Val Asn Met Tyr Ile Ala Val Ile Leu Glu Asn Phe Asn Val
        1715                1720                1725
------------------------------------------|

Ala Thr Glu Glu Ser Thr Glu Pro Leu Ser Glu Asp Asp Phe Asp Met
    1730                1735                1740

Phe Tyr Glu Thr Trp Glu Lys Phe Asp Pro Glu Ala Thr Gln Phe Ile
1745                1750                1755                1760

Ala Phe Ser Ala Leu Ser Asp Phe Ala Asp Thr Leu Ser Gly Pro Leu
                1765                1770                1775

Arg Ile Pro Lys Pro Asn Gln Asn Ile Leu Ile Gln Met Asp Leu Pro
            1780                1785                1790
```

FIG 2V

```
Leu Val Pro Gly Asp Lys Ile His Cys Leu Asp Ile Leu Phe Ala Phe
        1795                1800                1805

Thr Lys Asn Val Leu Gly Glu Ser Gly Glu Leu Asp Ser Leu Lys Thr
    1810                1815                1820

Asn Met Glu Glu Lys Phe Met Ala Thr Asn Leu Ser Lys Ala Ser Tyr
1825                1830                1835                1840

Glu Pro Ile Ala Thr Thr Leu Arg Trp Lys Gln Glu Asp Leu Ser Ala
                1845                1850                1855

Thr Val Ile Gln Lys Ala Tyr Arg Ser Tyr Met Leu His Arg Ser Leu
            1860                1865                1870
```

FIG. 2W

```
Thr Leu Ser Asn Thr Leu His Val Pro Arg Ala Glu Glu Asp Gly Val
        1875                1880                1885

Ser Leu Pro Gly Glu Gly Tyr Val Thr Phe Met Ala Asn Ser Gly Leu
    1890                1895                1900

Pro Asp Lys Ser Glu Thr Ala Ser Ala Thr Ser Phe Pro Pro Ser Tyr
1905                1910                1915                1920

Asp Ser Val Thr Arg Gly Leu Ser Asp Arg Ala Asn Ile Asn Pro Ser
                1925                1930                1935

Ser Ser Met Gln Asn Glu Asp Glu Val Ala Ala Lys Glu Gly Asn Ser
            1940                1945                1950

Pro Gly Pro Gln*
        1955
```

FIG. 2X

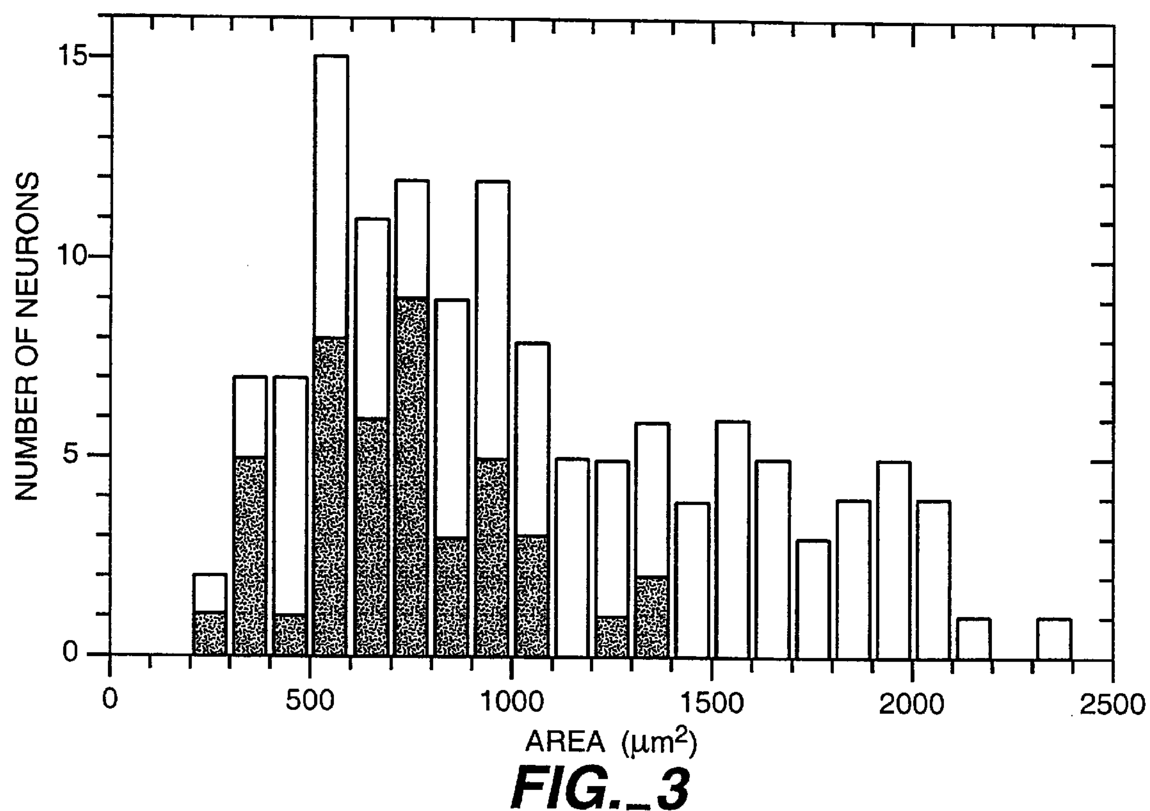
FIG._3
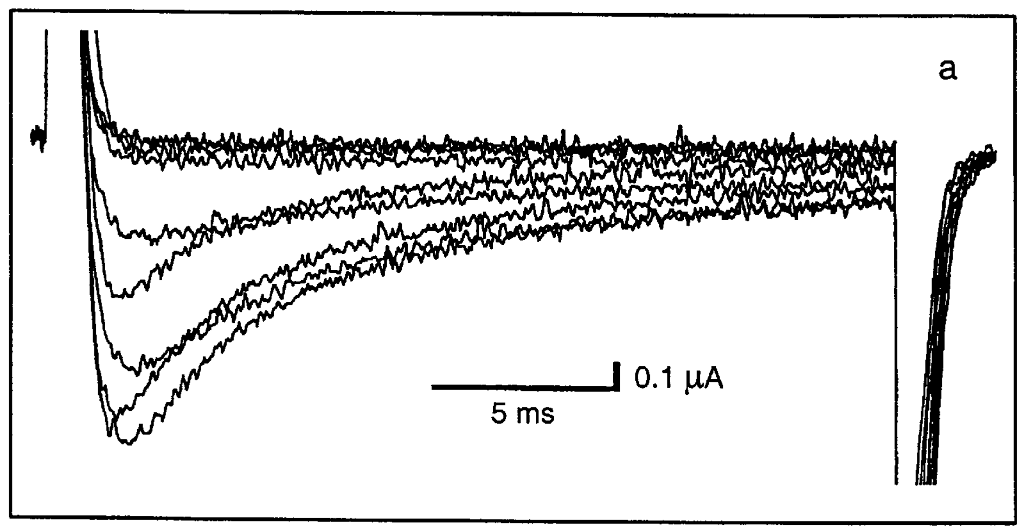
FIG._4A

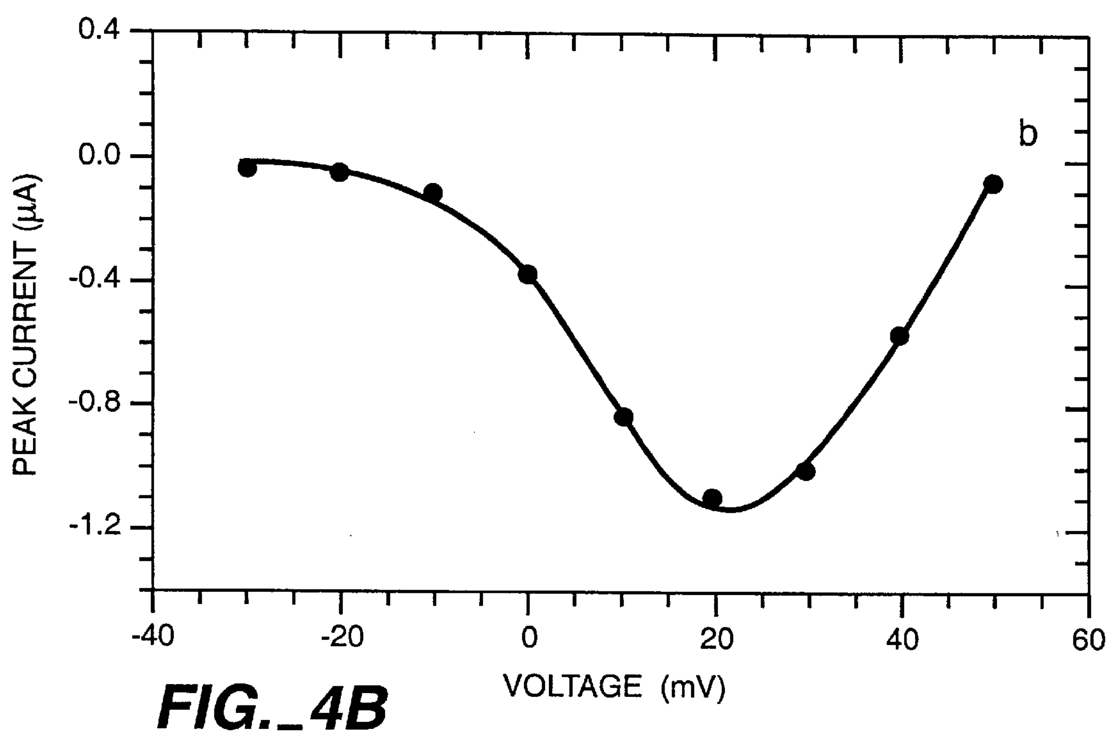
FIG._4B
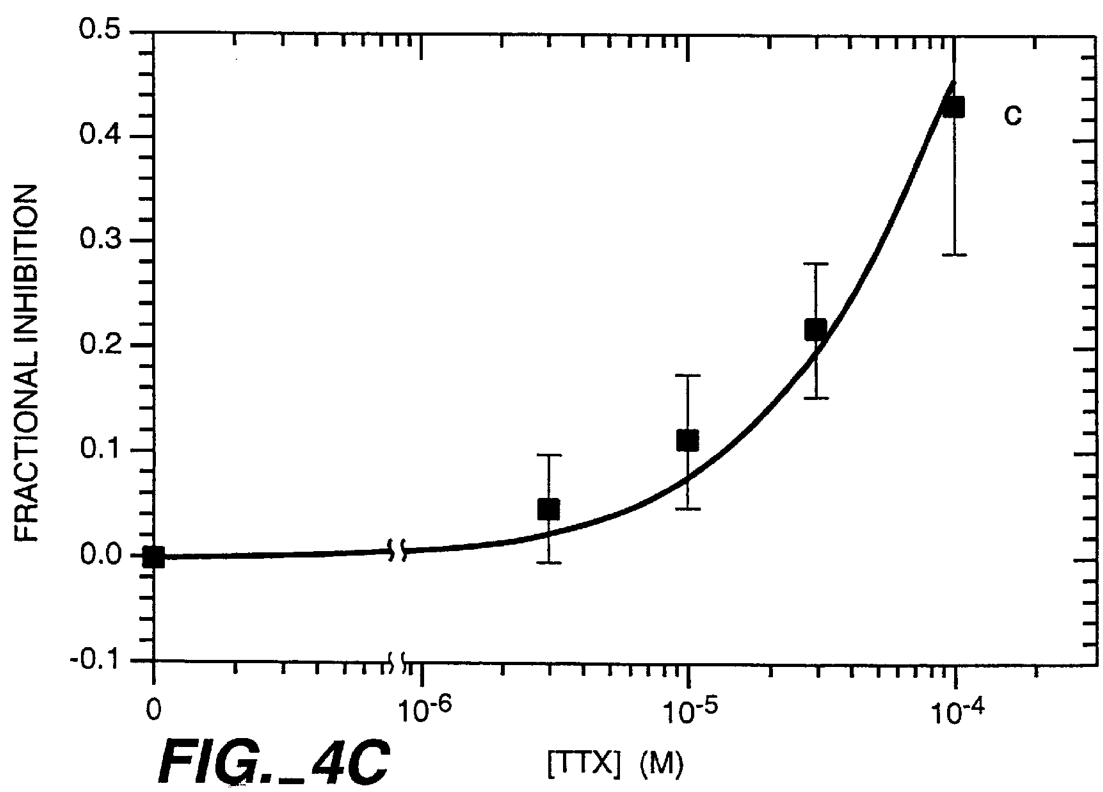
FIG._4C

```
1    ATGGAATTCC CCATTGGATC CCTCGAAACT AACAACTTCC GTCGCTTTAC
51   TCCGGAGTCA CTGGTGGAGA TAGAGAAGCA AATTGCTGCC AAGCAGGGAA
101  CAAAGAAAGC CAGAGAGAAG CATAGGGAGC AGAAGGACCA AGAAGAGAAG
151  CCTCGGCCCC AGCTGGACTT GAAAGCCTGC AACCAGCTGC CCAAGTTCTA
201  TGGTGAGCTC CCAGCAGAAC TGATCGGGGA GCCCCTGGAG GATCTAGATC
251  CGTTCTACAG CACACACCGG ACATTTATGG TGCTGAACAA AGGGAGGACC
301  ATTTCCCGGT TTAGTGCCAC TCGGGCCCTG TGGCTATTCA GTCCTTTCAA
351  CCTGATCAGA AGAACGGCCA TCAAAGTGTC TGTCCACTCG TGGTTCAGTT
401  TATTTATTAC GGTCACTATT TTGGTTAATT GTGTGTGCAT GACCCGAACT
451  GACCTTCCAG AGAAAATTGA ATATGTCTTC ACTGTCATTT ACACCTTTGA
501  AGCCTTGATA AAGATACTGG CAAGAGGATT TTGTCTAAAT GAGTTCACGT
```

FIG. 5A

```
551   ACCTGAGAGA TCCTTGGAAC TGGCTGGATT TTAGCGTCAT TACCCTGGCA
601   TATGTTGGCA CAGCAATAGA TCTCCGTGGG ATCTCAGGCC TGCGGACATT
651   CAGAGTTCTT AGAGCATTAA AAACAGTTTC TGTGATCCCA GGCCTGAAGG
701   TCATTGTGGG GGCCCTGATT CACTCAGTGA AGAAACTGGC TGATGTGACC
751   ATCCTCACCA TCTTCTGCCT AAGTGTTTTT GCCTTGGTGG GGCTGCAACT
801   CTTCAAGGGC AACCTCAAAA ATAAATGTGT CAAGAATGAC ATGGCTGTCA
851   ATGAGACAAC CAACTACTCA TCTCACAGAA AACCAGATAT CTACATAAAT
901   AAGCGAGGCA CTTCTGACCC CTTACTGTGT GGCAATGGAT CTGACTCAGG
951   CCACTGCCCT GATGGTTATA TCTGCCTTAA AACTTCTGAC AACCCGGATT
1001  TTAACTACAC CAGCTTTGAT TCCTTTGCTT GGGCTTTCCT CTCACTGTTC
1051  CGCCTCATGA CACAGGATTC CTGGGAACGC CTCTACCAGC AGACCCTGAG
```

FIG. 5B

```
1101 GACTTCTGGG AAAATCTATA TGATCTTTTT TGTGCTCGTA ATCTTCCTGG
1151 GATCTTTCTA CCTGGTCAAC TTGATCTTGG CTGTAGTCAC CATGGCGTAT
1201 GAGGAGCAGA ACCAGGCAAC CACTGATGAA ATTGAAGCAA AGGAGAAGAA
1251 GTTCCAGGAG GCCCTCGAGA TGCTCCGGAA GGAGCAGGAG GTGCTAGCAG
1301 CACTAGGGAT TGACACAACC TCTCTCCACT CCCACAATGG ATCACCTTTA
1351 ACCTCCAAAA ATGCCAGTGA GAGAAGGCAT AGAATAAAGC CAAGAGTGTC
1401 AGAGGGCTCC ACAGAAGACA ACAAATCACC CCGCTCTGAT CCTTACAACC
1451 AGCGCAGGAT GTCTTTTCTA GGCCTCGCCT CTGGAAAACG CCGGGCTAGT
1501 CATGGCAGTG TGTTCCATTT CCGGTCCCCT GGCCGAGATA TCTCACTCCC
1551 TGAGGGAGTC ACAGATGATG GAGTCTTTCC TGGAGACCAC GAAAGCCATC
1601 GGGGCTCTCT GCTGCTGGGT GGGGGTGCTG GCCAGCAAGG CCCCCTCCCT
```

FIG. 5C

```
1651  AGAAGCCCTC TTCCTCAACC CAGCAACCCT GACTCCAGGC ATGGAGAAGA
1701  TGAACACCAA CCGCCGCCCA CTAGTGAGCT TGCCCCTGGA GCTGTCGATG
1751  TCTCGGCATT CGATGCAGGA CAAAAGAAGA CTTTCTTGTC AGCAGAATAC
1801  TTAGATGAAC CTTTCCGGGC CCAAAGGGCA ATGAGTGTTG TCAGTATCAT
1851  AACCTCCGTC CTTGAGGAAC TCGAGGAGTC TGAACAGAAG TGCCCACCCT
1901  GCTTGACCAG CTTGTCTCAG AAGTATCTGA TCTGGGATTG CTGCCCCATG
1951  TGGGTGAAGC TCAAGACAAT TCTCTTTGGG CTTGTGACGG ATCCCTTTGC
2001  AGAGCTCACC ATCACCTTGT GCATCGTGGT GAACACCATC TTCATGGCCA
2051  TGGAGCACCA TGGCATGAGC CCTACCTTCG AAGCCATGCT CCAGATAGGC
2101  AACATCGTCT TTACCATATT TTTTACTGCT GAAATGGTCT TCAAAATCAT
2151  TGCCTTCGAC CCATACTATT ATTTCCAGAA GAAGTGGAAT ATCTTTGACT
```

FIG. 5D

```
2201  GCATCATCGT CACTGTGAGT CTGCTAGAGC TGGGCGTGGC CAAGAAGGGA
2251  AGCCTGTCTG TGCTGCGGAG CTTCCGCTTG CTGCGCGTAT TCAAGCTGGC
2301  CAAATCCTGG CCCACCTTAA ACACACTCAT CAAGATCATC GGAAACTCAG
2351  TGGGGGCACT GGGGAACCTC ACCATCATCC TGGCCATCAT TGTCTTTGTC
2401  TTTGCTCTGG TTGGCAAGCA GCTCCTAGGG GAAAACTACC GTAACAACCG
2451  AAAAAATATC TCCGCGCCCC ATGAAGACTG GCCCCGCTGG CACATGCACG
2501  ACTTCTTCCA CTCTTTCCTC ATTGTCTTCC GTATCCTCTG TGGAGAGTGG
2551  ATTGAGAACA TGTGGGCCTG CATGGAAGTT GGCCAAAAAT CCATATGCCT
2601  CATCCTTTTC TTGACGGTGA TGGTGCTAGG GAACCTGGTG GTGCTTAACC
2651  TGTTCATCGC CCTGCTATTG AACTCTTTCA GTGCTGACAA CCTCACAGCC
2701  CCGGAGGACG ATGGGGAGGT GAACAACCTG CAGGTGGCCC TGGCACGGAT
```

FIG. 5E

```
2751  CCAGGTCTTT GGCCATCGTA CCAAACAGGC TCTTTGCAGC TTCTTCAGCA
2801  GGTCCTGCCC ATTCCCCCAG CCCAAGGCAG AGCCTGAGCT GGTGGTGAAA
2851  CTCCCACTCT CCAGCTCCAA GGCTGAGAAC CACATTGCTG CCAACACTGC
2901  CAGGGGGAGC TCTGGAGGGC TCCAAGCTCC CAGAGGCCCC AGGGATGAGC
2951  ACAGTGACTT CATCGCTAAT CCGACTGTGT GGGTCTCTGT GCCCATTGCT
3001  GAGGGTGAAT CTGATCTTGA TGACTTGGAG GATGATGGTG GGGAAGATGC
3051  TCAGAGCTTC CAGCAGGAAG TGATCCCCAA AGGACAGCAG GAGCAGCTGC
3101  AGCAAGTCGA GAGGTGTGGG GACCACCTGA CACCCAGGAG CCCAGGCACT
3151  GGAACATCTT CTGAGGACCT GGCTCCATCC CTGGGTGAGA CGTGGAAAGA
3201  TGAGTCTGTT CCTCAGGCCC CTGCTGAGGG AGTGGACGAC ACAAGCTCCT
3251  CTGAGGGCAG CACGGTGGAC TGCCTAGATC CTGAGGAAAT CCTGAGGAAG
```

FIG. 5F

```
3301  ATCCCTGAGC TGGCAGATGA CCTGGAAGAA CCAGATGACT GCTTCACAGA
3351  AGGATGCATT CGCCACTGTC CCTGCTGCAA ACTGGATACC ACCAAGAGTC
3401  CATGGGATGT GGGCTGGCAG GTGCGCAAGA CTTGCTACCG TATCGTGGAG
3451  CACAGCTGGT TTGAGAGCTT CATCATCTTC ATGATCCTGC TCAGCAGTGG
3501  ATCTCTGGCC TTTGAAGACT ATTACCTGGA CCAGAAGCCC ACGGTGAAAG
3551  CTTTGCTGGA GTACACTGAC AGGGTCTTCA CCTTTATCTT TGTGTTCGAG
3601  ATGCTGCTTA AGTGGGTGGC CTATGGCTTC AAAAAGTACT TCACCAATGC
3651  CTGGTGCTGG CTGGACTTCC TCATTGTGAA TATCTCACTG ATAAGTCTCA
3701  CAGCGAAGAT TCTGGAATAT TCTGAAGTGG CTCCCATCAA AGCCCTTCGA
3751  ACCCTTCGCG CTCTGCGGCC ACTGCGGGCT CTTTCTCGAT TTGAAGGCAT
3801  GCGGGTGGTG GTGGATGCCC TGGTGGGCGC CATCCCATCC ATCATGAATG
```

FIG. 5G

```
3851  TCCTCCTCGT CTGCCTCATC TTCTGGCTCA TCTTCAGCAT CATGGGTGTG
3901  AACCTCTTCG CAGGGAAGTT TTGGAGGTGC ATCAACTATA CCGATGGAGA
3951  GTTTTCCCTT GTACCTTTGT CGATTGtGAA TAACAAGTCT GACTGCAAGA
4001  TTCAAAACTC CACTGGCAGC TTCTTCTGGG TCAATGTGAA AGTCAACTTT
4051  GATAATGTTG CAATGGGTTA CCTTGCACTT CTGCAGGTGG CAACCTTTAA
4101  AGGCTGGATG GACATTATGT ATGCAGCTGT TGATTCCCGG GAGGTCAACA
4151  TGCAACCCAA GTGGGAGGAC AACGTGTACA TGTATTTGTA CTTTGTCATC
4201  TTCATCATTT TTGGAGGCTT CTTCACACTG AATCTCTTTG TTGGGGTCAT
4251  AATTGACAAC TTCAATCAAC AGAAAAAAAA GTTAGGGGGC CAGGACATCT
4301  TCATGACAGA GGAGCAGAAG AAATACTACA ATGCCATGAA GAAGTTGGGC
4351  TCCAAGAAGC CCCAGAAGCC CATCCCACGG CCCCTGAACA AGTTCCAGGG
```

FIG. 5H

```
4401  TTTTGTCTTT GACATCGTGA CCAGACAAGC TTTTGACATC ACCATCATGG
4451  TCCTCATCTG CCTCAACATG ATCACCATGA TGGTGGAGAC TGATGACCAA
4501  AGTGAAGAAA AGACGAAAAT TCTGGGCAAA ATCAACCAGT TCTTTGTGGC
4551  CGTCTTCACA GGCGAATGTG TCATGAAGAT GTTCGCTTTG AGGCAGTACT
4601  ACTTCACAAA TGGCTGGAAT GTGTTTGACT TCATTGTGGT GGTTCTCTCC
4651  ATTGCGAGCC TGATTTTTTC TGCAATTCTT AAGTCACTTC AAAGTTACTT
4701  CTCCCCAACG CTCTTCAGAG TCATCCGCCT GGCCCGAATT GGCCGCATCC
4751  TCAGACTGAT CCGAGCGGCC AAGGGGATCC GCACACTGCT CTTTGCCCTC
4801  ATGATGTCCC TGCCTGCCCT CTTCAACATC GGGCTGTTGC TATTCCTTGT
4851  CATGTTCATC TACTCCATCT TCGGTATGTC CAGCTTTCCC CATGTGAGGT
4901  GGGAGGCTGG CATCGACGAC ATGTTCAACT TCCAGACCTT CGCCAACAGC
```

FIG. 5I

```
4951  ATGCTGTGCC TCTTCCAGAT TACCACGTCG GCCGGCTGGG ATGGCCTCCT
5001  CAGCCCCATC CTCAACACAG GGCCCCCCTA CTGTGACCCC AATCTGCCCA
5051  ACAGCAATGG CACCAGAGGG GACTGTGGGA GCCCAGCCGT AGGCATCATC
5101  TTCTTCACCA CCTACATCAT CATCTCCTTC CTCATCGTGG TCAACATGTA
5151  CATTGCAGTG ATTCTGGAGA ACTTCAATGT GGCCACGGAG GAGAGCACTG
5201  AGCCCCTGAG TGAGGACGAC TTTGACATGT TCTATGAGAC CTGGGAGAAG
5251  TTTGACCCAG AGGCCACTCA GTTTATTACC TTTTCTGCTC TCTCGGACTT
5301  TGCAGACACT CTCTCTGGTC CCCTGAGAAT CCCAAAACCC AATCGAAATA
5351  TACTGATCCA GATGGACCTG CCTTTGGTCC CTGGAGATAA GATCCACTGC
5401  TTGGACATCC TTTTTGCTTT CACCAAGAAT GTCCTAGGAG AATCCGGGGA
5451  GTTGGATTCT CTGAAGGCAA ATATGGAGGA GAAGTTTATG GCAACTAATC
```

FIG. 5J

```
5501  TTTCAAAATC ATCCTATGAA CCAATAGCAA CCACTCTCCG ATGGAAGCAA
5551  GAAGACATTT CAGCCACTGT CATTCAAAAG GCCTATCGGA GCTATGTGCT
5601  GCACCGCTCC ATGGCACTCT CTAACACCCC ATGTGTGCCC AGAGCTGAGG
5651  AGGAGGCTGC ATCACTCCCA GATGAAGGTT TTGTTGCATT CACAGCAAAT
5701  GAAAATTGTG TACTCCCAGA CAAATCTGAA ACTGCTTCTG CCACATCATT
5751  CCCACCGTCC TATGAGAGTG TCACTAGAGG CCTTAGTGAT AGAGTCAACA
5801  TGAGGACATC TAGCTCAATA CAAAATGAAG ATGAAGCCAC CAGTATGGAG
5851  CTGATTGCCC CTGGGCCCTA GTGA
```

FIG. 5K

1 Met Glu Phe Pro Ile Gly Ser Leu Glu Thr Asn Asn Phe Arg Arg

16 Phe Thr Pro Glu Ser Leu Val Glu Ile Glu Lys Gln Ile Ala Ala

31 Lys Gln Gly Thr Lys Lys Ala Arg Glu Lys His Arg Glu Gln Lys

46 Asp Gln Glu Glu Lys Pro Arg Pro Gln Leu Asp Leu Lys Ala Cys

61 Asn Gln Leu Pro Lys Phe Tyr Gly Glu Leu Pro Ala Glu Leu Ile

76 Gly Glu Pro Leu Glu Asp Leu Asp Pro Phe Tyr Ser Thr His Arg

91 Thr Phe Met Val Leu Asn Lys Gly Arg Thr Ile Ser Arg Phe Ser

106 Ala Thr Arg Ala Leu Trp Leu Phe Ser Pro Phe Asn Leu Ile Arg

121 Arg Thr Ala Ile Lys Val Ser Val His Ser Trp Phe Ser Leu Phe

136 Ile Thr Val Thr Ile Leu Val Asn Cys Val Cys Met Thr Arg Thr

151 Asp Leu Pro Glu Lys Ile Glu Tyr Val Phe Thr Val Ile Tyr Thr

166 Phe Glu Ala Leu Ile Lys Ile Leu Ala Arg Gly Phe Cys Leu Asn

181 Glu Phe Thr Tyr Leu Arg Asp Pro Trp Asn Trp Leu Asp Phe Ser

FIG. 6A

196 Val Ile Thr Leu Ala Tyr Val Gly Thr Ala Ile Asp Leu Arg Gly

211 Ile Ser Gly Leu Arg Thr Phe Arg Val Leu Arg Ala Leu Lys Thr

226 Val Ser Val Ile Pro Gly Leu Lys Val Ile Val Gly Ala Leu Ile

241 His Ser Val Lys Lys Leu Ala Asp Val Thr Ile Leu Thr Ile Phe

256 Cys Leu Ser Val Phe Ala Leu Val Gly Leu Gln Leu Phe Lys Gly

271 Asn Leu Lys Asn Lys Cys Val Lys Asn Asp Met Ala Val Asn Glu

286 Thr Thr Asn Tyr Ser Ser His Arg Lys Pro Asp Ile Tyr Ile Asn

301 Lys Arg Gly Thr Ser Asp Pro Leu Leu Cys Gly Asn Gly Ser Asp

316 Ser Gly His Cys Pro Asp Gly Tyr Ile Cys Leu Lys Thr Ser Asp

331 Asn Pro Asp Phe Asn Tyr Thr Ser Phe Asp Ser Phe Ala Trp Ala

346 Phe Leu Ser Leu Phe Arg Leu Met Thr Gln Asp Ser Trp Glu Arg

361 Leu Tyr Gln Gln Thr Leu Arg Thr Ser Gly Lys Ile Tyr Met Ile

376 Phe Phe Val Leu Val Ile Phe Leu Gly Ser Phe Tyr Leu Val Asn

FIG. 6B

391 Leu Ile Leu Ala Val Val Thr Met Ala Tyr Glu Glu Gln Asn Gln

406 Ala Thr Thr Asp Glu Ile Glu Ala Lys Glu Lys Lys Phe Gln Glu

421 Ala Leu Glu Met Leu Arg Lys Glu Gln Glu Val Leu Ala Ala Leu

436 Gly Ile Asp Thr Thr Ser Leu His Ser His Asn Gly Ser Pro Leu

451 Thr Ser Lys Asn Ala Ser Glu Arg Arg His Arg Ile Lys Pro Arg

466 Val Ser Glu Gly Ser Thr Glu Asp Asn Lys Ser Pro Arg Ser Asp

481 Pro Tyr Asn Gln Arg Arg Met Ser Phe Leu Gly Leu Ala Ser Gly

496 Lys Arg Arg Ala Ser His Gly Ser Val Phe His Phe Arg Ser Pro

511 Gly Arg Asp Ile Ser Leu Pro Glu Gly Val Thr Asp Asp Gly Val

526 Phe Pro Gly Asp His Glu Ser His Arg Gly Ser Leu Leu Leu Gly

541 Gly Gly Ala Gly Gln Gln Gly Pro Leu Pro Arg Ser Pro Leu Pro

556 Gln Pro Ser Asn Pro Asp Ser Arg His Gly Glu Asp Glu His Gln

FIG. 6C

571 Pro Pro Pro Thr Ser Glu Leu Ala Pro Gly Ala Val Asp Val Ser

586 Ala Phe Asp Ala Gly Gln Lys Lys Thr Phe Leu Ser Ala Glu Tyr

601 Leu Asp Glu Pro Phe Arg Ala Gln Arg Ala Met Ser Val Val Ser

616 Ile Ile Thr Ser Val Leu Glu Glu Leu Glu Glu Ser Glu Gln Lys

631 Cys Pro Pro Cys Leu Thr Ser Leu Ser Gln Lys Tyr Leu Ile Trp

646 Asp Cys Cys Pro Met Trp Val Lys Leu Lys Thr Ile Leu Phe Gly

661 Leu Val Thr Asp Pro Phe Ala Glu Leu Thr Ile Thr Leu Cys Ile

676 Val Val Asn Thr Ile Phe Met Ala Met Glu His His Gly Met Ser

691 Pro Thr Phe Glu Ala Met Leu Gln Ile Gly Asn Ile Val Phe Thr

706 Ile Phe Phe Thr Ala Glu Met Val Phe Lys Ile Ile Ala Phe Asp

721 Pro Tyr Tyr Tyr Phe Gln Lys Lys Trp Asn Ile Phe Asp Cys Ile

736 Ile Val Thr Val Ser Leu Leu Glu Leu Gly Val Ala Lys Lys Gly

751 Ser Leu Ser Val Leu Arg Ser Phe Arg Leu Leu Arg Val Phe Lys

FIG. 6D

766 Leu Ala Lys Ser Trp Pro Thr Leu Asn Thr Leu Ile Lys Ile Ile

781 Gly Asn Ser Val Gly Ala Leu Gly Asn Leu Thr Ile Ile Leu Ala

796 Ile Ile Val Phe Val Phe Ala Leu Val Gly Lys Gln Leu Leu Gly

811 Glu Asn Tyr Arg Asn Asn Arg Lys Asn Ile Ser Ala Pro His Glu

826 Asp Trp Pro Arg Trp His Met His Asp Phe Phe His Ser Phe Leu

841 Ile Val Phe Arg Ile Leu Cys Gly Glu Trp Ile Glu Asn Met Trp

856 Ala Cys Met Glu Val Gly Gln Lys Ser Ile Cys Leu Ile Leu Phe

871 Leu Thr Val Met Val Leu Gly Asn Leu Val Val Leu Asn Leu Phe

886 Ile Ala Leu Leu Leu Asn Ser Phe Ser Ala Asp Asn Leu Thr Ala

901 Pro Glu Asp Asp Gly Glu Val Asn Asn Leu Gln Val Ala Leu Ala

916 Arg Ile Gln Val Phe Gly His Arg Thr Lys Gln Ala Leu Cys Ser

931 Phe Phe Ser Arg Ser Cys Pro Phe Pro Gln Pro Lys Ala Glu Pro

946 Glu Leu Val Val Lys Leu Pro Leu Ser Ser Ser Lys Ala Glu Asn

FIG. 6E

961 His Ile Ala Ala Asn Thr Ala Arg Gly Ser Ser Gly Gly Leu Gln

976 Ala Pro Arg Gly Pro Arg Asp Glu His Ser Asp Phe Ile Ala Asn

991 Pro Thr Val Trp Val Ser Val Pro Ile Ala Glu Gly Glu Ser Asp

1006 Leu Asp Asp Leu Glu Asp Asp Gly Gly Glu Asp Ala Gln Ser Phe

1021 Gln Gln Glu Val Ile Pro Lys Gly Gln Gln Glu Gln Leu Gln Gln

1036 Val Glu Arg Cys Gly Asp His Leu Thr Pro Arg Ser Pro Gly Thr

1051 Gly Thr Ser Ser Glu Asp Leu Ala Pro Ser Leu Gly Glu Thr Trp

1066 Lys Asp Glu Ser Val Pro Gln Ala Pro Ala Glu Gly Val Asp Asp

1081 Thr Ser Ser Ser Glu Gly Ser Thr Val Asp Cys Leu Asp Pro Glu

1096 Glu Ile Leu Arg Lys Ile Pro Glu Leu Ala Asp Asp Leu Glu Glu

1111 Pro Asp Asp Cys Phe Thr Glu Gly Cys Ile Arg His Cys Pro Cys

1126 Cys Lys Leu Asp Thr Thr Lys Ser Pro Trp Asp Val Gly Trp Gln

1141 Val Arg Lys Thr Cys Tyr Arg Ile Val Glu His Ser Trp Phe Glu

FIG. 6F

1156 Ser Phe Ile Ile Phe Met Ile Leu Leu Ser Ser Gly Ser Leu Ala

1171 Phe Glu Asp Tyr Tyr Leu Asp Gln Lys Pro Thr Val Lys Ala Leu

1186 Leu Glu Tyr Thr Asp Arg Val Phe Thr Phe Ile Phe Val Phe Glu

1201 Met Leu Leu Lys Trp Val Ala Tyr Gly Phe Lys Lys Tyr Phe Thr

1216 Asn Ala Trp Cys Trp Leu Asp Phe Leu Ile Val Asn Ile Ser Leu

1231 Ile Ser Leu Thr Ala Lys Ile Leu Glu Tyr Ser Glu Val Ala Pro

1246 Ile Lys Ala Leu Arg Thr Leu Arg Ala Leu Arg Pro Leu Arg Ala

1261 Leu Ser Arg Phe Glu Gly Met Arg Val Val Val Asp Ala Leu Val

1276 Gly Ala Ile Pro Ser Ile Met Asn Val Leu Leu Val Cys Leu Ile

1291 Phe Trp Leu Ile Phe Ser Ile Met Gly Val Asn Leu Phe Ala Gly

1306 Lys Phe Trp Arg Cys Ile Asn Tyr Thr Asp Gly Glu Phe Ser Leu

1321 Val Pro Leu Ser Ile Val Asn Asn Lys Ser Asp Cys Lys Ile Gln

1336 Asn Ser Thr Gly Ser Phe Phe Trp Val Asn Val Lys Val Asn Phe

FIG. 6G

1351 Asp Asn Val Ala Met Gly Tyr Leu Ala Leu Leu Gln Val Ala Thr

1366 Phe Lys Gly Trp Met Asp Ile Met Tyr Ala Ala Val Asp Ser Arg

1381 Glu Val Asn Met Gln Pro Lys Trp Glu Asp Asn Val Tyr Met Tyr

1396 Leu Tyr Phe Val Ile Phe Ile Ile Phe Gly Gly Phe Phe Thr Leu

1411 Asn Leu Phe Val Gly Val Ile Ile Asp Asn Phe Asn Gln Gln Lys

1426 Lys Lys Leu Gly Gly Gln Asp Ile Phe Met Thr Glu Glu Gln Lys

1441 Lys Tyr Tyr Asn Ala Met Lys Lys Leu Gly Ser Lys Lys Pro Gln

1456 Lys Pro Ile Pro Arg Pro Leu Asn Lys Phe Gln Gly Phe Val Phe

1471 Asp Ile Val Thr Arg Gln Ala Phe Asp Ile Thr Ile Met Val Leu

1486 Ile Cys Leu Asn Met Ile Thr Met Met Val Glu Thr Asp Asp Gln

1501 Ser Glu Glu Lys Thr Lys Ile Leu Gly Lys Ile Asn Gln Phe Phe

1516 Val Ala Val Phe Thr Gly Glu Cys Val Met Lys Met Phe Ala Leu

1531 Arg Gln Tyr Tyr Phe Thr Asn Gly Trp Asn Val Phe Asp Phe Ile

FIG. 6H

1546 Val Val Val Leu Ser Ile Ala Ser Leu Ile Phe Ser Ala Ile Leu

1561 Lys Ser Leu Gln Ser Tyr Phe Ser Pro Thr Leu Phe Arg Val Ile

1576 Arg Leu Ala Arg Ile Gly Arg Ile Leu Arg Leu Ile Arg Ala Ala

1591 Lys Gly Ile Arg Thr Leu Leu Phe Ala Leu Met Met Ser Leu Pro

1606 Ala Leu Phe Asn Ile Gly Leu Leu Leu Phe Leu Val Met Phe Ile

1621 Tyr Ser Ile Phe Gly Met Ser Ser Phe Pro His Val Arg Trp Glu

1636 Ala Gly Ile Asp Asp Met Phe Asn Phe Gln Thr Phe Ala Asn Ser

1651 Met Leu Cys Leu Phe Gln Ile Thr Thr Ser Ala Gly Trp Asp Gly

1666 Leu Leu Ser Pro Ile Leu Asn Thr Gly Pro Pro Tyr Cys Asp Pro

1681 Asn Leu Pro Asn Ser Asn Gly Thr Arg Gly Asp Cys Gly Ser Pro

1696 Ala Val Gly Ile Ile Phe Phe Thr Thr Tyr Ile Ile Ile Ser Phe

1711 Leu Ile Val Val Asn Met Tyr Ile Ala Val Ile Leu Glu Asn Phe

1726 Asn Val Ala Thr Glu Glu Ser Thr Glu Pro Leu Ser Glu Asp Asp

FIG. 6I

1741 Phe Asp Met Phe Tyr Glu Thr Trp Glu Lys Phe Asp Pro Glu Ala

1756 Thr Gln Phe Ile Thr Phe Ser Ala Leu Ser Asp Phe Ala Asp Thr

1771 Leu Ser Gly Pro Leu Arg Ile Pro Lys Pro Asn Arg Asn Ile Leu

1786 Ile Gln Met Asp Leu Pro Leu Val Pro Gly Asp Lys Ile His Cys

1801 Leu Asp Ile Leu Phe Ala Phe Thr Lys Asn Val Leu Gly Glu Ser

1816 Gly Glu Leu Asp Ser Leu Lys Ala Asn Met Glu Glu Lys Phe Met

1831 Ala Thr Asn Leu Ser Lys Ser Ser Tyr Glu Pro Ile Ala Thr Thr

1846 Leu Arg Trp Lys Gln Glu Asp Ile Ser Ala Thr Val Ile Gln Lys

1861 Ala Tyr Arg Ser Tyr Val Leu His Arg Ser Met Ala Leu Ser Asn

1876 Thr Pro Cys Val Pro Arg Ala Glu Glu Glu Ala Ala Ser Leu Pro

1891 Asp Glu Gly Phe Val Ala Phe Thr Ala Asn Glu Asn Cys Val Leu

1906 Pro Asp Lys Ser Glu Thr Ala Ser Ala Thr Ser Phe Pro Pro Ser

1921 Tyr Glu Ser Val Thr Arg Gly Leu Ser Asp Arg Val Asn Met Arg

FIG. 6J

1936 Thr Ser Ser Ser Ile Gln Asn Glu Asp Glu Ala Thr Ser Met Glu

1951 Leu Ile Ala Pro Gly Pro

FIG. 6K

HUMAN PERIPHERAL NERVE, TETRODOTOXIN-RESISTANT SODIUM CHANNEL α-SUBUNIT POLYPEPTIDE

CROSS REFERENCES TO RELATED APPLICATION

This application is a divisional of U.S. Ser. No. 08/843,417, filed on Apr. 15, 1997, now U.S. Pat. No. 6,184,349 which is a continuation-in-part of U.S. Ser. No. 08/511,828, filed Oct. 11, 1995, now abandoned, both of which are incorporated by reference herein.

BACKGROUND OF THE INVENTION

1. Field of the Invention

The basic unit of information transmitted from one part of the nervous system to another is a single action potential or nerve impulse. The "transmission line" for these impulses is the axon, or nerve fiber. The electrical excitability of the nerve membrane has been shown to depend on the membrane's voltage-sensitive ionic permeability system that allows it to use energy stored in ionic concentration gradients. Electrical activity of the nerve is triggered by a depolarization of the membrane, which opens channels through the membrane that are highly selective for sodium ions, which are then driven inward by the electrochemical gradient. Of the many ionic channels, the voltage-gated or voltage-sensitive sodium channel is one of the most studied. It is a transmembrane protein that is essential for the generation of action potentials in excitable cells.

The cDNAs for several $Na^+$ channels have been cloned and sequenced. These studies have shown that the amino acid sequence of the $Na^+$ channel has been conserved over a long evolutionary period. These studies have also revealed that the channel is a single polypeptide containing four internal repeats, or homologous domains (domains I–IV), having similar amino acid sequences. Each domain folds into six predicted transmembrane α-helices or segments: five are hydrophobic segments and one is highly charged with many lysine and arginine residues. This highly charged segment is the fourth transmembrane segment in each domain (the S4 segment) and is likely to be involved in voltage-gating. The positively charged side chains on the S4 segment are likely to be paired with the negatively charged side chains on the other five segments such that membrane depolarization could shift the position of one helix relative to the other, thereby opening the channel. Accessory subunits may modify the function of the channel.

There is a significant therapeutic utility in recombinant materials derived from the DNA of the numerous sodium channels that have been discovered. For example, the recombinant protein can be used to screen for potential therapeutics that have the ability to inhibit the sodium channel of interest. In particular, it would be useful to inhibit selectively the function of sodium channels in nerve tissues responsible for transmitting pain and pressure signals without simultaneously affecting the function of sodium channels in other tissues such as muscle, heart and brain. Such selectivity would allow for the treatment of pain without causing side effects due to cardiac, central nervous system or neuromuscular complications. Therefore, it would be useful to have DNA sequences coding for sodium channels that are selectively expressed in peripheral sensory nerve tissue. Though cDNAs from rat skeletal muscle, heart and brain are known, identification and isolation of cDNA from peripheral sensory nerve tissue, such as dorsal root ganglia, has been hampered by the difficulty of working with such tissue.

This invention relates to a cloned α-subunit of a voltage-gated tetrodotoxin-resistant sodium channel protein expressed in peripheral nerve tissue. This invention further relates to its production by recombinant technology and nucleic acid sequences encoding for this protein.

2. Summary of Related Art

An excellent review of sodium channels is presented in Catterall, *TINS* 16(12):500–506 (1993).

Purified $Na^+$ channels have proven useful as therapeutic and diagnostic tools, Cherksey, U.S. Pat. No. 5,132,296.

The cDNAs for several $Na^+$ channels have been cloned and sequenced. Numa, et al., *Annals of the New York Academy of Sciences* 479:338–355 (1986), describes cDNA from the electric organ of eel and two different ones from rat brain. Rogart, U.S. Pat. No. 5,380,836 describes cDNA from rat cardiac tissue. See also Rogart, Cribbs et al. *Proc. Natl. Acad., Sci.*, 86:8170–8174 (1989). A peripheral nerve sodium channel, referred to as PN1, has been detected based on sodium current studies and hybridization to a highly conserved sodium channel probe by D'Arcangelo, et al., *J. Cell Biol.* 122:915–921 (1993). However, neither the DNA nor the protein were isolated and its complete nucleic acid and amino acid sequence remained unidentified. A partial amino acid sequence was presented at the 23rd Annual Meeting of the Society for Neuroscience, Nov. 7–12, 1993, Washington D.C., see Abstracts: Volume 19, Part 1: Abstract 121.7: "Nerve Growth Factor Treatment of PC12 Cells Induces the Expression of a Novel Sodium Channel Gene, Peripheral Nerve Type 1 (PN1)", by B. L. Moss, J. Toledo-Aral and G. Mandel.

Tetrodotoxin ("TTX"), a highly potent toxin from the puffer or Fugu fish, blocks the conduction of nerve impulses along axons and in excitable membranes of nerve fibers, which leads to respiratory paralysis. TTX also binds very tightly to the $Na^+$ channel and blocks the flow of sodium ions. The positively charged group of the toxin interacts with a negatively charged carboxylate at the mouth of the channel on the extracellular side of the membrane, thus obstructing the conductance pathway.

Studies using TTX as a probe have shed much light on the mechanism and structure of $Na^+$ channels. There are three $Na^+$ channel subtypes, defined by the affinity for TTX which can be measured by the $IC_{50}$ values: TTX-sensitive $Na^+$ channels ($IC_{50}\approx 1$ nM), TTX-insensitive $Na^+$ channels ($IC_{50}=1$–$5$ $\mu$M), and TTX-resistant $Na^+$ channels ($IC_{50}\geqq 100$ $\mu$M)

TTX-insensitive action potentials were first studied in rat skeletal muscle. Redfern, et al., Acta Physiol. Scand. 82:70–78 (1971). Subsequently, these action potentials were described in other mammalian tissues, including newborn mammalian skeletal muscle, mammalian cardiac muscle, mouse dorsal root ganglion cells in vitro and in culture, cultured mammalian skeletal muscle and L6 cells. Rogart, *Ann. Rev. Physiol.* 43:711–725 (1980).

Dorsal root ganglia neurons possess both TTX-sensitive ($IC_{50}\cong 0.3$ nM) and TTX-resistant ($IC_{50}\cong 100$ $\mu$M) sodium channel currents, as described in Roy, et al., *J. Neurosci.* 12:2104–2111 (1992).

TTX-resistant sodium currents have also been measured in rat nodose and petrosal ganglia, Ikeda, et al., *J. Neurophysiol.* 55:527–539 (1986) and Stea, et al., Neurosci. 47:727–736 (1992).

SUMMARY OF THE INVENTION

One aspect of the present invention is a purified and isolated DNA sequence encoding for a mammalian peripheral nerve sodium channel protein, in particular, the α-subunit of this protein. A preferred embodiment of the invention is a purified and isolated DNA sequence encoding a mammalian peripheral nerve TTX-resistant sodium channel.

Further aspects of the invention include expression vectors comprising the DNA of the invention, host cells transformed or transfected by these vectors, specifically mammalian cells, and a cDNA library of these host cells.

Another aspect of the present invention is a recombinant polynucleotide comprising a nucleic acid sequence derived from the DNA sequence of this invention.

Still another aspect of the invention is the rat and human peripheral nerve TTX-resistant sodium channel protein encoded by the DNA of this invention.

Also forming part of this invention is an assay for inhibitors of the peripheral nerve TTX-resistant sodium channel protein comprising contacting a compound suspected of being an inhibitor with expressed sodium channel and measuring the activity of the sodium channel.

Further provided is a method of inhibiting the activity of the peripheral nerve TTX-resistant sodium channel comprising administering an effective amount of a compound having an $IC_{50}$ of 10 $\mu$M or less.

BRIEF DESCRIPTION OF THE DRAWINGS

FIGS. 1A–1I depict the 6344 nucleotide cDNA sequence encoding the rat peripheral nerve sodium channel type 3 ("PN3") comprising a 5868-base open reading frame (SEQ ID NO:1). Nucleotide residue 23 represents the start site of translation and residue 5893 represents the end of the stop codon.

FIGS. 2A–2X depict the deduced amino acid sequence of PN3 (SEQ ID NO:2). Also shown are the homologous domains (I–IV); the putative transmembrane segments (SI–S6); potential cAMP-dependent phosphorylation sites (○); potential N-linked glycosylation sites (●); the TTX resistance site (♦); the termination codon (*); and the site where several partial PN3 clones contained an additional Gln between $Pro^{584}$ and $Ala^{585}$ (↑).

FIG. 3 depicts a frequency histogram of somal area of DRG cells analyzed by in situ hybridization with a PN3 probe.

FIGS. 4A–4C show the properties of currents induced in Xenopus oocytes by injection of PN3 cRNA.

FIGS. 5A–5K depict the 5874 nucleotide open reading frame DNA sequence, assembled from cDNA and PCR fragments, encoding the human peripheral nerve sodium channel type 3 ("hPN3")(SEQ ID NO:9).

FIGS. 6A–6K depict the deduced amino acid sequence of hPN3 (SEQ ID NO:10).

DETAILED DESCRIPTION OF THE INVENTION

The present invention relates to sodium channel proteins present in peripheral nerve tissue. Specific embodiments include such sodium channels that are TTX-resistant and are expressed exclusively in sensory neurons. Degenerate oligonucleotide-primed RT-PCR analysis was performed on RNA from the rat central and peripheral nervous systems, in particular from rat dorsal root ganglia ("DRG"). The α-subunit of a voltage-gated, TTX-resistant sodium channel from rat DRG has been cloned and functionally expressed in Xenopus oocytes.

In particular, the present invention relates to a purified and isolated DNA sequence encoding for a rat peripheral nerve TTX-resistant sodium channel. The term "purified and isolated DNA" refers to DNA that is essentially free, i.e. contains less than about 30%, preferably less than about 10%, and even more preferably less than about 1% of the DNA with which the DNA of interest is naturally associated. Techniques for assessing purity are well known to the art and include, for example, restriction mapping, agarose gel electrophoresis, and CsCl gradient centrifugation. The term "DNA" is meant to include cDNA made by reverse transcription of mRNA or by chemical synthesis.

Specifically, the invention relates to DNA having the nucleotide sequence set forth in FIG. 1 (SEQ ID NO:1). More generally, the DNA sequence comprises a cDNA sequence that encodes the α-subunit of a voltage-gated TTX-resistant sodium channel, specifically the amino acid sequence set forth in FIG. 2 (SEQ ID NO: 2). DNA sequences encoding the same or allelic variant or analog sodium channel protein polypeptides of the peripheral nervous system, through use of, at least in part, of degenerate codons are also contemplated by this invention. The DNA sequence of FIG. 1 corresponds to the cDNA from rat. However, it is believed that a voltage-gated TTX-resistant sodium channel is also expressed in peripheral nerve tissue of other mammalian species such as humans, and that the corresponding gene is highly homologous to the rat sequence. Therefore, the invention includes cDNA encoding a mammalian voltage-gated, TTX-resistant sodium channel.

The present invention also relates to a purified and isolated DNA sequence encoding a human peripheral nerve TTX-resistant sodium channel. Specifically, the invention includes DNA having the nucleotide sequence set forth in FIG. 5 (SEQ ID NO: 9), which sets forth the human PN3, assembled from cDNA and PCR fragments. More generally, the DNA sequence comprises a sequence that encodes the α-subunit of a voltage-gated TTX-resistant sodium channel, specifically the amino acid sequence set forth in FIG. 6 (SEQ ID NO: 10).

The 1956-amino acid protein encoded by the cDNA of the invention is designated herein as peripheral nerve sodium channel type 3 ("PN3"). The DNA sequence in FIG. 1 is the cDNA sequence that encodes PN3, and the deduced amino acid sequence is set forth in FIG. 2 (SEQ ID NO:2). Reverse transcription-polymerase chain reaction ("RT-PCR") analysis of RNA from selected rat tissues indicates that PN3 expression is limited to sensory neurons of the peripheral nervous system. A preferred aspect of this invention are cDNA sequences which encode for mammalian TTX-resistant sodium channel proteins that are expressed exclusively in the sensory neurons of the peripheral nervous-system. The term "exclusively expressed" means that the sodium channel mRNA. is found in dorsal root ganglia, nodose ganglia and sciatic nerve but not in brain, spinal cord, heart, skeletal muscle or superior cervical ganglia when assayed by the methods described herein, such as RT-PCR. cDNA sequences which encode for TTX-resistant sodium channel proteins that are predominantly expressed in the sensory neurons of the peripheral nervous system are also contemplated by this invention. The term "predominantly expressed" means that greater than 95% of the expression of the sodiun channel occurs in the particular tissue cited. In situ hybridization to rat DRG demonstrated that PN3 mRNA is present primarily in small DRG neurons. In addition, PN3 was shown to be a voltage-gated sodium channel with a depolarized activation potential, slow inactivation kinetics, and resistant to a high concentration of TTX.

The term "cDNA" or complementary DNA refers to single-stranded or double-stranded DNA sequences obtained by reverse transcription of mRNA isolated from a donor cell. For example, treatment of mRNA with a reverse transcriptase such as AMV reverse transcriptase or M-MuLV reverse transcriptase in the presence of an oligonucleotide primer will furnish an RNA-DNA duplex which can be treated with RNase H, DNA polymerase, and DNA ligase to generate double-stranded cDNA. If desired, the double-stranded cDNA can be denatured by conventional techniques such as heating to generate single-stranded cDNA. The term "cDNA" includes cDNA that is a complementary copy of the naturally occurring mRNA as well as complementary copies of variants of the naturally occurring mRNA, that have the same biological activity. Variants would include, for example, insertions, deletions, sequences with degenerate codons and alleles. Anexample of an insertion is a single additional Gln codon between the $Pro^{584}$ and $Ala^{585}$ codons of the full-length cDNA sequence of PN3, found in several clones.

The term "cRNA" refers to RNA that is a copy of the mRNA transcribed by a cell. CRNA corresponding to mRNA transcribed from a DNA sequence encoding the α-subunit of a mammalian peripheral nerve TTX resistant sodium channel protein is contemplated by this invention.

As mentioned above, it is believed that homologs of the rat TTX-resistant sodium channel described herein are also expressed in other mammalian peripheral nerve tissue, in particular, human tissue. The rat sodium channel cDNA of the. present invention can be used as a probe to discover whether a voltage-gated TTX-resistant sodium channel exists in human peripheral nerve tissue and, if it does, to aid in isolating the cDNA for the human protein.

The human homologue of the rat TTX-resistant PN3 can be cloned using a human DRG cDNA library. Human DRG are obtained at autopsy. The frozen tissue is homogenized and the RNA extracted with guanidine isothiocyanate (Chirgwin, et al. *Biochemistry* 18:5294–5299, 1979). The RNA is size fractionated on a sucrose gradient to enrich for large mRNAs because the sodium channel α-subunits are encoded by large (7–11 kb) transcripts. Double-stranded cDNA is prepared using the Superscript Choice cDNA kit (GIBCO BRL) with either oligo(dT) or random hexamer primers. EcoRI adapters are ligated onto the double-stranded cDNA which is then phosphorylated. The cDNA library is constructed by ligating the double-stranded cDNA into the bacteriophage-lambda ZAP II vector (Stratagene) followed by packaging into phage particles.

Phage are plated out on 150 mm plates on a lawn of XLI-Blue MRF1 bacteria (Stratagene) and plaque replicas are made on Hybond N nylon membranes (Amersham). Filters are hybridized to a rat PN3 cDNA or CRNA probe by standard procedures and detected by autoradiography or chemiluminescence. The signal produced by the rat PN3 probe hybridizing to positive human clones at high stringency should be stronger than obtained with rat brain sodium channel probes hybridizing to these clones. Positive-plaques are further purified by limiting dilution and rescreened by hybridization or PCR. Restriction mapping and polymerase chain reaction will identify overlapping clones that can be assembled by standard techniques into the full-length human homologue of rat PN3. The human clone can be expressed by injecting CRNA transcribed in vitro from the fill-length cDNA clone into Xenopus oocytes, or by transfecting a mammalian cell line with a vector containing the cDNA linked to a suitable promoter.

The human homologue of the rat TTX-resistant PN3 was cloned using the procedure outlined above. From human DRG, RNA was extracted and used to prepare cDNA and the cDNA library. The human PN3 was then obtained using a PN3 probe, and expressed as described above. A comparison of the human PN3 sequence (SEQ ID NO: 10) to other known human and rat voltage-gated sodium channels revealed that the greatest homology is with the rat PN3 channel, where the corresponding human gene is 83% homologous to the rat sequence. The most closely related human channel is the heart I channel, having 64% identity for the amino acid sequence. A similar relationship was observed for rat PN3 in that the most closely related channel was the rat heart channel. A variant of rat PN3 was detected in which an extra Gln residue was present in the interdomain I/II loop, however, no such variant was found in the human DRG. The PN3 and SNS rat DRG sodium channels are very closely related and differ by only seven residues. Six of these seven residues are identical in the human PN3 and rat PN3, so that the human PN3 is more similar to the rat PN3 than to the SNS channel.

Analysis of the open reading frame revealed that the human PN3 sequence has all the hallmark structural features of sodium channels that are predicted from the amino acid sequence: 24 transmembrane segments, charged residues in the S4 transmembrane segments, and the IFM sequence within the highly conserved interdomain II–IV region which constitutes the fast inactivation gate. In addition the human PN3 channel had the identical sequence as rat PN3 for the TTX-sensitivity site within the domain I S5–S6 loop, where there is a Ser in position 357 in human PN3 and position 356 in rat PN3, rather than a Cys residue which is present in all other, that is non-PN3 type, TTX-insensitive/resistant channels. The human and rat channels also shared N-glycosylation consensus sites and cAMP-dependent kinase sites which included several unusual sites in domain II and interdomain II–III.

The present invention also includes expression vectors comprising the DNA or the cDNA described above, host cells transformed with these expression vectors capable of producing the sodium channel of the invention, and cDNA libraries comprising such host cells.

The term "expression vector" refers to any genetic element, e.g., a plasmid, a chromosome, a virus, behaving either as an autonomous unit of polynucleotide expression within a cell or being rendered capable of replication by insertion into a host cell chromosome, having attached to it another polynucleotide segment, so as to bring about the replication and/or expression of the attached segment. Suitable vectors include, but are not limited to, plasmids, bacteriophages and cosmids. Vectors will contain polynucleotide sequences which are necessary to effect ligation or insertion of the vector into a desired host cell and to effect the expression of the attached segment. Such sequences differ depending on the host organism, and will include promoter sequences to effect transcription, enhancer sequences to increase transcription, ribosomal binding site sequences and transcription and translation termination sequences.

The term "host cell" generally refers to prokaryotic or eukaryotic organisms and includes any transformable or transfectable organism which is capable of expressing a protein and can be, or has been, used as a recipient for expression vectors or other transferred DNA. Host cells can also be made to express protein by direct injection with exogenous CRNA translatable into the protein of interest. A preferred host cell is the Xenopus oocyte.

The term "transformed" refers to any known method for the insertion of foreign DNA or RNA sequences into a host prokaryotic cell. The term "transfected" refers to any known method for the insertion of foreign DNA or RNA sequences into a host eukaryotic cell. Such transformed or transfected cells include stably transformed or transfected cells in which the inserted DNA is rendered capable of replication in the host cell. They also include transiently expressing cells which express the inserted DNA or RNA for limited periods of time. The transformation or transfection procedure depends on the host cell being transformed. It can include packaging the polynucleotide in a virus as well as direct uptake of the polynucleotide, such as, for example, lipofection or microinjection. Transformation and transfection can result in incorporation of the inserted DNA into the genome of the host cell or the maintenance of the inserted DNA within the host cell in plasmid form. Methods of transformation are well known in the art and include, but are not limited to, viral infection, electroporation, lipofection and calcium phosphate mediated direct uptake.

It is to be understood that this invention is intended to include other forms of expression vectors, host cells and transformation techniques which serve equivalent functions and which become known to the art hereto.

The term "cDNA library" refers to a collection of clones, usually in a bacteriophage, or less commonly in bacterial plasmids, containing cDNA copies of mRNA sequences derived from a donor cell or tissue.

In addition, the present invention contemplates recombinant polynucleotides, of about 15 to 20 kb, preferably 10 to 15 kb nucleotides in length, comprising a nucleic acid sequence segment of the DNA of SEQ ID NOs: 1 and 9. The invention also includes a recombinant polynucleotide comprising a nucleic acid subsequence derived from the DNA of SEQ ID NOs: 1 and 9. The term "subsequence" refers to a nucleic acid sequence having substantially the same DNA as the sequence of the invention, having certain nucleotide additions or deletions.

The term "polynucleotide" as used herein refers to a polymeric form of nucleotides of any length, either ribonucleotides or deoxyribonucleotides. This term refers only to the primary structure of the molecule. Thus, this term includes double- and single-stranded DNA, as well as double- and single-stranded RNA. It also includes modified, for example, by methylation and/or by capping, and unmodified forms of the polynucleotide. The term "derived from" a designated sequence, refers to a nucleic acid sequence that is comprised of a sequence of approximately at least 6–8 nucleotides, more preferably at least 10–12 nucleotides, and, even more preferably, at least 15–20 nucleotides that correspond to, i.e., are homologous or complementary to, a region of the designated sequence. The derived sequence is not necessarily physically derived from the nucleotide sequence shown, but may be derived in any manner, including for example, chemical synthesis or DNA replication or reverse transcription, which are based on the information provided by the sequences of bases in the region(s) from which the polynucleotide is derived. Further, the term "polynucleotide" is intended to include a recombinant polynucleotide, which is of genomic, cDNA, semisynthetic or synthetic origin which, by virtue of its origin or manipulation is not associated with all or a portion of the polynucleotide with which it is associated in nature and/or is linked to a polynucleotide other than that to which it is linked in nature.

The polynucleotides of the invention can be bound to a reporter molecule to form a polynucleotide probe useful for Northern and Southern blot analysis and in situ hybridization.

The term "reporter molecule" refers to a chemical entity capable of being detected by a suitable detection means, including, but not limited to, spectrophotometric, chemiluminescent, immunochemical, or radiochemical means. The polynucleotides of this invention can be conjugated to a reporter molecule by techniques well known in the art. Typically the reporter molecule contains a functional group suitable for attachment to or incorporation into the polynucleotide. The functional groups suitable for attaching the reporter group are usually activated esters or alkylating agents. Details of techniques for attaching reporter groups are well known in the art. See, for example, Matthews, J. A., Batki, A., Hynds, C., and Kricka, L. J., *Anal. Biochem.*, 151:205–209 (1985) and Engelhardt et al., European Patent Application No. 0 302 175.

The invention not only includes the entire protein expressed by the cDNA sequence of FIG. 1, but also includes protein fragments. These fragments can be obtained by cleaving the full length protein or by using smaller DNA sequences or polynucleotides to express the desired fragment. Accordingly, the invention also includes polynucleotides that can be used to make polypeptides of about 10 to 1500, preferably 10 to 100, amino acids in length. The isolation and purification of such recombinant polypeptides can be accomplished by techniques that are well known in the art, for example preparative chromatographic separations or affinity chromatography. In addition, polypeptides can also be made by synthetic means such as are well known in the art.

The polypeptides of the invention are highly useful for the development of antibodies against PN3. Such antibodies can be used in affinity chromatography to purify recombinant sodium channel proteins or polypeptides, or they can be used as a research tool. For example, antibodies bound to a reporter molecule can be used in histochemical staining techniques to identify other tissues and cell types where PN3 is present, or they can be used to identify epitopic or functional regions of the sodium channel protein of the invention.

The antibodies can be monoclonal or polyclonal and can be prepared by techniques that are well known in the art. Polyclonal antibodies are prepared as follows: an immunogenic conjugate comprising PN3 or a fragment thereof, optionally linked to a carrier protein, is used to immunize a selected mammal such as a mouse, rabbit, goat, etc. Serun from the immunized mammal is collected and treated according to known procedures to separate the immunoglobulin fraction. Monoclonal antibodies are prepared by standard hybridoma cell technology based on that reported by Kohler and Milstein in *Nature* 256:495–497 (1975): spleen cells are obtained from a host animal immunized with the PN3 protein or a fragment thereof, optionally linked to a carrier. Hybrid cells are formed by fusing these spleen cells with an appropriate myeloma cell line and cultured. The antibodies produced by the hybrid cells are screened for their ability to bind to expressed PN3 protein. A number of screening techniques well known in the art, such as, for example, forward or reverse enzyme-linked immunosorbent assay screening methods may be employed. The hybrid cells producing such antibodies are then subjected to recloning and high dilution conditions in order to select a hybrid cell that secretes a homogeneous population of antibodies specific to the PN3 protein. In addition, antibodies can be raised by cloning and expressing nucleotide sequences or mutagenized versions thereof coding at least for the amino acid sequences required for specific binding of natural antibodies, and these expressed proteins used as the immunogen. Antibodies may include the complete immunoglobulin or a fragment thereof. Antibodies may be linked to a reporter group such as is described above with reference to polynucleotides.

As mentioned above, the invention pertains to the cloning and fimctional expression, in Xenopus oocytes, of a rat peripheral nerve TTX-resistant sodium channel. Specifically, the α-subunit of the sodium channel was cloned and expressed. Accordingly, the invention encompasses a rat peripheral nerve TTX-resistant sodium channel α-subunit encoded by the cDNA set forth in FIG. 1, and fragments thereof. Specifically, the invention includes the sodium channel α-subunit having the amino acid sequence set forth in FIG. 2, and fragments thereof. Additionally, the invention encompasses a human peripheral nerve TTX-resistant sodium channel α-subunit encoded by the cDNA set forth in FIG. 5, (SEQ ID NO: 9) and fragments thereof. Specifically, the invention includes the sodium channel α-subunit having the amino acid sequence set forth in FIG. 6, (SEQ ID NO: 10) and fragments thereof.

The sodium channel comprises an α- and a β-subunit. The β-subunit may modulate the function of the channel. However, since the α-subunit is all that is required for the channel to be fully functional, the expression of the cDNA in FIG. 1, will provide a fully functional protein. The gene encoding the β-subunit in peripheral nerve tissue was found to be identical to that found in rat heart, brain and skeletal muscle. The cDNA of the β-subunit is not described herein as it is well known in the art, Isom, et al., *Neuron* 12:1183–1194 (1994). However, it is to be understood that by combining the known sequence for the β-subunit with the α-subunit sequence described herein, one may obtain the complete rat peripheral nerve, voltage-gated, TTX-resistant sodium channel.

Functional expression in Xenopus oocytes shows that PN3 is a voltage-gated sodium channel with a depolarized activation potential, slow inactivation kinetics, and resistant to a high concentration of TTX. PN3 may correspond to the sodium channel mediating TTX-resistant currents in small neurons of the DRG, that have been described in the literature. See for example, Kostyuk, et al., *Neurosci.* 6:2423–2430 (1981); McLean, et al., *Molec. Cell. Biochem.* 80:95–107 (1988); Roy, et al., supra; Caffrey, et al., *Brain Res.* 592:283–297 (1992); Elliott, et al., *J. Physiol.* 463:39–56 (1993); and Ogata, et al., *J. Physiol.* 466:9–37 (1993).

Northern blot analysis indicates that PN3 is encoded by an ~7.5 kb transcript and nucleotide sequence analysis of the PN3 cDNA identifies a 5868-base open reading frame, shown in FIG. 1. The deduced amino acid sequence of PN3, shown in FIG. 2 exhibits the primary structural features of an α-subunit of a voltage-gated sodium channel.

The present invention also includes the use of the voltage-gated, TTX-resistant sodium channel α-subunit as a therapeutic target for compounds to treat disorders of the peripheral nervous system including, but not limited to, allodynia, hyperalgesia, diabetic neuropathy, traumatic injury and AIDS-associated neuropathy. The invention allows for the manipulation of genetic materials by recombinant technology to produce polypeptides that possess the structural and functional characteristics of the voltage-gated, TTX-resistant sodium channel α-subunit found in peripheral nerve tissue, particularly in sensory nerves. Site directed mutagenesis can be used to provide such recombinant polypeptides. For example, synthetic oligonucleotides can be specifically inserted or substituted into the portion of the gene of interest to produce genes encoding for and expressing a specific mutant. Random degenerate oligonucleotides can also be inserted and phage display techniques can be used to identify and isolate polypeptides possessing a fimctional property of interest.

Sodium channels in peripheral nerve tissue play a large role in the transmission of nerve impulses, and therefore are instrumental in understanding neuropathic pain transmission. Neuropathic pain falls into two categories: allodynia, where a normally non-painful stimulus becomes painful, and hyperalgesia, where a usually normal painful stimulus becomes extremely painful. The ability to inhibit the activity of these sodium channels, i.e., reduce the conduction of nerve impulses, will affect the nerve's ability to transmit pain. Selective inhibition of sodium channels in sensory neurons such as dorsal root ganglia will allow the blockage of pain impulses without complicating side effects caused by inhibition of sodium channels in other tissues such as brain and heart. In addition, certain diseases are caused by sodium channels that produce impulses at an extremely high frequency. The ability to reduce the activity of the channel can then eliminate or alleviate the disease. Accordingly, potential therapeutic compounds can be screened by methods well known in the art, to discover whether they can inhibit the activity of the recombinant sodium channel of the invention. Barram, M., et al., *Naun-Schmiedeberg's archives of Pharmacology*, 347: 125–132 (1993) and McNeal, E. T. et al., *J. Med. Chem.*, 28: 381–388 (1985). For similar studies with the acetyl choline receptor, see, Claudio et al., *Science*, 238: 1688–1694 (1987).

The sodium channel of the present invention has the most restrictive tissue distribution of the channels that have been studied. This is of significant value to develop therapeutics that will have a specific target, i.e., that will not inhibit a particular channel in a wide range of tissues. Seven main tissue types were screened by RT-PCR for expression of the unique 410 base amplicon corresponding to positions 5893–6302 of SEQ ID NO:1. PN3 was present in three of the tissues studied: DRG, nodose ganglia and sciatic nerve tissue. PN3 was not present in the remaining tissues studied: brain, spinal cord, heart or skeletal muscle tissue. In view of the previous detection of a sodium channel PN1 mRNA in the peripheral nervous system, (D'Arcangelo et al) other tissues were screened by RT-PCR for the presence of PN1. PN1 was detected in brain, heart, spinal cord and superior cervical ganglia, under conditions in which PN3 was not detected. A tissue distribution profile of human PN3 was determined by analysis of RNA from selected human tissues and commerically available cDNA libraries by RT-PCR. hPN3 was present in two of the tissues studied: DRG and sciatic nerve tissue. hPN3 was not present in the remaining tissues studied: brain, spinal cord, heart, or skeletal muscle tissue.

This invention is directed to inhibiting the activity of PN3 in DRG, nodose ganglia and sciatic nerve tissues. However, it is to be understood that further studies may reveal that PN3 is present in other tissues, and as such, those tissues can also be targeted areas. For example, the detection of PN3 mRNA in nodose ganglia suggests that PN3 may conduct TTX-resistant sodium currents in this and other sensory ganglia of the peripheral nervous system. In addition, it has been found that proteins not normally expressed in certain tissues, are expressed in a disease state. Therefore, this invention is intended to encompass the inhibition of PN3 in tissues and cell types where the protein is normally expressed, and in those tissues and cell types where the protein is only expressed during a disease state.

Another significant characteristic of PN3 is that it is TTX-resistant. It is believed that TTX-resistant sodium channels play a key role in transmitting nerve impulses relating to sensory inputs such as pain and pressure. This will also facilitate the design of therapeutics that can be targeted to a specific area such as the peripheral nerve tissue. Studies of the TTX-resistant site on the protein will facilitate the development of a selective inhibitor. This site is shown in FIG. 2 (♦). It is believed that key amino acid residues in certain domains of the sodium channnel are critical for TTX resistance. Satin, Kyle et al. *Sience*. 256:1202–1205(1992). In the cardiac sodium channel, mutation of $Cys^{374}$→Phe or Tyr rendered the channel TTX sensitive. This position corresponds to $Ser^{356}$ in PN3 (SEQ ID NO: 2), and $Ser^{357}$ in hPN3 (SEQ ID NO: 10) It is believed that non-aromatic residues at this site confer TTX resistance to the sodium channel. Peripheral nerve sodium channels mutated at positions analogous to amino acid residue 356 and DNA sequences encoding therefor are also contemplated by this invention. Specific embodiments include the amino acid sequence of SEQ ID NO:2 in which $Ser^{356}$ is replaced by a non aromatic residue, and DNA sequences encoding therefor. Typical aromatic residues are phenylalanine, tyrosine and tryptophan. Typical non-aromatic residues are threonine, valine, cysteine, aspartate and arginine. Site directed mutagenesis can identify additional residues critical for TTX resistance and provide targets for new therapeutic compounds.

The invention also pertains to an assay for inhibitors of peripheral nerve TTX-resistant sodium channel protein comprising contacting a compound suspected of being an inhibitor with expressed sodium channel and measuring the activity of the sodium channel. The compound can be a substantially pure compound of synthetic origin combined in an aqueous medium, or the compound can be a naturally, occurring material such that the assay medium is an extract of biological origin, such as, for example, a plant, animal, or microbial cell extract. PN3 activity can be measured by methods such as electrophysiology (two electrode voltage clamp or single electrode whole cell patch clamp), guanidinium ion flux assays and toxin-binding assays. An "inhibitor" is defined as generally that amount that results in greater than 50% decrease in PN3 activity, preferably greater than 70% decrease in PN3 activity, more preferably, greater than 90% decrease in PN3 activity.

In addition, the present invention encompasses a method of alleviating pain by inhibiting the activity of the peripheral nerve TTX-resistant sodium channel comprising administering a therapeutically effective amount of a compound having an $IC_{50}$ of 10 $\mu$M or less, preferably $\leqq 1$ $\mu$M. Potential therapeutic compounds are identified based on their ability to inhibit the activity of PN3. Therefore, the aforementioned assay can be used to identify compounds having a therapeutically effective $IC_{50}$.

The term "$IC_{50}$" refers to the concentration of a compound that is required to inhibit by 50% the activity of expressed PN3 when activity is measured by electrophysiology, flux assays and toxin-binding, assays, as mentioned above.

The basic molecular biology techniques employed in accomplishing features of this invention, such as RNA and DNA and plasmid isolation, restriction enzyme digestion, preparation and probing of a cDNA library, sequencing clones, constructing expression vectors, transforming cells, maintaining and growing cell cultures and other general techniques are well known in the art, and descriptions of such techniques can be found in general laboratory manuals such as *Molecular Cloning: A Laboratory Manual* by Sambrook, et al. (Cold Spring Harbor Laboratory Press, 2nd edition, 1989). Accordingly, the following examples are merely illustrative of the techniques by which the invention can be practiced.

Abbreviations

BSA bovine serum albumin
Denhardt's solution 0.02% BSA, 0.02% polyvinylpyrrolidone, 0.02% Ficoll (0.1 g BSA, 0.1 g Ficoll and 0.1 g poly-vinylpyrrolidone per 500 ml)
DRG dorsal root ganglia
EDTA Ethylenediaminetetraacetic acid, tetrasodium salt
MEN 20 mM MOPS, 1 mM EDTA, 5 mM sodium acetate, pH 7.0
MOPS 3-(N-morpholino)propanesulfonic acid (Sigma Chemical Company)
PN3 peripheral nerve sodium channel type 3
PNS peripheral nervous system
SDS sodium dodecyl sulfate
SSC 150 mM NaCl, 15 mM sodium citrate, pH 7.0
SSPE 80 mM NaCl, 10 mM sodium phosphate, 1 mM ethylenediaminetetraacetate, pH 8.0
TEV two electrode voltage clamp
TTX tetrodotoxin Sigma Chemical Company

EXAMPLES

Materials

The plasmid, pBK-CMV, was obtained from Stratagene (La Jolla, Calif.); plasmid, pBSTA, was obtained from A. Goldin at the University of California, Irvine and is described by Goldin, et al., in *Methods in Enzymology* (Rudy & Iverson, eds) 207:279–297.

Example 1

Hybridization of mRNA From Rat DRG

Lumbar DRG #4 and #5 (L4 and L5), brain and spinal cord were removed from anesthetized adult male Sprague-Dawley rats under a dissecting microscope. The tissues were frozen in dry ice and homogenized with a Polytron homogenizer; the RNA was extracted by the guanidine isothiocyanate procedure (Chomczynksi, et al., *Anal. Biochemistry* 162:156–159, 1987). Total RNA (5 $\mu$g of each sample) was dissolved in MEN buffer containing 50% formamide, 6.6% formaldehyde and denatured at 65° C. for 5–10 min. The RNA was electrophoresed through a 0.8% agarose gel containing 8.3% formaldehyde in MEN buffer. The electrode buffer was MEN buffer containing 3.7% formaldehyde; the gel was run at 50 V for 12–18 hr.

After electrophoresis, the gel was rinsed in 2×SSC and the RNA was transferred to a Duralose membrane (Stratagene) with 20×SSC by capillary action; the membrane was baked under vacuum at 80° C. for 1 hr. The membrane was prehybridized in 50% formamide, 5×SSC, 50 mM sodium phosphate, pH 7.1, 1×Denhardt's solution, 0.5% SDS, and sheared, heat-denatured salmon spern DNA (1 mg/ml) for 16 hr at 42° C. The membrane was hybridized in 50% formamide, 5×SSC, 50 mM sodium phosphate, pH 7.1, 1×Denhardt's solution, 0.5% SDS, and sheared, heat-denatured salmon sperm DNA (200 $\mu$g/ml) with a $^{32}$P-labeled cRNA probe (ca. 1–3×$10^6$ cpm/ml) that was complementary to nucleotides 4637–5868 of the rat brain IIA sodium channel $\mu$-subunit sequence for 18 hr at 42° C.; the cRNA probe was synthesized in vitro with T7 RNA polymerase (Pharmacia) using pEAF8 template DNA, Noda et al., *Nature*, 320:188–192 (1986), (obtained from W. A. Catterall, University of Washington) that had been linearized with BstEII.

The membrane was rinsed with 2×SSC, 0.1% SDS at room temperature for 20 min and then washed sequentially with: 2×SSC, 0.1% SDS at 55° C. for 30 min, 0.2×SSC, 0.1% SDS at 65° C. for 30 min, 0.2×SSC, 0.1% SDS at 70° C. for 30 min, and 0.2×SSC, 0.1% SDS, 0.1% sodium pyrophosphate at 70° C. for 20 min. The filter was exposed against Kodak X-omat AR film at −80° C. with intensifying screens for up to 2 weeks.

Size markers, including ribosomal 18S and 28S RNAs and RNA markers (GIBCO BRL), were run in parallel lanes of the gel. Their positions were determined by staining the excised lane with ethidiurn bromide (0.5 μg/ml) followed by photography under UV light. The pEAF8 probe hybridized to mRNAs in the DRG sample with sizes of 11 kb, 9.5 kb, 7.3 kb, and 6.5 kb, estimated on the basis of their positions relative to the standards. When the membrane was reprobed with a cloned fragment corresponding to the novel sodium channel domain IV (SEQ ID NO:3), the 7.3 kb transcript is detected in the DRG mRNA, but this size mRNA is not detected in brain or spinal cord. The probe's sequence (SEQ ID NO:3) was as follows:

```
  1  CTCAACATGG TTACGATGAT GGTGGAGACC GACGAGCAGG GCGAGGAGAA
 51  GACGAAGGTT CTGGGCAGAA TCAACCAGTT CTTTGTGGCC GTCTTCACGG
101  GCGAGTGTGT GATGAAGATG TTCGCCCTGC GACAGTACTA TTTCACCAAC
151  GGCTGGAACG TGTTCGACTT CATAGTGGTG ATCCTGTCCA TTGGGAGTCT
201  GCTGTTTTCT GCAATCCTTA AGTCACTGGA AAACTACTTC TCCCCGACGC
251  TCTTCCGGGT CATCCGTCTG GCCAGGATCG GCCGCATCCT CAGGCTGATC
301  CGAGCAGCCA AGGGGATTCG CACGCTGCTC TTCGCCCTCA TGATGTCCCT
351  GCCCGCCCTC TTCAACATCG GCCTCCTCCT CTTCCTCGTC ATGTTCATCT
401  ACTCCATCTT CGGCATGGCC AGCTTCGCTA ACGTCGTGGA CGAGGCCGGC
451  ATCGACGACA TGTTCAACTT CAAGACCTTT GGCAACAGCA TGCTGTGCCT
501  GTTCCAGATC ACCACCTCGG CCGGCTGGGA CGGCCTCCTC AGCCCCATCC
551  TCAACACGGG GCCTCCCTAC TGCGACCCCA ACCTGCCCAA CAGCAACGGC
601  TCCCGGGGGA ACTGCGGGAG CCCGGCGGTG GGCATCATCT TCTTCACCAC
651  CTACATCATC ATCTCCTTCC TRATCGTGGT CAACATGTAT ATCGCAGTCA
701  TC
```

The probe was obtained as follows: RT-PCR was performed on RNA isolated from rat DRG using degenerate ologonucleotide primers that were designed based on the homologies between known sodium channels in domain IV. The domain IV products were cloned in to a plasmid vector, transformed into *E. coli* and single colonies isolated. The domain IV specific PCR products obtained from several of these colonies were individually sequenced. Cloned novel domain IV sequence (SEQ ID NO:3) was labelled with $^{32}P$ by random priming and used to probe a Northern blot of rat brain, spinal cord and DRG RNA.

Nucleotides 16–689 of the probe's sequence corresponds to nucleotides 4502–5175 of FIG. 1 (excludes the degenerate primer sequence). The ends of the probe are not identical to the sequence in FIG. 1 because of the nature of the primers used for PCR. In addition, the probe has one central base that is different from that of the corresponding domain IV region in FIG. 1; the base at position 141 in the probe is a thymine residue while the corresponding base (position 4627) in FIG. 1 is a cytosine residue. This is likely due to an error made by the enzyme during PCR amplification; it is not a simple sequencing error.

This result suggests that the 7.3 kb mRNA encoding PN3 is uniquely expressed in peripheral neurons and that SEQ ID NO:3 can be used to detect/isolate/differentiate peripheral nervous system sodium channels from others.

Example 2

Construction & Screening of cDNA Library From Rat DRG

EcoRI-adapted cDNA was prepared from normal adult male Sprague-Dawley rat DRG poly(A)$^+$ RNA using the SuperScript Choice System (GIBCO BRL). cDNA (>4 kb) was selected by sucrose gradient fractionation as described by Kieffer, *Gene* 109:115–119 (1991). The cDNA was then ligated into the Zap Express vector (Stratagene), and packaged with the Gigapack II XL lambda packaging extract (Stratagene). Phage ($3.5\times10^5$) were screened by filter hybridization with a $^{32}P$-labelled probe (rBIIa, bases 4637–5868 of Auld, et al., *Neuron* 1:449–461 (1988)). Filters were hybridized in 50% formamide, 5×SSPE, 5×Denhardt's solution, 0.5% SDS, 250 μg/ml sheared, denatured salnon sperm DNA, and 50 mM sodium phosphate at 42° C. and washed in 0.5×SSC/0.1%. SDS at 50° C. Positive clones were excised in vivo into pBK-CMV using the ExAssist/XLOLR system (Stratagene). Southern blots of EcoRI-digested plasmids were hybridized with the $^{32}P$-labelled DNA probe, (SEQ ID NO: 3), representing a novel domain IV segment amplified from DRG RNA with degenerate oligonucleotide primers.

Southern filters were hybridized in 50% formamide, 6×SSC, 5×Denhardt's solution, 0.5% SDS, and 100 μg/ml sheared,.denatured salmon sperm DNA at 42° C. and were washed in 0.1×SSC/0.1% SDS at 65° C.

A plasmid containing a full-length cDNA was identified, designated peripheral nerve sodium channel type 3 ("PN3"), and sequenced on both strands. For oocyte expression analysis, the PN3 cDNA was excised from the vector and, after blunting the ends subcloned into pBSTA.

The deduced amino acid sequence (SEQ ID NO:2) of PN3 is shown in FIGS. 2A–2X. PN3 contains four homologous domains, represented as the regions marked I–IV. Each domain consists of six putative α-helical transmembrane segments, represented as SI–S6. The positively charged residues in the voltage sensor (S4 segments) and the inactivation gate between IIIS6 and IVS1 are highly conserved in PN3. Sites for cAMP-dependent phosphorylation and N-linked glycosylation shown experimentally to exist in other sodium channels (See Catterall, *Physiol. Rev.* 72:S15–S48 (1992)) are also present in PN3. This is shown in FIGS. 2A–2X by the symbols "○" and "●", representing the potential cAMP-dependent phosphorylation sites and potential N-linked glycosylation sites, respectively. Symbols also indicate the TTX resistance site (♦) and the termination codon (*).

Also identified were several PN3 partial clones which contained a single additional Gln between Pro[584] and Ala[585] (↑) of the full-length PN3 sequence. The corresponding RNA had three additional nucleotides, thus establishing that the extra amino acid was not a cloning artifact.

Similar procedures have furnished partial clones coding for additional sodium channel proteins in dorsal root ganglia. Sequencing data of these clones revealed that one of these other clones had a sequence which encoded the disclosed partial amino acid sequence of the sodium channel protein, PN1.

(1986); rBIII is rat brain sodium channel III, described in Joho, et al., *Molec. Brain Res.* 7:105–113 (1990); rSkM1 is rat skeletal muscle, described in Trirmer, et al., *Neuron* 3:33–49 (1989); and rHi1 is rat heart sodium channel, described in Rogart, et al., *PNAS* 86:8170–8174 (1989). The sequence homology between PN3 and the TTX-insensitive cardiac channel and their slow kinetics suggest that they belong to a unique subfamily of sodium channels.

Brain, spinal cord, DRG, nodose ganglia, superior cervical ganglia, sciatic nerve, heart and skeletal muscle tissues were isolated from anesthetized, normal adult male Sprague-Dawley rats and were stored at –80° C. RNA was isolated from each tissue using RNAzol (Tel-Test, Inc.). Random-primed cDNA was reverse transcribed from 500 ng of RNA from each tissue. PCR primers corresponding to positions 5893–5912 of FIG. 1 (forward primer):

5'AAG GCA CTC AGG CAT GCA CA 3' (SEQ ID NO:4) and antisense corresponding to positions 6282–6302 of FIG. 1 (reverse primer):

5'TGG CCG ACT CAC AGG TAT TG 3' (SEQ ID NO:5) targeted the 3'-untranslated region of PN3 and defined a 410 bp amplicon (SEQ ID NO:6) corresponding to positions 5893–6302 of FIG. 1:

```
  1 AAGGCACTCA GGCATGCACA GGGCAGGTTC CAATGTCTTT CTCTGCTGTG
 51 CTAACTCCTT CCCTCTGGAG GTGGCACCAA CCTCCAGCCT CCACCAATGC
101 ATGTCACTGG TCATGGTGTC AGAACTGAAT GGGGACATCC TrGAGAAAGC
151 CCCCACCCCA ATAGGAATCA AAAGCCAAGG ATACTCCTCC ATTCTGACGT
201 CCCTTCCGAG TTCCCAGAAG ATGTCATTGC TCCCTTCTGT TTGTGACCAG
251 AGACGTGATT CACCAACTTC TCGGAGCCAG AGACACATAC CAAAGACTTT
301 TCTGCTGGTG TCGGGCAGTC TTAGAGAAGT CACGTAGGGG TTGGCACTGA
351 GAATTAGGGT TTGCATGCCT GCATGCTCAC AGCTGCCGGA CAATACCTGT
401 GAGTCGGCCA
```

Example 3

Comparison with Amino Acid Sequences

Sequence analyses were done to compare the amino acid sequence of PN3 and selected cloned rat sodium channels, using the Gap, PileUp, and Distances programs of the Wisconsin Sequence Analysis Package (Genetics Computer Group, Inc.). The sodium channels evaluated were as follows:

TABLE 1

| cloned rat sodium channel | percent amino acid similarity with PN3 |
|---|---|
| rBI | 75.4 |
| rBII | 75.5 |
| rBIII | 75.5 |
| rSkM1 | 76.0 |
| rH1 | 77.6 |

where rBI and rB1I are rat brain sodium channels I and II, respectively, described in Noda, et al., *Nature* 320:188–192

Thermal cyclek parameters: 30 s/94° C., 30 s/57° C., 1 min/72° C. (24 cycles); 30 s/94° C., 30 s/57° C., 5 min/72° C. (1 cycle). A positive control (1 ng pBK-CMV/PN3) and a no-template control were also included cDNA from each tissue was also PCR amplified using primers specific for glyceraldehyde-3-phosphate dehydrogenase to demonstrate template viability, as described by Tso, et al., *Nucleic Acid Res.* 13:2485–2502 (1985). PN3 PCR amplicons from nodose ganglia and sciatic nerve were confirmed by nucleotide sequence analysis.

Tissue distribution profile of PN3 by analysis of RNA from selected rat tissues by RT-PCR was as follows:

TABLE 2

| Tissue | RT-PCR |
|---|---|
| Brain | – |
| Spinal cord | – |
| DRG | + |
| Nodose ganglia | + |

TABLE 2-continued

| Tissue | RT-PCR |
| --- | --- |
| Sciatic nerve | + |
| Heart | − |
| Skeletal muscle | − |
| Superior cervical ganglia | − |

As can be seen from Table 2, RNA analysis suggests that PN3 mRNA expression is limited to DRG and nodose ganglia of the PNS. PN3 mRNA was readily detected in DRG and nodose ganglia by amplification for only 25 cycles; a small amount of PN3 mRNA was also detected in sciatic nerve after 25 cycles. PN3 mRNA was not detected in brain, spinal cord, heart, skeletal muscle, or superior cervical ganglia after 35 cycles of amplification.

Additional RT-PCR analyses of DRG mRNA detected rBI, RBII, RBIII, and rH1, along with peripheral nerve sodium channel type 1 (PN1), described in D'Arcangelo, et al., supra. PN1 was also detected in brain, heart, spinal cord and superior cervical ganglia under conditions in which PN3 was not detected.

Example 4

In Situ Hybridization

Oligonucleotide probe sequences were identified from the unique 3'-untranslated region of PN3 (sense and antisense probes were complementary to each other). The sense probe had the following sequence:

5'AGG CAC TCA GGC ATG CAC AGG GCA GGT TCC AAT GTC TTT CTC TGC T 3' (SEQ ID NO:7) and the antisense had the following sequence:

3'TCC GTG AGT CCG TAC GTG TCC CGT CCA AGG TTA CAG AAA GAG ACG A 5' (SEQ ID NO:8) both corresponding to positions 5894–5939.

Normal rats were perfused with 4% paraformaldehyde; lumbar DRG #4–#6 (L4–L6) were removed, postfixed in the same solution, and cryoprotected in 20% sucrose. Frozen sections (10 $\mu$m) were cut and hybridized overnight at 39° C. in a solution containing $^{35}$S-ATP labelled oligonucleotides (specific activity=$5\times10^7$–$1\times10^8$ cpm/$\mu$g), 50% formamide, 4×SSC, 0.5 mg/ml salmon sperm DNA, and 1×Denhardt's solution. Sections were washed over a period of 6 hours in 2×–0.2×SSC containing 0.1%- β-mercaptoethanol, dehydrated in a series of ethanols (50%–100%) containing 0.3 M ammonium acetate, and apposed to sheet film (Amersham Bmax) or emulsion (Amersham LM-1) for 2 and 5 weeks, respectively. The cell surface area of all neurons with a distinct nucleus was measured from stained sections obtained from 3 ganglia using a computerized image analysis system (Imaging Research, Inc.).

In situ hybridization of these PN3-specific oligonucleotide probes to rat DRG showed that PN3 mRNA is specifically expressed in neuronal cells. The labelled cells were distributed throughout the ganglia, but most labelled neurons were small in somal area (<1500 $\mu m^2$) . PN3 mRNA was not detected in the axons of L4 and L5 DRG neurons by in situ analysis; however, RT-PCR analysis detected PN3 mRNA in the sciatic nerve. This difference is attributed to the greater sensitivity of RT-PCR amplification versus in situ hybridization.

FIG. 3 depicts a frequency histogram of somal area summed from 10 $\mu$m sections through three ganglia. The area of labelled neurons is represented by filled bars (mean±standard deviation: 725±265 $\mu m^2$; n=44), the area of all neurons is represented by open bars (1041±511 $\mu m^2$; n=130).

Example 5

Expression of Full Lenght Clone cRNA was prepared from PN3 subcloned into pBSTA using a T7 in vitro transcription kit (Ambion, mMessage mMachine) and was injected into stage V and VI Xenopus oocytes using a Nanojector (Drummond), as described in Goldin, supra. After 2.5 days at 20° C., the oocytes were impaled with agarose-cushion electrodes (0.3–0.8 MOhm) and voltage-clamped with a Geneclamp 500 amplifier (Axon Instruments) in TEV mode. See Schreibmayer, et al., *Pflugers Arch*. 426:453–458 (1994).

Stimulation and recording were controlled by a computer running pClamp (Axon Instruments), Kegel, et al. *J. Neurosci. Meth*. 12:317–330 (1982). Oocytes were perfused with a solution containing: 81 mM NaCl, 2 mM KCl, 1 mM $MgCl_2$, 0.3 mM $CaCl_2$, 20 mM Hepes-NaOH, pH 7.5.

FIG. 4(*a*) shows the currents produced by step depolarizations of an oocyte injected with 18 ng of PN3 cRNA from a holding potential of −100 mV to −30 mV through $^+$50 mV. No inward current was observed in oocytes injected with water. Data were collected using the Geneclamp hardware leak subtraction, filtered at 5 kHz with a 4-pole Bessel filter, and sampled at 50 kHz. Expression of PN3 produced an inward current with slow inactivation kinetics, similar to that of the rBIIa (Patton, et al., *Neuron* 7:637–647 (1991)) and rSkMI α-subunits expressed in the absence of the β1-subunit. However, coinjection of 1.3 ng of human sodium channel β1-subunit (hSCNβ1, as described by McClatchey, et al., *Hum. Molec. Gen*. 2:745–749 (1993)) cRNA with PN3 cRNA did not accelerate the inactivation kinetics; coexpression of this quantity of hSCNβ1 cRNA with rBIIa CRNA was sufficient to accelerate maximally the inactivation kinetics of rBIIa. Therefore, PN3 may possess inherently slow kinetics. The amino acid sequence of hSCNβ1 and rat brain sodium channel β1-subunit (rSCNβ1, as described by Isom, *Science* 256:839–842 (1992)) are 96% identical; rSCNβ1 and a cloned rat DRG β1-subunit have identical amino acid sequences.

Examination of the current/voltage relationship reveals a striingly depolarized channel activation potential, as can be seen in FIG. 4(*b*). In this expression system, PN3 exhibits little or no activation at 0 mV, whereas most cloned sodium channels generally begin to activate between −60 and −30 mV. See for example, Joho, et al., supra; Patton, et al., supra; Trimmer, et al., supra; and Cribbs, et al., *FEBS Lett*. 275:195200 (1990). To demonstrate the sodium dependence of these induced currents, the extracellular sodium concentration was reduced from ~91 mM to ~50 mM by substituting N-methyl-D-glucamine. The resulting inward current was reduced and the reversal potential was shifted from $^+$43 mV to $^+$12 mV. Further reduction of the extracellular sodium concentration to −21 mM shifted the reversal potential to −22 mV.

Sodium channels are distinctively sensitive or insensitive to neurotoxins such as TTX. The TTX-sensitive brain and skeletal muscle sodium channels are blocked by nanomolar TTX concentrations, whereas the TTX-insensitive cardiac sodium channels are blocked by micromolar TTX concentrations. In rat heart sodium channel 1 (RH1), $Cys^{374}$ is a critical determinant of TTX-insensitivity, as shown in Satin, et al., *Science* 256:1202–1205(1992); in the TTX-sensitive rBI, RBII, RBII, and rSkM1, the corresponding residue is either Phe or Tyr. In PN3, this position is occupied by a Ser residue ($Ser^{356}$). When expressed in Xenopus oocytes, the PN3 sodium current is highly resistant to TTX ($IC_{50} \geqq 100$ μM). FIG. 4(*c*) shows the concentration dependence for TTX blockage of PN3 sodium current (mean and range; n=2). For this experiment, the oocytes were depolarized from −100 mV to $^{+}$20 mV for approximately 10 ms at 0.1 Hz; P/−4 leak subtraction was used (Bezanilla, et al., *J. Gen. Physiol.* 70:549–566 (1977)). There was a slow "rundown" of the current with time, and a correction was made for the resulting sloping baseline. Varying concentrations of TTX in bath solution were perfused over the oocyte and the current amplitude was allowed to attain steady state before the effect was recorded.

Example 6

Specific Antibody for PN3

A 15-mer peptide(CDPNLPNSNGSRGNC) was synthesized and and coupled to keyhole limpet hemocyanin prior to injection into rabbit. The sequence of the peptide corresponded to residues 1679–1693 of FIG. 2. Out of the two rabbits injected with the antigen only one yielded antiserum that is useful in characterizing the PN3 ion channel protein. The antiserum was then affinity purified by passage through a peptide affinity column. Immunohistochemical experiments substantiated earlier observations using PN3 antisense oligonucleotide probe(in situ hybridization) that PN3 was largely localized in the small sensory neurons of the dorsal root ganglia (DRG). In addition to the sensory neurons of DRG, a small number of transmission neurons in lamina 10 of the spinal cord showed immunoreactivity with the PN3 antibody. Because only a subset of neurons were positive for PN3 expression, PN3 mRNA could have been undetectable by RT-PCR assays using the entire spinal cord (dilution effect).

Immunoprecipitation experiments indicated that PN3 expressing Chinese hamster lung (CHL) cells had a ~250 kD protein which corresponds to the α-subunit. Since the peptide sequence does not match with any other protein, particularly other sodium channels, the antibody could be very specific reagent to characterize the PN3 protein. In addition, the antibody could be used as a tool to understand the role of PN3 in nociceptive pathways. By infusing the antibody in rats so that it 'soaks-up' all available PN3 protein and testing the rats in pain models one could begin to investigate the role of PN3 function in pain pathways.

Example 7

Variants of PN3

A variant of PN3, PN3a has been identified by sequencing a full-length cDNA clone. The sequence of PN3a is identical to that of PN3, including the 5'-and 3'-UTR, except for an additional amino acid, Gln, at $Pro^{584}$ of PN3 set forth in SEQ ID NO: 2. The insertion of Gln in this region was previously reported from RT-PCR experiments. PN3a expressed at a higher level than PN3 inXenopus oocytes and exhibited otherwise the same characteristics as PN3, such as resistance to high concentrations of TTX and depolarized activation potential.

Another cDNA clone had the same sequence as PN3 in the coding region, but the 5'-UTR sequence diverged 33 bp upstream of the start codon, ATG. Another cDNA clone had a longer 3'-UTR with an additional ~1 KB and a second polyadenylation signal. These sequence differences in the noncoding region indicate that regulation of the use of different polyadenylation signal and/or interaction with different transcription elements of the 5'-UTR could play a role in expression of PN3 in distinct subsets of sensory neurons.

Although the foregoing invention has been described in some detail by way of illustration and example for purposes of clarity and understanding, it will be obvious that certain changes and modifications may be practiced within the scope of the appended claims.

What is claimed is:

1. A purified and isolated polynucleotide encoding a peripheral nerve tetrodotoxin-resistant sodium channel alpha subunit polypeptide comprising the amino acid sequence of SEQ ID NO:10.

2. The polynucleotide of claim 1 wherein the polynucleotide comprises SEQ ID NO:9 and encodes human peripheral nerve tetrodotoxin-resistant sodium channel alpha subunit polypeptide.

3. The polynucleotide of claim 1 wherein said polynucleotide is recombinant cDNA.

4. Expression vectors comprising the polynucleotide of claim 1.

5. Host cells transformed with the expression vectors of claim 4.

6. A cDNA library comprising the host cells of claim 5.

7. A method of producing a polypeptide comprising the amino acid sequence of SEQ ID NO:10 comprising culturing the host cells of claim 5 under conditions suitable for expression of the polypeptide.

* * * * *

SEQUENCE LISTING

```
(1) GENERAL INFORMATION:

   (iii) NUMBER OF SEQUENCES: 10

(2) INFORMATION FOR SEQ ID NO: 1:

     (i) SEQUENCE CHARACTERISTICS:
          (A) LENGTH: 6344 base pairs
          (B) TYPE: nucleic acid
          (C) STRANDEDNESS: single
          (D) TOPOLOGY: linear

    (ii) MOLECULE TYPE: cDNA

   (iii) HYPOTHETICAL: NO

    (iv) ANTI-SENSE: NO

    (vi) ORIGINAL SOURCE:
          (A) ORGANISM: rat
          (F) TISSUE TYPE: Dorsal root ganglia
          (G) CELL TYPE: Peripheral nerve

    (xi) SEQUENCE DESCRIPTION: SEQ ID NO: 1:

CTTCCCCAAG AAGAATGAGA AGATGGAGCT CCCCTTTGCG TCCGTGGGAA CTACCAATTT     60

CAGACGGTTC ACTCCAGAGT CACTGGCAGA GATCGAGAAG CAGATTGCTG CTCACCGCGC    120
```

-continued

```
AGCCAAGAAG GCCAGAACCA AGCACAGAGG ACAGGAGGAC AAGGGCGAGA AGCCCAGGCC    180
TCAGCTGGAC TTGAAAGCCT GTAACCAGCT GCCCAAGTTC TATGGTGAGC TCCCAGCAGA    240
ACTGGTCGGG GAGCCCCTGG AGGACCTAGA CCCTTTCTAC AGCACACACC GGACATTCAT    300
GGTGTTGAAT AAAAGCAGGA CCATTTCCAG ATTCAGTGCC ACTTGGGCCC TGTGGCTCTT    360
CAGTCCCTTC AACCTGATCA GAAGAACAGC CATCAAAGTG TCTGTCCATT CCTGGTTCTC    420
CATATTCATC ACCATCACTA TTTTGGTCAA CTGCGTGTGC ATGACCCGAA CTGATCTTCC    480
AGAGAAAGTC GAGTACGTCT TCACTGTCAT TTACACCTTC GAGGCTCTGA TTAAGATACT    540
GGCAAGAGGG TTTTGTCTAA ATGAGTTCAC TTATCTTCGA GATCCGTGGA ACTGGCTGGA    600
CTTCAGTGTC ATTACCTTGG CGTATGTGGG TGCAGCGATA GACCTCCGAG GAATCTCAGG    660
CCTGCGGACA TTCCGAGTTC TCAGAGCCCT GAAAACTGTT TCTGTGATCC CAGGACTGAA    720
GGTCATCGTG GGAGCCCTGA TCCACTCAGT GAGGAAGCTG GCCGACGTGA CTATCCTCAC    780
AGTCTTCTGC CTGAGCGTCT TCGCCTTGGT GGGCCTGCAG CTCTTTAAGG GGAACCTTAA    840
GAACAAATGC ATCAGGAACG GAACAGATCC CCACAAGGCT GACAACCTCT CATCTGAAAT    900
GGCAGAATAC ATCTTCATCA AGCCTGGTAC TACGGATCCC TTACTGTGCG GCAATGGGTC    960
TGATGCTGGT CACTGCCCTG GAGGCTATGT CTGCCTGAAA ACTCCTGACA ACCCGGATTT   1020
TAACTACACC AGCTTTGATT CCTTTGCGTG GCATTCCTC TCACTGTTCC GCCTCATGAC   1080
GCAGGACTCC TGGGAGCGCC TGTACCAGCA GACACTCCGG GCTTCTGGGA AAATGTACAT   1140
GGTCTTTTTC GTGCTGGTTA TTTTCCTTGG ATCGTTCTAC CTGGTCAATT TGATCTTGGC   1200
CGTGGTCACC ATGGCGTATG AAGAGCAGAG CCAGGCAACA ATTGCAGAAA TCGAAGCCAA   1260
GGAAAAAAAG TTCCAGGAAG CCCTTGAGGT GCTGCAGAAG GAACAGGAGG TGCTGGCAGC   1320
CCTGGGGATT GACACGACCT CGCTCCAGTC CCACAGTGGA TCACCCTTAG CCTCCAAAAA   1380
CGCCAATGAG AGAAGACCCA GGGTGAAATC AAGGGTGTCA GAGGGCTCCA CGGATGACAA   1440
CAGGTCACCC CAATCTGACC CTTACAACCA GCGCAGGATG TCTTTCCTAG GCCTGTCTTC   1500
AGGAAGACGC AGGGCTAGCC ACGGCAGTGT GTTCCACTTC CGAGCGCCCA GCCAAGACAT   1560
CTCATTTCCT GACGGGATCA CGGATGATGG GGTCTTTCAC GGAGACCAGG AAAGCCGTCG   1620
AGGTTCCATA TTGCTGGGCA GGGGTGCTGG GCAGACAGGT CCACTCCCCA GGAGCCCACT   1680
GCCTCAGTCC CCCAACCCTG GCCGTAGACA TGGAGAAGAG GGACAGCTCG GAGTGCCCAC   1740
TGGTGAGCTT ACCGCTGGAG CGCCTGAAGG CCCGGCACTC GACACTACAG GGCAGAAGAG   1800
CTTCCTGTCT GCGGGCTACT TGAACGAACC TTTCCGAGCA CAGAGGGCCA TGAGCGTTGT   1860
CAGTATCATG ACTTCTGTCA TTGAGGAGCT TGAAGAGTCT AAGCTGAAGT GCCCACCCTG   1920
CTTGATCAGC TTCGCTCAGA AGTATCTGAT CTGGGAGTGC TGCCCCAAGT GGAGGAAGTT   1980
CAAGATGGCG CTGTTCGAGC TGGTGACTGA CCCCTTCGCA GAGCTTACCA TCACCCTCTG   2040
CATCGTGGTG AACACCGTCT TCATGGCCAT GGAGCACTAC CCCATGACCG ATGCCTTCGA   2100
TGCCATGCTT CAAGCCGGCA ACATTGTCTT CACCGTGTTT TTCACAATGG AGATGGCCTT   2160
CAAGATCATT GCCTTCGACC CCTACTATTA CTTCCAGAAG AAGTGGAATA TCTTCGACTG   2220
TGTCATCGTC ACCGTGAGCC TTCTGGAGCT GAGCGCATCC AAGAAGGGCA GCCTGTCTGT   2280
GCTCCGTACC TTCCGCTTGC TGCGGGTCTT CAAGCTGGCC AAGTCCTGGC CCACCCTGAA   2340
CACCCTCATC AAGATCATCG GGAACTCCGT GGGGGCCCTG GGCAACCTGA CCTTTATCCT   2400
GGCCATCATC GTCTTCATCT TCGCCCTGGT CGGAAAGCAG CTTCTCTCAG AGGACTACGG   2460
```

-continued

```
GTGCCGCAAG GACGGCGTCT CCGTGTGGAA CGGCGAGAAG CTCCGCTGGC ACATGTGTGA   2520

CTTCTTCCAT TCCTTCCTGG TCGTCTTCCG AATCCTCTGC GGGGAGTGGA TCGAGAACAT   2580

GTGGGTCTGC ATGGAGGTCA GCCAGAAATC CATCTGCCTC ATCCTCTTCT TGACTGTGAT   2640

GGTGCTGGGC AACCTAGTGG TGCTCAACCT TTTCATCGCT TTACTGCTGA ACTCCTTCAG   2700

CGCGGACAAC CTCACGGCTC CAGAGGATGA CGGGGAGGTG AACAACTTGC AGTTAGCACT   2760

GGCCAGGATC CAGGTACTTG GCCATCGGGC CAGCAGGGCC ATCGCCAGTT ACATCAGCAG   2820

CCACTGCCGA TTCCGCTGGC CCAAGGTGGA GACCCAGCTG GGCATGAAGC CCCCACTCCT   2880

CAGCTCAGAG GCCAAGAACC ACATTGCCAC TGATGCTGTC AGTGCTGCAG TGGGGAACCT   2940

GACAAAGCCA GCTCTCAGTA GCCCCAAGGA GAACCACGGG GACTTCATCA CTGATCCCAA   3000

CGTGTGGGTC TCTGTGCCCA TTGCTGAGGG GGAATCTGAC CTCGACGAGC TCGAGGAAGA   3060

TATGGAGCAG GCTTCGCAGA GCTCCTGGCA GGAAGAGGAC CCCAAGGGAC AGCAGGAGCA   3120

GTTGCCACAA GTCCAAAAGT GTGAAAACCA CCAGGCAGCC AGAAGCCCAG CCTCCATGAT   3180

GTCCTCTGAG GACCTGGCTC CATACCTGGG TGAGAGCTGG AAGAGGAAGG ATAGCCCTCA   3240

GGTCCCTGCC GAGGGAGTGG ATGACACGAG CTCCTCTGAG GGCAGCACGG TGGACTGCCC   3300

GGACCCAGAG GAAATCCTGA GGAAGATCCC CGAGCTGGCA GATGACCTGG ACGAGCCCGA   3360

TGACTGTTTC ACAGAAGGCT GCACTCGCCG CTGTCCCTGC TGCAACGTGA ATACTAGCAA   3420

GTCTCCTTGG GCCACAGGCT GGCAGGTGCG CAAGACCTGC TACCGCATCG TGGAGCACAG   3480

CTGGTTTGAG AGTTTCATCA TCTTCATGAT CCTGCTCAGC AGTGGAGCGC TGGCCTTTGA   3540

GGATAACTAC CTGGAAGAGA AACCCCGAGT GAAGTCCGTG CTGGAGTACA CTGACCGAGT   3600

GTTCACCTTC ATCTTCGTCT TTGAGATGCT GCTCAAGTGG GTAGCCTATG GCTTCAAAAA   3660

GTATTTCACC AATGCCTGGT GCTGGCTGGA CTTCCTCATT GTGAACATCT CCCTGACAAG   3720

CCTCATAGCG AAGATCCTTG AGTATTCCGA CGTGGCGTCC ATCAAAGCCC TTCGGACTCT   3780

CCGTGCCCTC CGACCGCTGC GGGCTCTGTC TCGATTCGAA GGCATGAGGG TAGTGGTGGA   3840

TGCCCTCGTG GGCGCCATCC CCTCCATCAT GAACGTCCTC CTCGTCTGCC TCATCTTCTG   3900

GCTCATCTTC AGCATCATGG GCGTGAACCT CTTCGCCGGG AAATTTTCGA AGTGCGTCGA   3960

CACCAGAAAT AACCCATTTT CCAACGTGAA TTCGACGATG GTGAATAACA AGTCCGAGTG   4020

TCACAATCAA AACAGCACCG GCCACTTCTT CTGGGTCAAC GTCAAAGTCA ACTTCGACAA   4080

CGTCGCTATG GGCTACCTCG CACTTCTTCA GGTGGCAACC TTCAAAGGCT GGATGGACAT   4140

AATGTATGCA GCTGTTGATT CCGGAGAGAT CAACAGTCAG CCTAACTGGG AGAACAACTT   4200

GTACATGTAC CTGTACTTCG TCGTTTTCAT CATTTTCGGT GGCTTCTTCA CGCTGAATCT   4260

CTTTGTTGGG GTCATAATCG ACAACTTCAA CCAACAGAAA AAAAAGCTAG GAGGCCAGGA   4320

CATCTTCATG ACAGAAGAGC AGAAGAAGTA CTACAATGCC ATGAAGAAGC TGGGCTCCAA   4380

GAAACCCCAG AAGCCCATCC CACGGCCCCT GAATAAGTAC CAAGGCTTCG TGTTTGACAT   4440

CGTGACCAGG CAAGCCTTTG ACATCATCAT CATGGTTCTC ATCTGCCTCA ACATGATCAC   4500

CATGATGGTG GAGACCGACG AGCAGGGCGA GGAGAAGACG AAGGTTCTGG GCAGAATCAA   4560

CCAGTTCTTT GTGGCCGTCT TCACGGGCGA GTGTGTGATG AAGATGTTCG CCCTGCGACA   4620

GTACTACTTC ACCAACGGCT GGAACGTGTT CGACTTCATA GTGGTGATCC TGTCCATTGG   4680

GAGTCTGCTG TTTTCTGCAA TCCTTAAGTC ACTGGAAAAC TACTTCTCCC CGACGCTCTT   4740

CCGGGTCATC CGTCTGGCCA GGATCGGCCG CATCCTCAGG CTGATCCGAG CAGCCAAGGG   4800

GATTCGCACG CTGCTCTTCG CCCTCATGAT GTCCCTGCCC GCCCTCTTCA ACATCGGCCT   4860
```

-continued

```
CCTCCTCTTC CTCGTCATGT TCATCTACTC CATCTTCGGC ATGGCCAGCT TCGCTAACGT   4920
CGTGGACGAG GCCGGCATCG ACGACATGTT CAACTTCAAG ACCTTTGGCA ACAGCATGCT   4980
GTGCCTGTTC CAGATCACCA CCTCGGCCGG CTGGGACGGC CTCCTCAGCC CCATCCTCAA   5040
CACGGGGCCT CCCTACTGCG ACCCCAACCT GCCCAACAGC AACGGCTCCC GGGGGAACTG   5100
CGGGAGCCCG GCGGTGGGCA TCATCTTCTT CACCACCTAC ATCATCATCT CCTTCCTCAT   5160
CGTGGTCAAC ATGTACATCG CAGTGATTCT GGAGAACTTC AACGTGGCCA CCGAGGAGAG   5220
CACGGAGCCC CTGAGCGAGG ACGACTTCGA CATGTTCTAT GAGACCTGGG AGAAGTTCGA   5280
CCCGGAGGCC ACCCAGTTCA TTGCCTTTTC TGCCCTCTCA GACTTCGCGG ACACGCTCTC   5340
CGGCCCTCTT AGAATCCCCA AACCCAACCA GAATATATTA ATCCAGATGG ACCTGCCGTT   5400
GGTCCCCGGG GATAAGATCC ACTGTCTGGA CATCCTTTTT GCCTTCACAA AGAACGTCTT   5460
GGGAGAATCC GGGGAGTTGG ACTCCCTGAA GACCAATATG GAAGAGAAGT TTATGGCGAG   5520
CAATCTCTCC AAAGCATCCT ATGAACCAAT AGCCACCACC CTCCGGTGGA AGCAGGAAGA   5580
CCTCTCAGCC ACAGTCATTC AAAAGGCCTA CCGGAGCTAC ATGCTGCACC GCTCCTTGAC   5640
ACTCTCCAAC ACCCTGCATG TGCCCAGGGC TGAGGAGGAT GGCGTGTCAC TTCCCGGGGA   5700
AGGCTACGTT ACATTCATGG CAAACAGTGG ACTCCCGGAC AAATCAGAAA CTGCCTCTGC   5760
TACGTCTTTC CCGCCATCCT ATGACAGTGT CACCAGGGGC CTGAGTGACC GGGCCAACAT   5820
TAACCCATCT AGCTCAATGC AAAATGAAGA TGAGGTCGCT GCTAAGGAAG GAAACAGCCC   5880
TGGACCTCAG TGAAGGCACT CAGGCATGCA CAGGGCAGGT TCCAATGTCT TTCTCTGCTC   5940
TGCTAACTCC TTCCCTCTGG AGGTGGCACC AACCTCCAGC CTCCACCAAT GCATGTCACT   6000
GGTCATGGTG TCAGAACTGA ATGGGGACAT CCTTGAGAAA GCCCCCACCC CAATAGGAAT   6060
CAAAAGCCAA GGATACTCCT CCATTCTGAC GTCCCTTCCG AGTTCCCAGA AGATGTCATT   6120
GCTCCCTTCT GTTTGTGACC AGAGACGTGA TTCACCAACT TCTCGGAGCC AGAGACACAT   6180
ACCAAAGACT TTTCTGCTGG TGTCGGGCAG TCTTAGAGAA GTCACGTAGG GGTTGGCACT   6240
GAGAATTAGG GTTTGCATGC CTGCATGCTC ACAGCTGCCG GACAATACCT GTGAGTCGGC   6300
CATTAAAATT AATATTTTTA AAGTTAAAAA AAAAAAAAAA AAAA                   6344
```

(2) INFORMATION FOR SEQ ID NO: 2:

(i) SEQUENCE CHARACTERISTICS:
(A) LENGTH: 1956 amino acids
(B) TYPE: amino acid
(C) STRANDEDNESS: <Unknown>
(D) TOPOLOGY: not relevant (ii) MOLECULE TYPE: protein (iii) HYPOTHETICAL: YES (vi) ORIGINAL SOURCE:
(A) ORGANISM: rat
(F) TISSUE TYPE: dorsal root ganglia
(G) CELL TYPE: peripheral nerve (xi) SEQUENCE DESCRIPTION: SEQ ID NO: 2:

```
Met Glu Leu Pro Phe Ala Ser Val Gly Thr Thr Asn Phe Arg Arg Phe
1               5                   10                  15

Thr Pro Glu Ser Leu Ala Glu Ile Glu Lys Gln Ile Ala Ala His Arg
            20                  25                  30

Ala Ala Lys Lys Ala Arg Thr Lys His Arg Gly Gln Glu Asp Lys Gly
        35                  40                  45
```

-continued

```
Glu Lys Pro Arg Pro Gln Leu Asp Leu Lys Ala Cys Asn Gln Leu Pro
    50                  55                  60

Lys Phe Tyr Gly Glu Leu Pro Ala Glu Leu Val Gly Glu Pro Leu Glu
65                  70                  75                  80

Asp Leu Asp Pro Phe Tyr Ser Thr His Arg Thr Phe Met Val Leu Asn
                85                  90                  95

Lys Ser Arg Thr Ile Ser Arg Phe Ser Ala Thr Trp Ala Leu Trp Leu
            100                 105                 110

Phe Ser Pro Phe Asn Leu Ile Arg Arg Thr Ala Ile Lys Val Ser Val
        115                 120                 125

His Ser Trp Phe Ser Ile Phe Ile Thr Ile Thr Ile Leu Val Asn Cys
    130                 135                 140

Val Cys Met Thr Arg Thr Asp Leu Pro Glu Lys Val Glu Tyr Val Phe
145                 150                 155                 160

Thr Val Ile Tyr Thr Phe Glu Ala Leu Ile Lys Ile Leu Ala Arg Gly
                165                 170                 175

Phe Cys Leu Asn Glu Phe Thr Tyr Leu Arg Asp Pro Trp Asn Trp Leu
            180                 185                 190

Asp Phe Ser Val Ile Thr Leu Ala Tyr Val Gly Ala Ala Ile Asp Leu
        195                 200                 205

Arg Gly Ile Ser Gly Leu Arg Thr Phe Arg Val Leu Arg Ala Leu Lys
    210                 215                 220

Thr Val Ser Val Ile Pro Gly Leu Lys Val Ile Val Gly Ala Leu Ile
225                 230                 235                 240

His Ser Val Arg Lys Leu Ala Asp Val Thr Ile Leu Thr Val Phe Cys
                245                 250                 255

Leu Ser Val Phe Ala Leu Val Gly Leu Gln Leu Phe Lys Gly Asn Leu
            260                 265                 270

Lys Asn Lys Cys Ile Arg Asn Gly Thr Asp Pro His Lys Ala Asp Asn
        275                 280                 285

Leu Ser Ser Glu Met Ala Glu Tyr Ile Phe Ile Lys Pro Gly Thr Thr
    290                 295                 300

Asp Pro Leu Leu Cys Gly Asn Gly Ser Asp Ala Gly His Cys Pro Gly
305                 310                 315                 320

Gly Tyr Val Cys Leu Lys Thr Pro Asp Asn Pro Asp Phe Asn Tyr Thr
                325                 330                 335

Ser Phe Asp Ser Phe Ala Trp Ala Phe Leu Ser Leu Phe Arg Leu Met
            340                 345                 350

Thr Gln Asp Ser Trp Glu Arg Leu Tyr Gln Gln Thr Leu Arg Ala Ser
        355                 360                 365

Gly Lys Met Tyr Met Val Phe Phe Val Leu Val Ile Phe Leu Gly Ser
    370                 375                 380

Phe Tyr Leu Val Asn Leu Ile Leu Ala Val Val Thr Met Ala Tyr Glu
385                 390                 395                 400

Glu Gln Ser Gln Ala Thr Ile Ala Glu Ile Glu Ala Lys Glu Lys Lys
                405                 410                 415

Phe Gln Glu Ala Leu Glu Val Leu Gln Lys Glu Gln Glu Val Leu Ala
            420                 425                 430

Ala Leu Gly Ile Asp Thr Thr Ser Leu Gln Ser His Ser Gly Ser Pro
        435                 440                 445

Leu Ala Ser Lys Asn Ala Asn Glu Arg Arg Pro Arg Val Lys Ser Arg
    450                 455                 460
```

-continued

```
Val Ser Glu Gly Ser Thr Asp Asp Asn Arg Ser Pro Gln Ser Asp Pro
465                 470                 475                 480

Tyr Asn Gln Arg Arg Met Ser Phe Leu Gly Leu Ser Ser Gly Arg Arg
                485                 490                 495

Arg Ala Ser His Gly Ser Val Phe His Phe Arg Ala Pro Ser Gln Asp
            500                 505                 510

Ile Ser Phe Pro Asp Gly Ile Thr Asp Asp Gly Val Phe His Gly Asp
        515                 520                 525

Gln Glu Ser Arg Arg Gly Ser Ile Leu Leu Gly Arg Gly Ala Gly Gln
    530                 535                 540

Thr Gly Pro Leu Pro Arg Ser Pro Leu Pro Gln Ser Pro Asn Pro Gly
545                 550                 555                 560

Arg Arg His Gly Glu Glu Gly Gln Leu Gly Val Pro Thr Gly Glu Leu
                565                 570                 575

Thr Ala Gly Ala Pro Glu Gly Pro Ala Leu Asp Thr Thr Gly Gln Lys
            580                 585                 590

Ser Phe Leu Ser Ala Gly Tyr Leu Asn Glu Pro Phe Arg Ala Gln Arg
        595                 600                 605

Ala Met Ser Val Val Ser Ile Met Thr Ser Val Ile Glu Glu Leu Glu
    610                 615                 620

Glu Ser Lys Leu Lys Cys Pro Pro Cys Leu Ile Ser Phe Ala Gln Lys
625                 630                 635                 640

Tyr Leu Ile Trp Glu Cys Cys Pro Lys Trp Arg Lys Phe Lys Met Ala
                645                 650                 655

Leu Phe Glu Leu Val Thr Asp Pro Phe Ala Glu Leu Thr Ile Thr Leu
            660                 665                 670

Cys Ile Val Val Asn Thr Val Phe Met Ala Met Glu His Tyr Pro Met
        675                 680                 685

Thr Asp Ala Phe Asp Ala Met Leu Gln Ala Gly Asn Ile Val Phe Thr
    690                 695                 700

Val Phe Phe Thr Met Glu Met Ala Phe Lys Ile Ile Ala Phe Asp Pro
705                 710                 715                 720

Tyr Tyr Tyr Phe Gln Lys Lys Trp Asn Ile Phe Asp Cys Val Ile Val
                725                 730                 735

Thr Val Ser Leu Leu Glu Leu Ser Ala Ser Lys Lys Gly Ser Leu Ser
            740                 745                 750

Val Leu Arg Thr Phe Arg Leu Leu Arg Val Phe Lys Leu Ala Lys Ser
        755                 760                 765

Trp Pro Thr Leu Asn Thr Leu Ile Lys Ile Ile Gly Asn Ser Val Gly
    770                 775                 780

Ala Leu Gly Asn Leu Thr Phe Ile Leu Ala Ile Ile Val Phe Ile Phe
785                 790                 795                 800

Ala Leu Val Gly Lys Gln Leu Leu Ser Glu Asp Tyr Gly Cys Arg Lys
                805                 810                 815

Asp Gly Val Ser Val Trp Asn Gly Glu Lys Leu Arg Trp His Met Cys
            820                 825                 830

Asp Phe Phe His Ser Phe Leu Val Val Phe Arg Ile Leu Cys Gly Glu
        835                 840                 845

Trp Ile Glu Asn Met Trp Val Cys Met Glu Val Ser Gln Lys Ser Ile
    850                 855                 860

Cys Leu Ile Leu Phe Leu Thr Val Met Val Leu Gly Asn Leu Val Val
865                 870                 875                 880

Leu Asn Leu Phe Ile Ala Leu Leu Leu Asn Ser Phe Ser Ala Asp Asn
```

-continued

```
                885                 890                 895

Leu Thr Ala Pro Glu Asp Asp Gly Glu Val Asn Asn Leu Gln Leu Ala
            900                 905                 910

Leu Ala Arg Ile Gln Val Leu Gly His Arg Ala Ser Arg Ala Ile Ala
        915                 920                 925

Ser Tyr Ile Ser Ser His Cys Arg Phe Arg Trp Pro Lys Val Glu Thr
    930                 935                 940

Gln Leu Gly Met Lys Pro Pro Leu Thr Ser Ser Glu Ala Lys Asn His
945                 950                 955                 960

Ile Ala Thr Asp Ala Val Ser Ala Ala Val Gly Asn Leu Thr Lys Pro
                965                 970                 975

Ala Leu Ser Ser Pro Lys Glu Asn His Gly Asp Phe Ile Thr Asp Pro
            980                 985                 990

Asn Val Trp Val Ser Val Pro Ile Ala Glu Gly Glu Ser Asp Leu Asp
        995                 1000                1005

Glu Leu Glu Glu Asp Met Glu Gln Ala Ser Gln Ser Ser Trp Gln Glu
    1010                1015                1020

Glu Asp Pro Lys Gly Gln Gln Glu Gln Leu Pro Gln Val Gln Lys Cys
1025                1030                1035                1040

Glu Asn His Gln Ala Ala Arg Ser Pro Ala Ser Met Met Ser Ser Glu
                1045                1050                1055

Asp Leu Ala Pro Tyr Leu Gly Glu Ser Trp Lys Arg Lys Asp Ser Pro
            1060                1065                1070

Gln Val Pro Ala Glu Gly Val Asp Asp Thr Ser Ser Ser Glu Gly Ser
        1075                1080                1085

Thr Val Asp Cys Pro Asp Pro Glu Glu Ile Leu Arg Lys Ile Pro Glu
    1090                1095                1100

Leu Ala Asp Asp Leu Asp Glu Pro Asp Asp Cys Phe Thr Glu Gly Cys
1105                1110                1115                1120

Thr Arg Arg Cys Pro Cys Cys Asn Val Asn Thr Ser Lys Ser Pro Trp
                1125                1130                1135

Ala Thr Gly Trp Gln Val Arg Lys Thr Cys Tyr Arg Ile Val Glu His
            1140                1145                1150

Ser Trp Phe Glu Ser Phe Ile Ile Phe Met Ile Leu Leu Ser Ser Gly
        1155                1160                1165

Ala Leu Ala Phe Glu Asp Asn Tyr Leu Glu Glu Lys Pro Arg Val Lys
    1170                1175                1180

Ser Val Leu Glu Tyr Thr Asp Arg Val Phe Thr Phe Ile Phe Val Phe
1185                1190                1195                1200

Glu Met Leu Leu Lys Trp Val Ala Tyr Gly Phe Lys Lys Tyr Phe Thr
                1205                1210                1215

Asn Ala Trp Cys Trp Leu Asp Phe Leu Ile Val Asn Ile Ser Leu Thr
            1220                1225                1230

Ser Leu Ile Ala Lys Ile Leu Glu Tyr Ser Asp Val Ala Ser Ile Lys
        1235                1240                1245

Ala Leu Arg Thr Leu Arg Ala Leu Arg Pro Leu Arg Ala Leu Ser Arg
    1250                1255                1260

Phe Glu Gly Met Arg Val Val Val Asp Ala Leu Val Gly Ala Ile Pro
1265                1270                1275                1280

Ser Ile Met Asn Val Leu Leu Val Cys Leu Ile Phe Trp Leu Ile Phe
                1285                1290                1295

Ser Ile Met Gly Val Asn Leu Phe Ala Gly Lys Phe Ser Lys Cys Val
            1300                1305                1310
```

-continued

```
Asp Thr Arg Asn Asn Pro Phe Ser Asn Val Asn Ser Thr Met Val Asn
        1315                1320                1325

Asn Lys Ser Glu Cys His Asn Gln Asn Ser Thr Gly His Phe Phe Trp
    1330                1335                1340

Val Asn Val Lys Val Asn Tyr Leu Ala Leu Leu Gln Val Ala Thr Phe
1345                1350                1355                1360

Lys Gly Trp Met Asp Ile Met Tyr Ala Ala Val Asp Ser Gly Glu Ile
                1365                1370                1375

Asn Ser Gln Pro Asn Trp Glu Asn Asn Leu Tyr Met Tyr Leu Tyr Phe
            1380                1385                1390

Val Phe Asp Asn Val Ala Met Gly Val Phe Ile Ile Phe Gly Gly Phe
        1395                1400                1405

Phe Thr Leu Asn Leu Phe Val Gly Val Ile Ile Asp Asn Phe Asn Gln
    1410                1415                1420

Gln Lys Lys Lys Leu Gly Gly Gln Asp Ile Phe Met Thr Glu Glu Gln
1425                1430                1435                1440

Lys Lys Tyr Tyr Asn Ala Met Lys Lys Leu Gly Ser Lys Lys Pro Gln
                1445                1450                1455

Lys Pro Ile Pro Arg Pro Leu Asn Lys Tyr Gln Gly Phe Val Phe Asp
            1460                1465                1470

Ile Val Thr Arg Gln Ala Phe Asp Ile Ile Ile Met Val Leu Ile Cys
        1475                1480                1485

Leu Asn Met Ile Thr Met Met Val Glu Thr Asp Glu Gln Gly Glu Glu
    1490                1495                1500

Lys Thr Lys Val Leu Gly Arg Ile Asn Gln Phe Phe Val Ala Val Phe
1505                1510                1515                1520

Thr Gly Glu Cys Val Met Lys Met Phe Ala Leu Arg Gln Tyr Tyr Phe
                1525                1530                1535

Thr Asn Gly Trp Asn Val Phe Asp Phe Ile Val Val Ile Leu Ser Ile
            1540                1545                1550

Gly Ser Leu Leu Phe Ser Ala Ile Leu Lys Ser Leu Glu Asn Tyr Phe
        1555                1560                1565

Ser Pro Thr Leu Phe Arg Val Ile Arg Leu Ala Arg Ile Gly Arg Ile
    1570                1575                1580

Leu Arg Leu Ile Arg Ala Ala Lys Gly Ile Arg Thr Leu Leu Phe Ala
1585                1590                1595                1600

Leu Met Met Ser Leu Pro Ala Leu Phe Asn Ile Gly Leu Leu Leu Phe
                1605                1610                1615

Leu Val Met Phe Ile Tyr Ser Ile Phe Gly Met Ala Ser Phe Ala Asn
            1620                1625                1630

Val Val Asp Glu Ala Gly Ile Asp Asp Met Phe Asn Phe Lys Thr Phe
        1635                1640                1645

Gly Asn Ser Met Leu Cys Leu Phe Gln Ile Thr Thr Ser Ala Gly Trp
    1650                1655                1660

Asp Gly Leu Leu Ser Pro Ile Leu Asn Thr Gly Pro Pro Tyr Cys Asp
1665                1670                1675                1680

Pro Asn Leu Pro Asn Ser Asn Gly Ser Arg Gly Asn Cys Gly Ser Pro
                1685                1690                1695

Ala Val Gly Ile Ile Phe Phe Thr Thr Tyr Ile Ile Ile Ser Phe Leu
            1700                1705                1710

Ile Val Val Asn Met Tyr Ile Ala Val Ile Leu Glu Asn Phe Asn Val
        1715                1720                1725
```

-continued

```
Ala Thr Glu Glu Ser Thr Glu Pro Leu Ser Glu Asp Asp Phe Asp Met
    1730                1735                1740

Phe Tyr Glu Thr Trp Glu Lys Phe Asp Pro Glu Ala Thr Gln Phe Ile
1745                1750                1755                1760

Ala Phe Ser Ala Leu Ser Asp Phe Ala Asp Thr Leu Ser Gly Pro Leu
                1765                1770                1775

Arg Ile Pro Lys Pro Asn Gln Asn Ile Leu Ile Gln Met Asp Leu Pro
            1780                1785                1790

Leu Val Pro Gly Asp Lys Ile His Cys Leu Asp Ile Leu Phe Ala Phe
        1795                1800                1805

Thr Lys Asn Val Leu Gly Glu Ser Gly Glu Leu Asp Ser Leu Lys Thr
    1810                1815                1820

Asn Met Glu Glu Lys Phe Met Ala Thr Asn Leu Ser Lys Ala Ser Tyr
1825                1830                1835                1840

Glu Pro Ile Ala Thr Thr Leu Arg Trp Lys Gln Glu Asp Leu Ser Ala
                1845                1850                1855

Thr Val Ile Gln Lys Ala Tyr Arg Ser Tyr Met Leu His Arg Ser Leu
            1860                1865                1870

Thr Leu Ser Asn Thr Leu His Val Pro Arg Ala Glu Glu Asp Gly Val
        1875                1880                1885

Ser Leu Pro Gly Glu Gly Tyr Val Thr Phe Met Ala Asn Ser Gly Leu
    1890                1895                1900

Pro Asp Lys Ser Glu Thr Ala Ser Ala Thr Ser Phe Pro Pro Ser Tyr
1905                1910                1915                1920

Asp Ser Val Thr Arg Gly Leu Ser Asp Arg Ala Asn Ile Asn Pro Ser
                1925                1930                1935

Ser Ser Met Gln Asn Glu Asp Glu Val Ala Ala Lys Glu Gly Asn Ser
            1940                1945                1950

Pro Gly Pro Gln
        1955
```

(2) INFORMATION FOR SEQ ID NO: 3:

(i) SEQUENCE CHARACTERISTICS:
(A) LENGTH: 702 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "DNA probe"

(iii) HYPOTHETICAL: NO (iv) ANTI-SENSE: NO (xi) SEQUENCE DESCRIPTION: SEQ ID NO: 3:

```
CTCAACATGG TTACGATGAT GGTGGAGACC GACGAGCAGG GCGAGGAGAA GACGAAGGTT     60

CTGGGCAGAA TCAACCAGTT CTTTGTGGCC GTCTTCACGG GCGAGTGTGT GATGAAGATG    120

TTCGCCCTGC GACAGTACTA TTTCACCAAC GGCTGGAACG TGTTCGACTT CATAGTGGTG    180

ATCCTGTCCA TTGGGAGTCT GCTGTTTTCT GCAATCCTTA AGTCACTGGA AAACTACTTC    240

TCCCCGACGC TCTTCCGGGT CATCCGTCTG GCCAGGATCG GCCGCATCCT CAGGCTGATC    300

CGAGCAGCCA AGGGGATTCG CACGCTGCTC TTCGCCCTCA TGATGTCCCT GCCCGCCCTC    360

TTCAACATCG GCCTCCTCCT CTTCCTCGTC ATGTTCATCT ACTCCATCTT CGGCATGGCC    420

AGCTTCGCTA ACGTCGTGGA CGAGGCCGGC ATCGACGACA TGTTCAACTT CAAGACCTTT    480
```

-continued

```
GGCAACAGCA TGCTGTGCCT GTTCCAGATC ACCACCTCGG CCGGCTGGGA CGGCCTCCTC    540

AGCCCCATCC TCAACACGGG GCCTCCCTAC TGCGACCCCA ACCTGCCCAA CAGCAACGGC    600

TCCCGGGGGA ACTGCGGGAG CCCGGCGGTG GGCATCATCT TCTTCACCAC CTACATCATC    660

ATCTCCTTCC TCATCGTGGT CAACATGTAT ATCGCAGTCA TC                       702
```

(2) INFORMATION FOR SEQ ID NO: 4:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "PCR primer"

(iii) HYPOTHETICAL: NO (iv) ANTI-SENSE: NO (xi) SEQUENCE DESCRIPTION: SEQ ID NO: 4:

```
AAGGCACTCA GGCATGCACA                                                 20
```

(2) INFORMATION FOR SEQ ID NO: 5:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "PCR primer"

(iii) HYPOTHETICAL: NO (iv) ANTI-SENSE: NO (xi) SEQUENCE DESCRIPTION: SEQ ID NO: 5:

```
TGGCCGACTC ACAGGTATTG                                                 20
```

(2) INFORMATION FOR SEQ ID NO: 6:

(i) SEQUENCE CHARACTERISTICS:
(A) LENGTH: 410 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "DNA probe"

(iii) HYPOTHETICAL: NO (iv) ANTI-SENSE: NO (xi) SEQUENCE DESCRIPTION: SEQ ID NO: 6:

```
AAGGCACTCA GGCATGCACA GGGCAGGTTC CAATGTCTTT CTCTGCTGTG CTAACTCCTT     60

CCCTCTGGAG GTGGCACCAA CCTCCAGCCT CCACCAATGC ATGTCACTGG TCATGGTGTC    120

AGAACTGAAT GGGGACATCC TTGAGAAAGC CCCCACCCCA ATAGGAATCA AAAGCCAAGG    180

ATACTCCTCC ATTCTGACGT CCCTTCCGAG TTCCCAGAAG ATGTCATTGC TCCCTTCTGT    240

TTGTGACCAG AGACGTGATT CACCAACTTC TCGGAGCCAG AGACACATAC CAAAGACTTT    300

TCTGCTGGTG TCGGGCAGTC TTAGAGAAGT CACGTAGGGG TTGGCACTGA GAATTAGGGT    360

TTGCATGCCT GCATGCTCAC AGCTGCCGGA CAATACCTGT GAGTCGGCCA               410
```

-continued (2) INFORMATION FOR SEQ ID NO: 7:

(i) SEQUENCE CHARACTERISTICS:
(A) LENGTH: 46 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "DNA probe"

(iii) HYPOTHETICAL: NO (iv) ANTI-SENSE: NO (xi) SEQUENCE DESCRIPTION: SEQ ID NO: 7:

AGGCACTCAG GCATGCACAG GGCAGGTTCC AATGTCTTTC TCTGCT 46

(2) INFORMATION FOR SEQ ID NO: 8:

(i) SEQUENCE CHARACTERISTICS:
(A) LENGTH: 46 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "DNA probe"

(iii) HYPOTHETICAL: NO (iv) ANTI-SENSE: NO (xi) SEQUENCE DESCRIPTION: SEQ ID NO: 8:

TCCGTGAGTC CGTACGTGTC CCGTCCAAGG TTACAGAAAG AGACGA 46

(2) INFORMATION FOR SEQ ID NO: 9:

(i) SEQUENCE CHARACTERISTICS:
(A) LENGTH: 5874 base pairs
(B) TYPE: nucleic acid
(C) STRANDEDNESS: unknown
(D) TOPOLOGY: unknown (ii) MOLECULE TYPE: cDNA (iii) HYPOTHETICAL: NO (iv) ANTI-SENSE: NO (xi) SEQUENCE DESCRIPTION: SEQ ID NO: 9:

ATGGAATTCC CCATTGGATC CCTCGAAACT AACAACTTCC GTCGCTTTAC TCCGGAGTCA 60

CTGGTGGAGA TAGAGAAGCA AATTGCTGCC AAGCAGGGAA CAAAGAAAGC CAGAGAGAAG 120

CATAGGGAGC AGAAGGACCA AGAAGAGAAG CCTCGGCCCC AGCTGGACTT GAAAGCCTGC 180

AACCAGCTGC CCAAGTTCTA TGGTGAGCTC CCAGCAGAAC TGATCGGGGA GCCCCTGGAG 240

GATCTAGATC CGTTCTACAG CACACACCGG ACATTTATGG TGCTGAACAA AGGGAGGACC 300

ATTTCCCGGT TTAGTGCCAC TCGGGCCCTG TGGCTATTCA GTCCTTTCAA CCTGATCAGA 360

AGAACGGCCA TCAAAGTGTC TGTCCACTCG TGGTTCAGTT TATTTATTAC GGTCACTATT 420

TTGGTTAATT GTGTGTGCAT GACCCGAACT GACCTTCCAG AGAAAATTGA ATATGTCTTC 480

ACTGTCATTT ACACCTTTGA AGCCTTGATA AAGATACTGG CAAGAGGATT TTGTCTAAAT 540

GAGTTCACGT ACCTGAGAGA TCCTTGGAAC TGGCTGGATT TTAGCGTCAT TACCCTGGCA 600

TATGTTGGCA CAGCAATAGA TCTCCGTGGG ATCTCAGGCC TGCGGACATT CAGAGTTCTT 660

-continued

```
AGAGCATTAA AAACAGTTTC TGTGATCCCA GGCCTGAAGG TCATTGTGGG GGCCCTGATT    720
CACTCAGTGA AGAAACTGGC TGATGTGACC ATCCTCACCA TCTTCTGCCT AAGTGTTTTT    780
GCCTTGGTGG GGCTGCAACT CTTCAAGGGC AACCTCAAAA ATAAATGTGT CAAGAATGAC    840
ATGGCTGTCA ATGAGACAAC CAACTACTCA TCTCACAGAA AACCAGATAT CTACATAAAT    900
AAGCGAGGCA CTTCTGACCC CTTACTGTGT GGCAATGGAT CTGACTCAGG CCACTGCCCT    960
GATGGTTATA TCTGCCTTAA AACTTCTGAC AACCCGGATT TTAACTACAC CAGCTTTGAT   1020
TCCTTTGCTT GGGCTTTCCT CTCACTGTTC CGCCTCATGA CACAGGATTC CTGGGAACGC   1080
CTCTACCAGC AGACCCTGAG GACTTCTGGG AAAATCTATA TGATCTTTTT TGTGCTCGTA   1140
ATCTTCCTGG GATCTTTCTA CCTGGTCAAC TTGATCTTGG CTGTAGTCAC CATGGCGTAT   1200
GAGGAGCAGA ACCAGGCAAC CACTGATGAA ATTGAAGCAA AGGAGAAGAA GTTCCAGGAT   1260
GCCCTCGAGA TGCTCCGGAA GGAGCAGGAG GTGCTAGCAG CACTAGGGAT TGACACAACC   1320
TCTCTCCACT CCCACAATGG ATCACCTTTA ACCTCCAAAA ATGCCAGTGA GAGAAGGCAT   1380
AGAATAAAGC CAAGAGTGTC AGAGGGCTCC ACAGAAGACA ACAAATCACC CCGCTCTGAT   1440
CCTTACAACC AGCGCAGGAT GTCTTTTCTA GGCCTCGCCT CTGGAAAACG CCGGGCTAGT   1500
CATGGCAGTG TGTTCCATTT CCGGTCCCCT GGCCGAGATA TCTCACTCCC TGAGGGAGTC   1560
ACAGATGATG GAGTCTTTCC TGGAGACCAC GAAAGCCATC GGGGCTCTCT GCTGCTGGGT   1620
GGGGGTGCTG GCCAGCAAGG CCCCCTCCCT AGAAGCCCTC TTCCTCAACC CAGCAACCCT   1680
GACTCCAGGC ATGGAGAAGA TGAACACCAA CCGCCGCCCA CTAGTGAGCT TGCCCCTGGA   1740
GCTGTCGATG TCTCGGCATT CGATGCAGGA CAAAAGAAGA CTTTCTTGTC AGCAGAATAC   1800
TTAGATGAAC CTTTCCGGGC CCAAAGGGCA ATGAGTGTTG TCAGTATCAT AACCTCCGTC   1860
CTTGAGGAAC TCGAGGAGTC TGAACAGAAG TGCCCACCCT GCTTGACCAG CTTGTCTCAG   1920
AAGTATCTGA TCTGGGATTG CTGCCCCATG TGGGTGAAGC TCAAGACAAT TCTCTTTGGG   1980
CTTGTGACGG ATCCCTTTGC AGAGCTCACC ATCACCTTGT GCATCGTGGT GAACACCATC   2040
TTCATGGCCA TGGAGCACCA TGGCATGAGC CCTACCTTCG AAGCCATGCT CCAGATAGGC   2100
AACATCGTCT TTACCATATT TTTTACTGCT GAAATGGTCT TCAAAATCAT TGCCTTCGAC   2160
CCATACTATT ATTTCCAGAA GAAGTGGAAT ATCTTTGACT GCATCATCGT CACTGTGAGT   2220
CTGCTAGAGC TGGGCGTGGC CAAGAAGGGA AGCCTGTCTG TGCTGCGGAG CTTCCGCTTG   2280
CTGCGCGTAT TCAAGCTGGC CAAATCCTGG CCCACCTTAA ACACACTCAT CAAGATCATC   2340
GGAAACTCAG TGGGGGCACT GGGGAACCTC ACCATCATCC TGGCCATCAT TGTCTTTGTC   2400
TTTGCTCTGG TTGGCAAGCA GCTCCTAGGG GAAAACTACC GTAACAACCG AAAAAATATC   2460
TCCGCGCCCC ATGAAGACTG GCCCCGCTGG CACATGCACG ACTTCTTCCA CTCTTTCCTC   2520
ATTGTCTTCC GTATCCTCTG TGGAGAGTGG ATTGAGAACA TGTGGGCCTG CATGGAAGTT   2580
GGCCAAAAAT CCATATGCCT CATCCTTTTC TTGACGGTGA TGGTGCTAGG GAACCTGGTG   2640
GTGCTTAACC TGTTCATCGC CCTGCTATTG AACTCTTTCA GTGCTGACAA CCTCACAGCC   2700
CCGGAGGACG ATGGGGAGGT GAACAACCTG CAGGTGGCCC TGGCACGGAT CCAGGTCTTT   2760
GGCCATCGTA CCAAACAGGC TCTTTGCAGC TTCTTCAGCA GGTCCTGCCC ATTCCCCCAG   2820
CCCAAGGCAG AGCCTGAGCT GGTGGTGAAA CTCCCACTCT CCAGCTCCAA GGCTGAGAAC   2880
CACATTGCTG CCAACACTGC CAGGGGGAGC TCTGGAGGGC TCCAAGCTCC CAGAGGCCCC   2940
AGGGATGAGC ACAGTGACTT CATCGCTAAT CCGACTGTGT GGGTCTCTGT GCCCATTGCT   3000
```

-continued

```
GAGGGTGAAT CTGATCTTGA TGACTTGGAG GATGATGGTG GGGAAGATGC TCAGAGCTTC   3060

CAGCAGGAAG TGATCCCCAA AGGACAGCAG GAGCAGCTGC AGCAAGTCGA GAGGTGTGGG   3120

GACCACCTGA CACCCAGGAG CCCAGGCACT GGAACATCTT CTGAGGACCT GGCTCCATCC   3180

CTGGGTGAGA CGTGGAAAGA TGAGTCTGTT CCTCAGGCCC CTGCTGAGGG AGTGGACGAC   3240

ACAAGCTCCT CTGAGGGCAG CACGGTGGAC TGCCTAGATC CTGAGGAAAT CCTGAGGAAG   3300

ATCCCTGAGC TGGCAGATGA CCTGGAAGAA CCAGATGACT GCTTCACAGA AGGATGCATT   3360

CGCCACTGTC CCTGCTGCAA ACTGGATACC ACCAAGAGTC CATGGGATGT GGGCTGGCAG   3420

GTGCGCAAGA CTTGCTACCG TATCGTGGAG CACAGCTGGT TTGAGAGCTT CATCATCTTC   3480

ATGATCCTGC TCAGCAGTGG ATCTCTGGCC TTTGAAGACT ATTACCTGGA CCAGAAGCCC   3540

ACGGTGAAAG CTTTGCTGGA GTACACTGAC AGGGTCTTCA CCTTTATCTT TGTGTTCGAG   3600

ATGCTGCTTA AGTGGGTGGC CTATGGCTTC AAAAAGTACT TCACCAATGC CTGGTGCTGG   3660

CTGGACTTCC TCATTGTGAA TATCTCACTG ATAAGTCTCA CAGCGAAGAT TCTGGAATAT   3720

TCTGAAGTGG CTCCCATCAA AGCCCTTCGA ACCCTTCGCG CTCTGCGGCC ACTGCGGGCT   3780

CTTTCTCGAT TTGAAGGCAT GCGGGTGGTG GTGGATGCCC TGGTGGGCGC CATCCCATCC   3840

ATCATGAATG TCCTCCTCGT CTGCCTCATC TTCTGGCTCA TCTTCAGCAT CATGGGTGTG   3900

AACCTCTTCG CAGGGAAGTT TTGGAGGTGC ATCAACTATA CCGATGGAGA GTTTTCCCTT   3960

GTACCTTTGT CGATTGTGAA TAACAAGTCT GACTGCAAGA TTCAAAACTC CACTGGCAGC   4020

TTCTTCTGGG TCAATGTGAA AGTCAACTTT GATAATGTTG CAATGGGTTA CCTTGCACTT   4080

CTGCAGGTGG CAACCTTTAA AGGCTGGATG GACATTATGT ATGCAGCTGT TGATTCCCGG   4140

GAGGTCAACA TGCAACCCAA GTGGGAGGAC AACGTGTACA TGTATTTGTA CTTTGTCATC   4200

TTCATCATTT TTGGAGGCTT CTTCACACTG AATCTCTTTG TTGGGGTCAT AATTGACAAC   4260

TTCAATCAAC AGAAAAAAAA GTTAGGGGGC CAGGACATCT TCATGACAGA GGAGCAGAAG   4320

AAATACTACA ATGCCATGAA GAAGTTGGGC TCCAAGAAGC CCCAGAAGCC CATCCCACGG   4380

CCCCTGAACA AGTTCCAGGG TTTTGTCTTT GACATCGTGA CCAGACAAGC TTTTGACATC   4440

ACCATCATGG TCCTCATCTG CCTCAACATG ATCACCATGA TGGTGGAGAC TGATGACCAA   4500

AGTGAAGAAA AGACGAAAAT TCTGGGCAAA ATCAACCAGT TCTTTGTGGC CGTCTTCACA   4560

GGCGAATGTG TCATGAAGAT GTTCGCTTTG AGGCAGTACT ACTTCACAAA TGGCTGGAAT   4620

GTGTTTGACT TCATTGTGGT GGTTCTCTCC ATTGCGAGCC TGATTTTTTC TGCAATTCTT   4680

AAGTCACTTC AAAGTTACTT CTCCCCAACG CTCTTCAGAG TCATCCGCCT GGCCCGAATT   4740

GGCCGCATCC TCAGACTGAT CCGAGCGGCC AAGGGGATCC GCACACTGCT CTTTGCCCTC   4800

ATGATGTCCC TGCCTGCCCT CTTCAACATC GGGCTGTTGC TATTCCTTGT CATGTTCATC   4860

TACTCCATCT TCGGTATGTC CAGCTTTCCC CATGTGAGGT GGGAGGCTGG CATCGACGAC   4920

ATGTTCAACT TCCAGACCTT CGCCAACAGC ATGCTGTGCC TCTTCCAGAT TACCACGTCG   4980

GCCGGCTGGG ATGGCCTCCT CAGCCCCATC CTCAACACAG GGCCCCCCTA CTGTGACCCC   5040

AATCTGCCCA ACAGCAATGG CACCAGAGGG GACTGTGGGA GCCCAGCCGT AGGCATCATC   5100

TTCTTCACCA CCTACATCAT CATCTCCTTC CTCATCGTGG TCAACATGTA CATTGCAGTG   5160

ATTCTGGAGA ACTTCAATGT GGCCACGGAG GAGAGCACTG AGCCCCTGAG TGAGGACGAC   5220

TTTGACATGT TCTATGAGAC CTGGGAGAAG TTTGACCCAG AGGCCACTCA GTTTATTACC   5280

TTTTCTGCTC TCTCGGACTT TGCAGACACT CTCTCTGGTC CCCTGAGAAT CCCAAAACCC   5340

AATCGAAATA TACTGATCCA GATGGACCTG CCTTTGGTCC CTGGAGATAA GATCCACTGC   5400
```

-continued

```
TTGGACATCC TTTTTGCTTT CACCAAGAAT GTCCTAGGAG AATCCGGGGA GTTGGATTCT   5460

CTGAAGGCAA ATATGGAGGA GAAGTTTATG GCAACTAATC TTTCAAAATC ATCCTATGAA   5520

CCAATAGCAA CCACTCTCCG ATGGAAGCAA GAAGACATTT CAGCCACTGT CATTCAAAAG   5580

GCCTATCGGA GCTATGTGCT GCACCGCTCC ATGGCACTCT CTAACACCCC ATGTGTGCCC   5640

AGAGCTGAGG AGGAGGCTGC ATCACTCCCA GATGAAGGTT TTGTTGCATT CACAGCAAAT   5700

GAAAATTGTG TACTCCCAGA CAAATCTGAA ACTGCTTCTG CCACATCATT CCCACCGTCC   5760

TATGAGAGTG TCACTAGAGG CCTTAGTGAT AGAGTCAACA TGAGGACATC TAGCTCAATA   5820

CAAAATGAAG ATGAAGCCAC CAGTATGGAG CTGATTGCCC CTGGGCCCTA GTGA         5874
```

(2) INFORMATION FOR SEQ ID NO: 10:

(i) SEQUENCE CHARACTERISTICS:
(A) LENGTH: 1956 amino acids
(B) TYPE: amino acid
(C) STRANDEDNESS: unknown
(D) TOPOLOGY: unknown (ii) MOLECULE TYPE: peptide (iii) HYPOTHETICAL: NO (iv) ANTI-SENSE: NO (xi) SEQUENCE DESCRIPTION: SEQ ID NO: 10:

```
Met Glu Phe Pro Ile Gly Ser Leu Glu Thr Asn Asn Phe Arg Arg Phe
1               5                   10                  15

Thr Pro Glu Ser Leu Val Glu Ile Glu Lys Gln Ile Ala Ala Lys Gln
            20                  25                  30

Gly Thr Lys Lys Ala Arg Glu Lys His Arg Glu Gln Lys Asp Gln Glu
        35                  40                  45

Glu Lys Pro Arg Pro Gln Leu Asp Leu Lys Ala Cys Asn Gln Leu Pro
    50                  55                  60

Lys Phe Tyr Gly Glu Leu Pro Ala Glu Leu Ile Gly Glu Pro Leu Glu
65                  70                  75                  80

Asp Leu Asp Pro Phe Tyr Ser Thr His Arg Thr Phe Met Val Leu Asn
                85                  90                  95

Lys Gly Arg Thr Ile Ser Arg Phe Ser Ala Thr Arg Ala Leu Trp Leu
            100                 105                 110

Phe Ser Pro Phe Asn Leu Ile Arg Arg Thr Ala Ile Lys Val Ser Val
        115                 120                 125

His Ser Trp Phe Ser Leu Phe Ile Thr Val Thr Ile Leu Val Asn Cys
    130                 135                 140

Val Cys Met Thr Arg Thr Asp Leu Pro Glu Lys Ile Glu Tyr Val Phe
145                 150                 155                 160

Thr Val Ile Tyr Thr Phe Glu Ala Leu Ile Lys Ile Leu Ala Arg Gly
                165                 170                 175

Phe Cys Leu Asn Glu Phe Thr Tyr Leu Arg Asp Pro Trp Asn Trp Leu
            180                 185                 190

Asp Phe Ser Val Ile Thr Leu Ala Tyr Val Gly Thr Ala Ile Asp Leu
        195                 200                 205

Arg Gly Ile Ser Gly Leu Arg Thr Phe Arg Val Leu Arg Ala Leu Lys
    210                 215                 220

Thr Val Ser Val Ile Pro Gly Leu Lys Val Ile Val Gly Ala Leu Ile
225                 230                 235                 240
```

-continued

```
His Ser Val Lys Lys Leu Ala Asp Val Thr Ile Leu Thr Ile Phe Cys
                245                 250                 255

Leu Ser Val Phe Ala Leu Val Gly Leu Gln Leu Phe Lys Gly Asn Leu
            260                 265                 270

Lys Asn Lys Cys Val Lys Asn Asp Met Ala Val Asn Glu Thr Thr Asn
        275                 280                 285

Tyr Ser Ser His Arg Lys Pro Asp Ile Tyr Ile Asn Lys Arg Gly Thr
    290                 295                 300

Ser Asp Pro Leu Leu Cys Gly Asn Gly Ser Asp Ser Gly His Cys Pro
305                 310                 315                 320

Asp Gly Tyr Ile Cys Leu Lys Thr Ser Asp Asn Pro Asp Phe Asn Tyr
                325                 330                 335

Thr Ser Phe Asp Ser Phe Ala Trp Ala Phe Leu Ser Leu Phe Arg Leu
            340                 345                 350

Met Thr Gln Asp Ser Trp Glu Arg Leu Tyr Gln Gln Thr Leu Arg Thr
        355                 360                 365

Ser Gly Lys Ile Tyr Met Ile Phe Phe Val Leu Val Ile Phe Leu Gly
    370                 375                 380

Ser Phe Tyr Leu Val Asn Leu Ile Leu Ala Val Val Thr Met Ala Tyr
385                 390                 395                 400

Glu Glu Gln Asn Gln Ala Thr Thr Asp Glu Ile Glu Ala Lys Glu Lys
                405                 410                 415

Lys Phe Gln Glu Ala Leu Glu Met Leu Arg Lys Glu Gln Glu Val Leu
            420                 425                 430

Ala Ala Leu Gly Ile Asp Thr Thr Ser Leu His Ser His Asn Gly Ser
        435                 440                 445

Pro Leu Thr Ser Lys Asn Ala Ser Glu Arg Arg His Arg Ile Lys Pro
    450                 455                 460

Arg Val Ser Glu Gly Ser Thr Glu Asp Asn Lys Ser Pro Arg Ser Asp
465                 470                 475                 480

Pro Tyr Asn Gln Arg Arg Met Ser Phe Leu Gly Leu Ala Ser Gly Lys
                485                 490                 495

Arg Arg Ala Ser His Gly Ser Val Phe His Phe Arg Ser Pro Gly Arp
            500                 505                 510

Asp Ile Ser Leu Pro Glu Gly Val Thr Asp Asp Gly Val Phe Pro Gly
        515                 520                 525

Asp His Glu Ser His Arg Gly Ser Leu Leu Leu Gly Gly Gly Ala Gly
    530                 535                 540

Gln Gln Gly Pro Leu Pro Arg Ser Pro Leu Pro Gln Pro Ser Asn Pro
545                 550                 555                 560

Asp Ser Arg His Gly Glu Asp Glu His Gln Pro Pro Pro Thr Ser Glu
                565                 570                 575

Leu Ala Pro Gly Ala Val Asp Val Ser Ala Phe Asp Ala Gly Gln Lys
            580                 585                 590

Lys Thr Phe Leu Ser Ala Glu Tyr Leu Asp Glu Pro Phe Arg Ala Gln
        595                 600                 605

Arg Ala Met Ser Val Val Ser Ile Ile Thr Ser Val Leu Glu Glu Leu
    610                 615                 620

Glu Glu Ser Glu Gln Lys Cys Pro Pro Cys Leu Thr Ser Leu Ser Gln
625                 630                 635                 640

Lys Tyr Leu Ile Trp Asp Cys Cys Pro Met Trp Val Lys Leu Lys Thr
                645                 650                 655

Ile Leu Phe Gly Leu Val Thr Asp Pro Phe Ala Glu Leu Thr Ile Thr
```

-continued

```
            660                 665                 670

Leu Cys Ile Val Val Asn Thr Ile Phe Met Ala Met Glu His His Gly
        675                 680                 685

Met Ser Pro Thr Phe Glu Ala Met Leu Gln Ile Gly Asn Ile Val Phe
    690                 695                 700

Thr Ile Phe Phe Thr Ala Glu Met Val Phe Lys Ile Ile Ala Phe Asp
705                 710                 715                 720

Pro Tyr Tyr Tyr Phe Gln Lys Lys Trp Asn Ile Phe Asp Cys Ile Ile
                725                 730                 735

Val Thr Val Ser Leu Leu Glu Leu Gly Val Ala Lys Lys Gly Ser Leu
            740                 745                 750

Ser Val Leu Arg Ser Phe Arg Leu Leu Arg Val Phe Lys Leu Ala Lys
        755                 760                 765

Ser Trp Pro Thr Leu Asn Thr Leu Ile Lys Ile Ile Gly Asn Ser Val
    770                 775                 780

Gly Ala Leu Gly Asn Leu Thr Ile Ile Leu Ala Ile Ile Val Phe Val
785                 790                 795                 800

Phe Ala Leu Val Gly Lys Gln Leu Leu Gly Glu Asn Tyr Arg Asn Asn
                805                 810                 815

Arg Lys Asn Ile Ser Ala Pro His Glu Asp Trp Pro Arg Trp His Met
            820                 825                 830

His Asp Phe Phe His Ser Phe Leu Ile Val Phe Arg Ile Leu Cys Gly
        835                 840                 845

Glu Trp Ile Glu Asn Met Trp Ala Cys Met Glu Val Gly Gln Lys Ser
    850                 855                 860

Ile Cys Leu Ile Leu Phe Leu Thr Val Met Val Leu Gly Asn Leu Val
865                 870                 875                 880

Val Leu Asn Leu Phe Ile Ala Leu Leu Leu Asn Ser Phe Ser Ala Asp
                885                 890                 895

Asn Leu Thr Ala Pro Glu Asp Asp Gly Glu Val Asn Asn Leu Gln Val
            900                 905                 910

Ala Leu Ala Arg Ile Gln Val Phe Gly His Arg Thr Lys Gln Ala Leu
        915                 920                 925

Cys Ser Phe Phe Ser Arg Ser Cys Pro Phe Pro Gln Pro Lys Ala Glu
    930                 935                 940

Pro Glu Leu Val Val Lys Leu Pro Leu Ser Ser Ser Lys Ala Glu Asn
945                 950                 955                 960

His Ile Ala Ala Asn Thr Ala Arg Gly Ser Ser Gly Gly Leu Gln Ala
                965                 970                 975

Pro Arg Gly Pro Arg Asp Glu His Ser Asp Phe Ile Ala Asn Pro Thr
            980                 985                 990

Val Trp Val Ser Val Pro Ile Ala Glu Gly Glu Ser Asp Leu Asp Asp
        995                 1000                1005

Leu Glu Asp Asp Gly Gly Glu Asp Ala Gln Ser Phe Gln Gln Glu Val
    1010                1015                1020

Ile Pro Lys Gly Gln Gln Glu Gln Leu Gln Gln Val Glu Arg Cys Gly
1025                1030                1035                1040

Asp His Leu Thr Pro Arg Ser Pro Gly Thr Gly Thr Ser Ser Glu Asp
                1045                1050                1055

Leu Ala Pro Ser Leu Gly Glu Thr Trp Lys Asp Glu Ser Val Pro Gln
            1060                1065                1070

Ala Pro Ala Glu Gly Val Asp Asp Thr Ser Ser Ser Glu Gly Ser Thr
        1075                1080                1085
```

-continued

```
Val Asp Cys Leu Asp Pro Glu Glu Ile Leu Arg Lys Ile Pro Glu Leu
    1090                1095                1100

Ala Asp Asp Leu Glu Glu Pro Asp Asp Cys Phe Thr Glu Gly Cys Ile
1105                1110                1115                1120

Arg His Cys Pro Cys Cys Lys Leu Asp Thr Thr Lys Ser Pro Trp Asp
                1125                1130                1135

Val Gly Trp Gln Val Arg Lys Thr Cys Tyr Arg Ile Val Glu His Ser
            1140                1145                1150

Trp Phe Glu Ser Phe Ile Ile Phe Met Ile Leu Leu Ser Ser Gly Ser
        1155                1160                1165

Leu Ala Phe Glu Asp Tyr Tyr Leu Asp Gln Lys Pro Thr Val Lys Ala
    1170                1175                1180

Leu Leu Glu Tyr Thr Asp Arg Val Phe Thr Phe Ile Phe Val Phe Glu
1185                1190                1195                1200

Met Leu Leu Lys Trp Val Ala Tyr Gly Phe Lys Lys Tyr Phe Thr Asn
                1205                1210                1215

Ala Trp Cys Trp Leu Asp Phe Leu Ile Val Asn Ile Ser Leu Ile Ser
            1220                1225                1230

Leu Thr Ala Lys Ile Leu Glu Tyr Ser Glu Val Ala Pro Ile Lys Ala
        1235                1240                1245

Leu Arg Thr Leu Arg Ala Leu Arg Pro Leu Arg Ala Leu Ser Arg Phe
    1250                1255                1260

Glu Gly Met Arg Val Val Val Asp Ala Leu Val Gly Ala Ile Pro Ser
1265                1270                1275                1280

Ile Met Asn Val Leu Leu Val Cys Leu Ile Phe Trp Leu Ile Phe Ser
                1285                1290                1295

Ile Met Gly Val Asn Leu Phe Ala Gly Lys Phe Trp Arg Cys Ile Asn
            1300                1305                1310

Tyr Thr Asp Gly Glu Phe Ser Leu Val Pro Leu Ser Ile Val Asn Asn
        1315                1320                1325

Lys Ser Asp Cys Lys Ile Gln Asn Ser Thr Gly Ser Phe Phe Trp Val
    1330                1335                1340

Asn Val Lys Val Asn Phe Asp Asn Val Ala Met Gly Tyr Leu Ala Leu
1345                1350                1355                1360

Leu Gln Val Ala Thr Phe Lys Gly Trp Met Asp Ile Met Tyr Ala Ala
                1365                1370                1375

Val Asp Ser Arg Glu Val Asn Met Gln Pro Lys Trp Glu Asp Asn Val
            1380                1385                1390

Tyr Met Tyr Leu Tyr Phe Val Ile Phe Ile Ile Phe Gly Gly Phe Phe
        1395                1400                1405

Thr Leu Asn Leu Phe Val Gly Val Ile Ile Asp Asn Phe Asn Gln Gln
    1410                1415                1420

Lys Lys Lys Leu Gly Gly Gln Asp Ile Phe Met Thr Glu Glu Gln Lys
1425                1430                1435                1440

Lys Tyr Tyr Asn Ala Met Lys Lys Leu Gly Ser Lys Lys Pro Gln Lys
                1445                1450                1455

Pro Ile Pro Arg Pro Leu Asn Lys Phe Gln Gly Phe Val Phe Asp Ile
            1460                1465                1470

Val Thr Arg Gln Ala Phe Asp Ile Thr Ile Met Val Leu Ile Cys Leu
        1475                1480                1485

Asn Met Ile Thr Met Met Val Glu Thr Asp Asp Gln Ser Glu Glu Lys
    1490                1495                1500
```

-continued

```
Thr Lys Ile Leu Gly Lys Ile Asn Gln Phe Phe Val Ala Val Phe Thr
1505                1510                1515                1520

Gly Glu Cys Val Met Lys Met Phe Ala Leu Arg Gln Tyr Tyr Phe Thr
                1525                1530                1535

Asn Gly Trp Asn Val Phe Asp Phe Ile Val Val Val Leu Ser Ile Ala
            1540                1545                1550

Ser Leu Ile Phe Ser Ala Ile Leu Lys Ser Leu Gln Ser Tyr Phe Ser
        1555                1560                1565

Pro Thr Leu Phe Arg Val Ile Arg Leu Ala Arg Ile Gly Arg Ile Leu
    1570                1575                1580

Arg Leu Ile Arg Ala Ala Lys Gly Ile Arg Thr Leu Leu Phe Ala Leu
1585                1590                1595                1600

Met Met Ser Leu Pro Ala Leu Phe Asn Ile Gly Leu Leu Leu Phe Leu
                1605                1610                1615

Val Met Phe Ile Tyr Ser Ile Phe Gly Met Ser Ser Phe Pro His Val
            1620                1625                1630

Arg Trp Glu Ala Gly Ile Asp Asp Met Phe Asn Phe Gln Thr Phe Ala
        1635                1640                1645

Asn Ser Met Leu Cys Leu Phe Gln Ile Thr Thr Ser Ala Gly Trp Asp
    1650                1655                1660

Gly Leu Leu Ser Pro Ile Leu Asn Thr Gly Pro Pro Tyr Cys Asp Pro
1665                1670                1675                1680

Asn Leu Pro Asn Ser Asn Gly Thr Arg Gly Asp Cys Gly Ser Pro Ala
                1685                1690                1695

Val Gly Ile Ile Phe Phe Thr Thr Tyr Ile Ile Ile Ser Phe Leu Ile
            1700                1705                1710

Val Val Asn Met Tyr Ile Ala Val Ile Leu Glu Asn Phe Asn Val Ala
        1715                1720                1725

Thr Glu Glu Ser Thr Glu Pro Leu Ser Glu Asp Asp Phe Asp Met Phe
    1730                1735                1740

Tyr Glu Thr Trp Glu Lys Phe Asp Pro Glu Ala Thr Gln Phe Ile Thr
1745                1750                1755                1760

Phe Ser Ala Leu Ser Asp Phe Ala Asp Thr Leu Ser Gly Pro Leu Arg
                1765                1770                1775

Ile Pro Lys Pro Asn Arg Asn Ile Leu Ile Gln Met Asp Leu Pro Leu
            1780                1785                1790

Val Pro Gly Asp Lys Ile His Cys Leu Asp Ile Leu Phe Ala Phe Thr
        1795                1800                1805

Lys Asn Val Leu Gly Glu Ser Gly Glu Leu Asp Ser Leu Lys Ala Asn
    1810                1815                1820

Met Glu Glu Lys Phe Met Ala Thr Asn Leu Ser Lys Ser Ser Tyr Glu
1825                1830                1835                1840

Pro Ile Ala Thr Thr Leu Arg Trp Lys Gln Glu Asp Ile Ser Ala Thr
                1845                1850                1855

Val Ile Gln Lys Ala Tyr Arg Ser Tyr Val Leu His Arg Ser Met Ala
            1860                1865                1870

Leu Ser Asn Thr Pro Cys Val Pro Arg Ala Glu Glu Glu Ala Ala Ser
        1875                1880                1885

Leu Pro Asp Glu Gly Phe Val Ala Phe Thr Ala Asn Glu Asn Cys Val
    1890                1895                1900

Leu Pro Asp Lys Ser Glu Thr Ala Ser Ala Thr Ser Phe Pro Pro Ser
1905                1910                1915                1920

Tyr Glu Ser Val Thr Arg Gly Leu Ser Asp Arg Val Asn Met Arg Thr
```

-continued

```
                1925                1930                1935

Ser Ser Ser Ile Gln Asn Glu Asp Glu Ala Thr Ser Met Glu Leu Ile
            1940                1945                1950

Ala Pro Gly Pro
        1955
```